(12) United States Patent
Samuelson et al.

(10) Patent No.: US 9,730,808 B2
(45) Date of Patent: *Aug. 15, 2017

(54) SYSTEMS AND METHODS FOR PROVIDING A FEMORAL COMPONENT

(71) Applicants: Kent M. Samuelson, Salt Lake City, UT (US); Connor E. Samuelson, Salt Lake City, UT (US)

(72) Inventors: Kent M. Samuelson, Salt Lake City, UT (US); Connor E. Samuelson, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/144,668

(22) Filed: May 2, 2016

(65) Prior Publication Data

US 2016/0242918 A1    Aug. 25, 2016

Related U.S. Application Data

(63) Continuation of application No. 14/270,110, filed on May 5, 2014, now Pat. No. 9,326,867, which is a
(Continued)

(51) Int. Cl.
*A61F 2/38* (2006.01)
*A61F 2/46* (2006.01)
(Continued)

(52) U.S. Cl.
CPC .............. *A61F 2/46* (2013.01); *A61B 17/155* (2013.01); *A61B 17/1675* (2013.01); *A61F 2/30734* (2013.01); *A61F 2/30756* (2013.01); *A61F 2/30767* (2013.01); *A61F 2/38* (2013.01); *A61F 2/389* (2013.01); *A61F 2/3859* (2013.01);
(Continued)

(58) Field of Classification Search
CPC ............. A61F 2/3859; A61F 2/38; A61F 2/46
See application file for complete search history.

(56) References Cited

U.S. PATENT DOCUMENTS 4,209,861 A    7/1980    Walker et al.
4,487,203 A    12/1984    Androphy
(Continued)

FOREIGN PATENT DOCUMENTS

CN         1874738 A     12/2006
CN       101123928 A      2/2008
(Continued)

*Primary Examiner* — Jason-Dennis Stewart
(74) *Attorney, Agent, or Firm* — David B. Tingey; Bryant J. Keller; Kirton McConkie

(57) ABSTRACT

Systems and methods for providing deeper knee flexion capabilities. In some instances, such systems and methods include a femoral component that is configured to replace a distal portion of a femur. In some cases, the femoral component comprises a first interior surface and a second interior surface that are each configured to contact a resected portion of the femur. Additionally, in some case, the first interior surface and the second interior surface are within about 20 degrees of being parallel with each other. Moreover, in some cases, the femoral component is configured such that when the femoral component is seated on the distal portion of the femur, the first interior surface runs at an angle between about 30 degrees and about 55 degrees with respect to a longitudinal axis of the femur. Other implementations are also discussed.

20 Claims, 75 Drawing Sheets

Related U.S. Application Data continuation of application No. 13/831,551, filed on Mar. 14, 2013, now Pat. No. 8,715,357, which is a continuation of application No. 13/802,596, filed on Mar. 13, 2013, now Pat. No. 9,107,769, which is a continuation-in-part of application No. 13/758,855, filed on Feb. 4, 2013, now Pat. No. 9,101,478, which is a continuation of application No. 12/797,372, filed on Jun. 9, 2010, now Pat. No. 8,366,783, which is a continuation-in-part of application No. 12/482,280, filed on Jun. 10, 2009, now Pat. No. 8,382,846, which is a continuation-in-part of application No. 12/198,001, filed on Aug. 25, 2008, now Pat. No. 8,273,133.

(60) Provisional application No. 60/972,191, filed on Sep. 13, 2007, provisional application No. 60/968,246, filed on Aug. 27, 2007.

(51) Int. Cl.
  *A61F 2/30* (2006.01)
  *A61B 17/15* (2006.01)
  *A61B 17/16* (2006.01)

(52) U.S. Cl.
  CPC ........ *A61F 2/3886* (2013.01); *A61F 2/30965* (2013.01); *A61F 2/3877* (2013.01); *A61F 2002/30116* (2013.01); *A61F 2002/30245* (2013.01); *A61F 2002/30604* (2013.01); *A61F 2002/30607* (2013.01); *A61F 2002/30934* (2013.01); *A61F 2002/3863* (2013.01); *A61F 2002/3895* (2013.01); *A61F 2230/0006* (2013.01); *A61F 2230/0071* (2013.01); *A61F 2310/00011* (2013.01); *A61F 2310/00179* (2013.01); *A61F 2310/00329* (2013.01); *A61F 2310/00353* (2013.01)

(56) References Cited

U.S. PATENT DOCUMENTS

| | | |
|---|---|---|
| 4,721,104 A | 1/1988 | Kaufman et al. |
| 4,743,261 A | 5/1988 | Epinette |
| 4,865,606 A | 9/1989 | Rehder |
| 5,133,760 A | 7/1992 | Petersen et al. |
| 5,219,362 A | 6/1993 | Tuke et al. |
| 5,236,461 A | 8/1993 | Forte |
| 5,250,050 A | 10/1993 | Poggie et al. |
| 5,358,527 A | 10/1994 | Forte |
| 5,387,240 A | 2/1995 | Pottenger et al. |
| 5,549,688 A | 8/1996 | Ries et al. |
| 5,728,162 A | 3/1998 | Eckhoff |
| 5,788,916 A | 8/1998 | Caldarise |
| 5,800,438 A | 9/1998 | Tuke et al. |
| 5,824,100 A | 10/1998 | Kester et al. |
| 5,879,389 A | 3/1999 | Koshino |
| 5,925,049 A | 7/1999 | Gustilo et al. |
| 5,964,808 A | 10/1999 | Blaha et al. |
| 6,013,103 A | 1/2000 | Kaufman et al. |
| 6,039,764 A | 3/2000 | Pottenger et al. |
| 6,126,691 A | 10/2000 | Kasra et al. |
| 6,146,424 A | 11/2000 | Gray, Jr. et al. |
| 6,149,687 A | 11/2000 | Gray, Jr. et al. |
| 6,159,217 A | 12/2000 | Robie et al. |
| 6,190,415 B1 | 2/2001 | Cooke et al. |
| 6,206,927 B1 | 3/2001 | Fell et al. |
| 6,319,283 B1 | 11/2001 | Insall et al. |
| 6,402,786 B1 | 6/2002 | Insall et al. |
| 6,491,726 B2 | 12/2002 | Pappas |
| 7,264,635 B2 | 9/2007 | Suguro et al. |
| 7,297,164 B2 | 11/2007 | Johnson et al. |
| 7,326,252 B2 | 2/2008 | Otto et al. |
| 7,615,082 B2 | 11/2009 | Naegerl et al. |
| 7,766,969 B2 | 8/2010 | Justin et al. |
| 8,273,133 B2 | 9/2012 | Samuelson |
| 8,366,783 B2 | 2/2013 | Samuelson et al. |
| 8,382,846 B2 | 2/2013 | Samuelson et al. |
| 8,715,357 B2 | 5/2014 | Samuelson et al. |
| 8,715,360 B2 | 5/2014 | Samuelson et al. |
| 8,715,361 B2 | 5/2014 | Samuelson et al. |
| 8,721,731 B2 | 5/2014 | Samuelson et al. |
| 8,721,732 B2 | 5/2014 | Samuelson et al. |
| 8,784,497 B2 | 7/2014 | Samuelson et al. |
| 9,101,478 B2 | 8/2015 | Samuelson et al. |
| 9,107,769 B2 | 8/2015 | Samuelson et al. |
| 9,265,615 B2 | 2/2016 | Samuelson et al. |
| 9,265,624 B2 | 2/2016 | Samuelson et al. |
| 9,320,616 B2 | 4/2016 | Samuelson et al. |
| 9,326,867 B2 | 5/2016 | Samuelson et al. |
| 9,326,868 B2 | 5/2016 | Samuelson et al. |
| 9,339,391 B2 | 5/2016 | Samuelson et al. |
| 9,427,332 B2 | 8/2016 | Samuelson et al. |
| 2002/0115934 A1 | 8/2002 | Tuke et al. |
| 2003/0100953 A1 | 5/2003 | Rosa et al. |
| 2003/0139817 A1 | 7/2003 | Tuke et al. |
| 2004/0006393 A1 | 1/2004 | Burkinshaw |
| 2004/0078042 A1 | 4/2004 | Masini |
| 2004/0243244 A1 | 12/2004 | Otto et al. |
| 2005/0021147 A1 | 1/2005 | Tarabichi |
| 2005/0096747 A1 | 5/2005 | Tuttle et al. |
| 2005/0143837 A1 | 6/2005 | Ferree |
| 2005/0197710 A1 | 9/2005 | Naegerl |
| 2005/0278034 A1 | 12/2005 | Johnson et al. |
| 2006/0004465 A1 | 1/2006 | Bergin et al. |
| 2007/0135926 A1 | 6/2007 | Walker |
| 2008/0009950 A1 | 1/2008 | Richardson |
| 2008/0058945 A1 | 3/2008 | Hajaj et al. |
| 2008/0140212 A1 | 6/2008 | Metzger et al. |
| 2008/0161918 A1 | 7/2008 | Fankhauser et al. |
| 2008/0243258 A1 | 10/2008 | Sancheti |
| 2009/0043395 A1 | 2/2009 | Hotokebuchi et al. |
| 2009/0082873 A1 | 3/2009 | Hazebrouck et al. |
| 2009/0088861 A1 | 4/2009 | Tuke et al. |
| 2009/0149963 A1 | 6/2009 | Sekel |
| 2009/0326667 A1 | 12/2009 | Williams et al. |
| 2010/0036499 A1 | 2/2010 | Pinskerova |
| 2011/0266265 A1 | 11/2011 | Lang |
| 2012/0209394 A1 | 8/2012 | Bojarski et al. |
| 2013/0024002 A1 | 1/2013 | Samuelson |
| 2013/0204252 A1 | 8/2013 | Samuelson et al. |
| 2014/0142713 A1 | 5/2014 | Wright et al. |
| 2015/0351920 A1 | 12/2015 | Samuelson et al. |
| 2016/0038292 A1 | 2/2016 | Samuelson et al. |
| 2016/0228255 A1 | 8/2016 | Samuelson et al. |
| 2016/0235541 A1 | 8/2016 | Samuelson et al. |
| 2016/0242915 A1 | 8/2016 | Samuelson et al. |
| 2016/0242916 A1 | 8/2016 | Samuelson et al. |
| 2016/0256283 A1 | 9/2016 | Samuelson et al. |

FOREIGN PATENT DOCUMENTS

| | | |
|---|---|---|
| EP | 0 978 261 A1 | 2/2000 |
| GB | 1360485 | 7/1974 |
| JP | H01068257 | 3/1989 |
| JP | H02203854 | 8/1990 |
| JP | H10155824 | 6/1998 |
| JP | 2007509709 | 4/2007 |
| JP | 2007152116 | 6/2007 |
| JP | 2009515610 | 4/2009 |
| WO | WO 94/20047 A1 | 9/1994 |
| WO | WO 96/24311 A1 | 8/1996 |
| WO | WO 98/52499 A1 | 5/1998 |
| WO | WO 2003/099106 A2 | 12/2003 |
| WO | WO 2004/058108 A1 | 7/2004 |
| WO | WO 2004/066882 A1 | 8/2004 |
| WO | WO 2006/092167 A1 | 9/2006 |
| WO | WO 2007/007841 A1 | 1/2007 |
| WO | WO 2007/053905 A1 | 5/2007 |
| WO | WO 2007/119173 A2 | 10/2007 |
| WO | WO 2008/028481 A1 | 3/2008 |
| WO | WO 2009/029631 A1 | 3/2009 |
| WO | WO 2010/144736 A1 | 12/2010 |

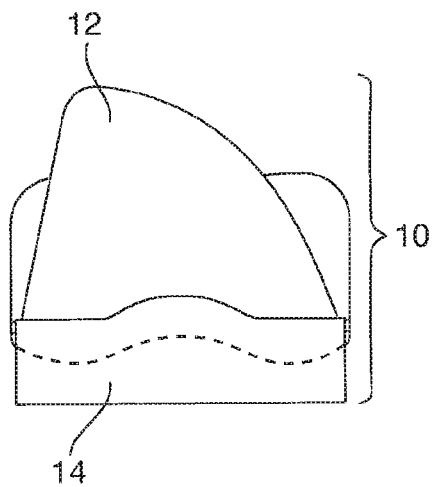
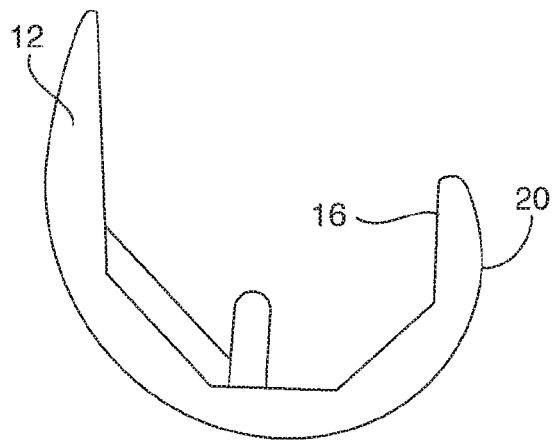
FIG. 3A  FIG. 3B
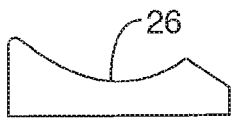
FIG. 3C

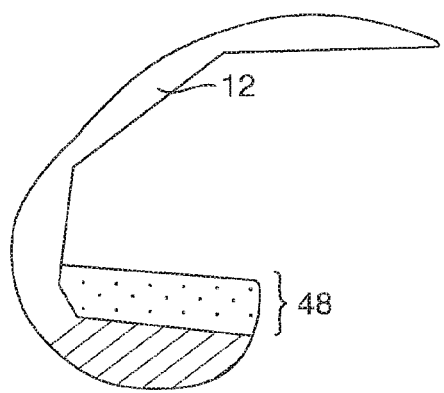
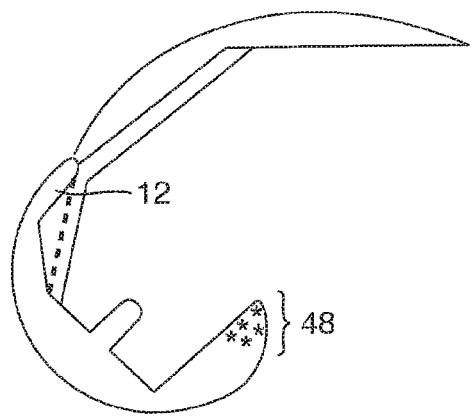
FIG. 15A          FIG. 15B
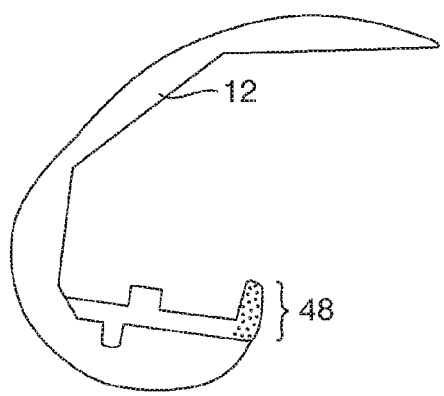
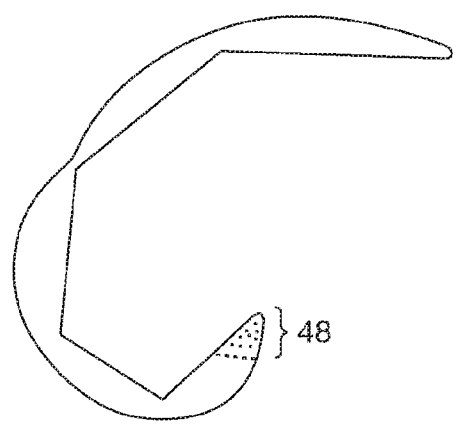
FIG. 15C          FIG. 15D
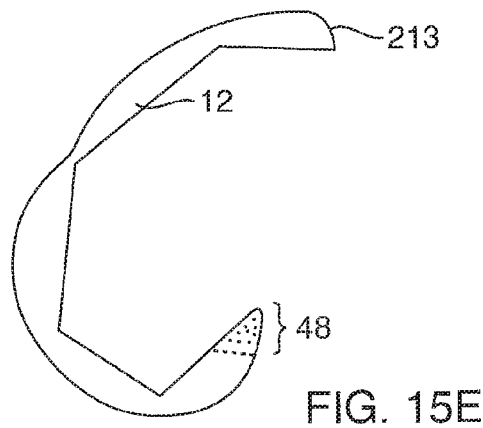
FIG. 15E

SYSTEMS AND METHODS FOR PROVIDING A FEMORAL COMPONENT

RELATED APPLICATIONS

This is a continuation application that claims priority to U.S. patent application Ser. No. 14/270,110, filed May 5, 2014, and entitled SYSTEMS AND METHODS FOR PROVIDING A MODULAR FEMORAL COMPONENT, which is a continuation application that claims priority to U.S. patent application Ser. No. 13/831,551 (now U.S. Pat. No. 8,715,357), filed Mar. 14, 2013, and entitled SYSTEMS AND METHODS FOR PROVIDING A MODULAR FEMORAL COMPONENT, which is a continuation application that claims priority to U.S. patent application Ser. No. 13/802,596 (now U.S. Pat. No. 9,107,769), filed Mar. 13, 2013, and entitled SYSTEMS AND METHODS FOR PROVIDING A FEMORAL COMPONENT, which is a continuation-in-part application of U.S. patent application Ser. No. 13/758,855 (now U.S. Pat. No. 9,101,478), filed Feb. 4, 2013, and entitled SYSTEMS AND METHODS FOR PROVIDING STEM ON A TIBIAL COMPONENT, which is a continuation application of U.S. patent application Ser. No. 12/797,372 (now U.S. Pat. No. 8,366,783), filed Jun. 9, 2010, and entitled SYSTEMS AND METHODS FOR PROVIDING DEEPER KNEE FLEXION CAPABILITIES FOR KNEE PROSTHESIS PATIENTS, which is a continuation-in-part of U.S. patent application Ser. No. 12/482,280 (now U.S. Pat. No. 8,382,846), filed Jun. 10, 2009, and entitled SYSTEMS AND METHODS FOR PROVIDING DEEPER KNEE FLEXION CAPABILITIES FOR KNEE PROSTHESIS PATIENTS, which is a continuation-in-part of U.S. patent application Ser. No. 12/198,001 (now U.S. Pat. No. 8,273,133), filed Aug. 25, 2008, and entitled SYSTEMS AND METHODS FOR PROVIDING DEEPER KNEE FLEXION CAPABILITIES FOR KNEE PROSTHESIS PATIENTS, which claims priority to U.S. Provisional Patent Application Ser. No. 60/968,246, filed Aug. 27, 2007, and entitled SYSTEMS AND METHODS FOR PROVIDING DEEPER KNEE FLEXION CAPABILITIES FOR KNEE PROSTHESIS PATIENTS, and to U.S. Provisional Patent Application Ser. No. 60/972,191, filed Sep. 13, 2007, and entitled SYSTEMS AND METHODS FOR PROVIDING DEEPER KNEE FLEXION CAPABILITIES FOR KNEE PROSTHESIS PATIENTS, all of which are incorporated herein in their entirety by reference.

BACKGROUND OF THE INVENTION

1. Field of the Invention

The present invention relates to knee prostheses. In particular, the present invention relates to systems and methods for providing deeper knee flexion, or full functional flexion capabilities, more physiologic load bearing and improved patellar tracking for knee prosthesis patients. Specifically, these improvements include one or more of the following: (i) adding more articular surface to the antero-proximal posterior condyles of a femoral component, including methods to achieve that result, (ii) modifications to the internal geometry of the femoral component and the associated femoral bone cuts with methods of implantation, (iii) asymmetrical tibial components that have an unique articular surface that allows for deeper knee flexion than has previously been available, (iv) asymmetrical femoral condyles that result in more physiologic loading of the joint and improved patellar tracking, and (v) resection of essentially all of the anterior femoral articular cartilage and underlying bone, but no additional bone and replacing it with a femoral component that does not have an anterior flange as seen on contemporary prostheses.

2. Background and Related Art

Orthopedic surgeons are experiencing a proliferation of knee replacement surgeries. The demand appears driven by the fact that few procedures return as much quality of life as joint replacement.

Moreover, the increased need for knee replacements implicates the need for durable and long lasting artificial knee devices that provide for and allow full, functional flexion. That is, there is a great need for research that provides new medical advances on the overall function and performance of knee prostheses, and improves corresponding surgical materials and technologies related to such devices.

Improvements to knee prostheses correspondingly increase with demand. Thus, currently-available knee prostheses mimic characteristics of the normal knee more than those previously used. Unfortunately, today's knee prostheses still have many shortcomings.

Among the shortcomings is the inability of a knee prosthesis patient to achieve deep knee flexion, also known as full functional flexion. Though some currently available knee prostheses allow for knee flexion (i.e., bending) of more than 130 degrees from full limb extension (zero degrees being when the patient's knee is fully extended and straight); some such prostheses do not allow patients to flex from full extension to 160 degrees and beyond. Full functional or deep knee flexion is where the limb is bent to its maximum extent, which may be with the femur and tibia at an angle to each other of 140 degrees or more, though the actual angle varies from person to person and with body habitus. Full extension is where the leg/limb is straight and the person is in a standing position.

To illustrate the average range in degrees achieved by patients having standard knee prostheses, the following is provided. When a patient's knee or limb is fully extended, the femur and tibia are in the same plane at zero degrees, or up to 5-10 degrees of hyperextension in some individuals. However, once the knee bends, and the distal tibia moves toward the buttocks, the angle increases from zero to 90 degrees for a person sitting in a chair. Furthermore, when the tibia is closest to the femur, and the heel is almost at, if not touching, the buttock, the angle is around 160 degrees or more. Most conventional knee prosthesis patients are unable to consistently achieve the latter position or any position placing the knee joint at angles above 130 degrees (e.g., at 160 degrees and beyond).

For many people, such a limb and body position is not often achieved or desired most of the time. However, nearly everyone, at some point in time, whether or not it occurs when a person is getting on and off the ground to play with children, or merely incidental to those living active lifestyles, finds themselves in a position requiring knee flexion greater than 130 degrees. Unfortunately, those with currently-available knee prostheses are unable to participate in any activity requiring greater knee flexion and are thus limited to watching from the sidelines.

In many populations and cultures such a limb/knee and body position is desired and necessary the majority of the time. For instance, in Asian and Indian cultures, full functional flexion and the squatting position is common and performed for relatively long periods of time.

A need, therefore, exists for knee prostheses for those patients and especially for those in cultures where extensive squatting, sitting with knees fully flexed, and/or kneeling when praying or eating is common, to achieve knee flexion greater than presently possible among those who have currently-available knee prostheses.

Thus, while techniques currently exist that relate to knee prostheses, challenges still exist. Accordingly, it would be an improvement in the art to augment or even replace current techniques with other techniques.

SUMMARY OF THE INVENTION

The present invention relates to knee prostheses. In particular, the present invention relates to systems and methods for providing deeper knee flexion capabilities for knee prosthesis patients, and more particularly by effectuating one or more of the following: (i) providing a greater articular surface area to the femoral component of a knee prosthesis, with either a modification of, or an attachment to the femoral component of a knee prosthesis, which when integrated with a patient's femur and an appropriate tibial component, results in full functional flexion; (ii) providing modifications to the internal geometry of the femoral component and the opposing femoral bone with methods of implanting; (iii) providing asymmetrical under surfaces on the tibial component of the knee prosthesis and uniquely-positioned articular surfaces to facilitate full functional flexion; (iv) asymmetrical femoral condylar surfaces with a lateralized patellar (trochlear) groove to more closely replicate physiologic loading of the knee and to provide better tracking of the patella; and (v) resection of essentially all of the anterior femoral articular cartilage and underlying bone, but no additional bone and replacing it with a femoral component that does not have an anterior flange as seen on contemporary prostheses.

In a normal knee, there is a cessation of active flexion at approximately 120°, first, because the hamstring muscles lose their mechanical advantage, and secondly because the medial femoral condyle rolls posteriorly which does not occur up to 120°. By 120° of flexion, the medial femoral condyle starts to roll backwards relative to the posterior horn of the medial meniscus of the tibia. At 140° of flexion, the femur moves up on to the posterior horn of the medial meniscus. Accordingly, resistance to flexion is felt at this point and beyond. By full flexion, the medial femoral condyle has moved back approximately 8 mm from its position at 120° to a position 10 mm from the posterior tibial cortex. Laterally, the femur moves back an additional 5 mm in hyperflexion so that there is little or no tibiofemoral rotation between 120° and 160°. Accordingly, the hyperflexion between 120° and 160° is a separate arc than the kinematics from 0° to 120° of flexion, and at 160°, the posterior horn of the lateral meniscus comes to lie on the posterior surface of the tibia distal to the femoral condyle. As such, the posterior horn is not compressed and the two bones are in direct contact.

The final limit to hyperflexion arises because the posterior horn of the medial meniscus impedes flexion at 140° and limits it absolutely at 160°. The posterior horn also prevents the medial femoral condyle from moving back beyond a point 10 mm from the posterior tibial cortex. Thus, the posterior horn of the medial meniscus is a key structure in achieving deep flexion.

Implementation of the present invention takes place in association with improved knee prostheses that enable knee prosthesis patients to achieve greater deep knee flexion than previously achievable using presently-designed knee prostheses. In at least some implementations of the present invention, greater deep knee flexion is provided to the knee prosthesis by resecting portions of the femur to allow additional clearance for the posterior horn of the medial meniscus and the tibia. In other implementations in which a portion of the tibia is replaced by a prosthesis, however, the posterior horn is left intact. Additionally, at least some implementations of the present invention further provide positioning and/or installing an articular surface within resected portions of the femur to provide an interface between the posterior horn of the medial meniscus and the resected surface of the femur.

In at least some implementations of the present invention, greater deep knee flexion is provided to the knee prosthesis by providing an articular surface on the proximal, anterior surface (or portion) of the posterior condyles of the femur. At least some implementations of the present invention embrace an additional or increased articular surface on the proximal, anterior portion of either or both of the medial or lateral posterior condyles of the femoral component of the prosthesis. Embodiments of the femoral component add increased articular surface area to the proximal end of the posterior condyles of the femoral component in an anterior direction such that when the patient bends his or her knee during deep knee flexion, contact between the femoral component and the tibial component is maintained, and a greater, deeper knee flexion can be achieved.

In at least some implementations of the present invention, greater deep knee flexion can be provided or improved by modifying the tibial articulation, in which the center of the conforming medial tibial articular surface of the tibial component of the prosthesis is moved posterior relative to what is currently available. Additionally, in some such embodiments, the overall shape of the lateral tibial articular surface is modified.

In at least some implementations of the present invention, greater deep knee flexion can be achieved by providing an asymmetrical femoral component of the prosthesis. The asymmetrical femoral component permits transfer of more than one-half of the force transmitted across the joint to be transmitted to the medial side, as occurs in the normal knee. In some implementations, other modifications to the tibial and femoral components of a knee prosthesis may be made, including having asymmetric femoral condyles, having a closing radius on the femoral component, and removing certain areas of the tibial and femoral components; wherein all of the foregoing result in deeper knee flexion capabilities for knee prosthesis patients than previously achievable.

At least some implementations of the present invention include a femoral component (and associated methods for making and using such a component) that includes a femoral articular surface extending in an anterior direction from a proximal end of a posterior condyle of a femoral knee replacement component, the femoral component further having a full anterior articular extension which replaces the anterior articular cartilage of a femur. In some cases, the femoral component includes a first interior surface and a second interior surface that run substantially parallel to each other. In other cases, the first interior surface and the second interior surface of the femoral component diverge from each other less than a 45° angle. In some instances, the first interior surface and the second interior surface diverge from each other by an angle between approximately 3° and approximately 10°.

While the methods, modifications and components of the present invention have proven to be particularly useful in the area of knee prostheses, those skilled in the art will appreciate that the methods, modifications and components can be used in a variety of different orthopedic and medical applications.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which:

FIGS. 2A-2C and 3A-3C depict various views of a generic knee prosthesis;

FIG. 6I illustrates an alternate embodiment of a representative tibial component modified to include the raised ridge articulation feature;

FIG. 8A illustrates a conventional femoral component while

FIGS. 15A-15E illustrate comparisons between embodiments of a femoral component;

DETAILED DESCRIPTION OF THE INVENTION

The present invention relates to knee prostheses. In particular, the present invention relates to systems and methods for providing deeper knee flexion capabilities for knee prosthesis patients, and more particularly, to: (i) providing an extended articular surface on the proximal, anterior surface (or portion) of the posterior condyles of the femur; (ii) making modifications to the internal geometry of the femoral component and the associated femoral bone cuts with methods of implantation; (iii) making modifications to the tibial and femoral components of a knee prosthesis, including asymmetrical tibial articular surfaces and removing certain areas of the tibial and femoral components; (iv) having asymmetric femoral condyles, including the option of having a closing radius on the femoral component, wherein all of the foregoing result in deeper knee flexion capabilities for knee prosthesis patients than previously achievable; and (v) resection of essentially all of the anterior femoral articular cartilage and underlying bone, but no additional bone and replacing it with a femoral component that does not have an anterior flange as seen on contemporary prostheses.

It is emphasized that the present invention, as illustrated in the figures and description herein, may be embodied in other forms. Thus, neither the drawings nor the following more detailed description of the various embodiments of the system and method of the present invention limit the scope of the invention. The drawings and detailed description are merely representative of examples of embodiments of the invention; the substantive scope of the present invention is limited only by the appended claims recited to describe the many embodiments. The various embodiments of the invention will best be understood by reference to the drawings, wherein like elements are designated by like alphanumeric character throughout.

Figure 1A:
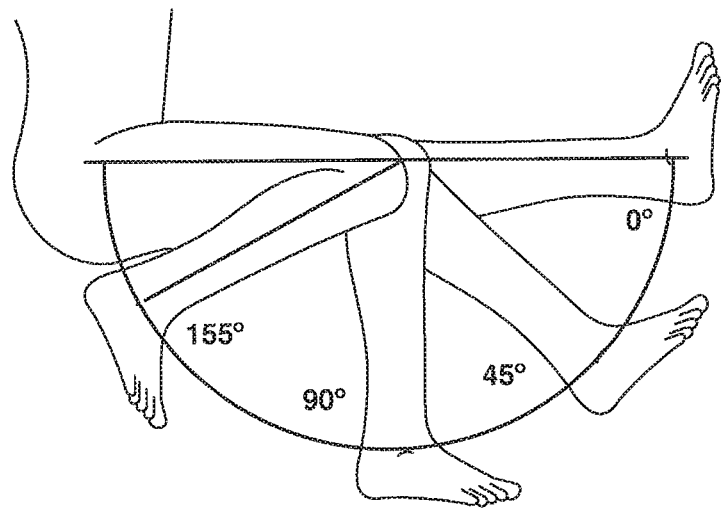
FIGS. 1A and 1B depict ranges of flexion of a knee joint.
Figure 1B:
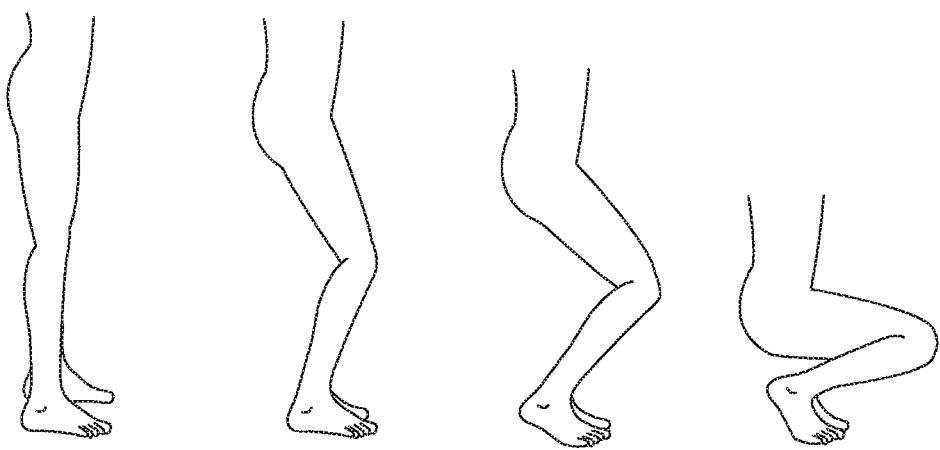

With reference now to the accompanying drawings, FIGS. 1A-3C are provided for general reference to assist in understanding the features of the embodiments of the present invention. FIGS. 1A and 1B depict a range of angles possible between the tibia and femur in a person who is extending and flexing (bending) his or her knee. Specifically, FIG. 1A depicts a range of angles possible while the person extends and bends his or her knee, realizing that some knees may flex to 160 degrees, 165 degrees, or beyond. FIG. 1B depicts these various angles in an alternative position. These figures should be kept in mind during the discussion illustrating how with the embodiments of the present invention, knee flexion of greater than 135 degrees is possible for knee prosthetic patients, which is not generally possible with currently-available knee prostheses.

Figure 2A:
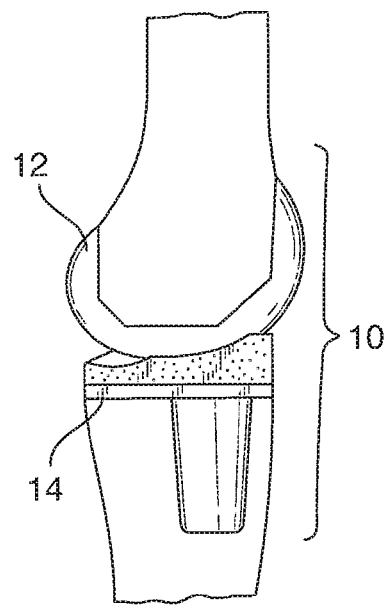
Figure 2B:
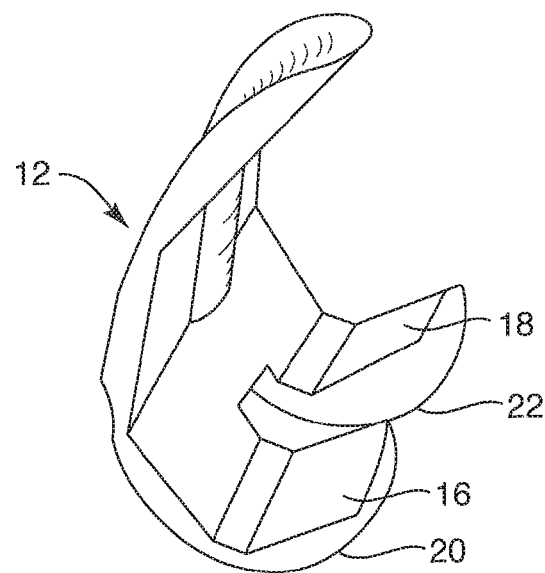
Figure 2C:
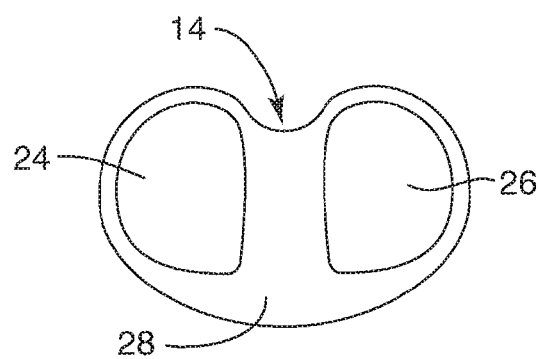

FIGS. 2A-2C depict various perspective views of a generic knee prosthesis 10. Specifically, FIG. 2A depicts a sagittal view of a left knee joint having a knee joint prosthesis 10, with the tibia and the femur of the normal knee transparent. FIG. 2B depicts an enlarged view of a femoral component 12 of the knee prosthesis 10, while FIG. 2C provides a top perspective view of a tibial component 14 of the knee prosthesis. FIG. 2B depicts certain components of the femoral component 12, such a medial receiving area 16 that may be modified in embodiments of the present invention to integrally connect with an attachment (not shown but hereinafter described) as well as a lateral receiving area 18. The internal geometry of the femoral component 12 is provided to allow a one piece femoral component 12 that is rolled into place on the resectioned femur 32, as shown in FIG. 4D. Thus, the internal geometry of the femoral component 12 includes various surfaces, including areas 16 and 18, to accommodate the patellar articulation and the anterior extensions of the proximal portions of the posterior condyles. The resectioned portions of the condyles provide flat surfaces which are loaded in compression in full knee flexion. Additionally, the resectioned surfaces are provided such that the articular surface of the femoral component is at essentially the same position as the surface being resectioned. As such, the normal relationship between the femur and the tibia is preserved with full flexion. Additionally, when the knee is fully flexed, the interface between the femoral component and the underlying femur is mainly loaded in compression rather than sheer forces. Compression forces provide a more stable interface between the femoral component and the femur thereby decreasing the chances of loosening. Therefore, in some embodiments the interface between the femoral component and the tibial component are configured to enhance a compression force between the femoral component and the underlying femur during full flexion of the knee joint.

Also visible in FIG. 2B is a medial femoral condylar surface 20 and a lateral femoral condylar surface 22. FIG. 2C depicts the tibial component 14 and its elements: a lateral tibial condylar surface 24, a medial tibial condylar surface 26, and an intercondylar surface 28. When the knee prosthesis 10 is functioning, an interface exists between the medial femoral condylar surface 20 of the femoral component 12 and the medial tibial condylar surface 26 of the tibial component 14 and between the lateral femoral condylar surface 22 of the femoral component 12 and the lateral tibial condylar surface 24 of the tibial component 14.

FIGS. 3A-3C depict additional perspective views of the generic knee prosthesis 10 with its different components. Specifically, FIG. 3A depicts a frontal view of the knee prosthesis 10 with the femoral component 12 articulating with the tibial component 14 as described above. FIG. 3B is a side view of the femoral component 12, and FIG. 3C is a side view of the tibial component 14, and specifically, of the medial side of the tibial component showing the medial tibial condylar surface 26. The medial femoral condylar surface 20 slidingly interfaces with the medial tibial condylar surface 26 so that as a person flexes or extends his or her knee, the arc of the medial femoral condylar surface 20 runs along the media tibial condylar surface 26.

In some embodiments of the present invention, greater deep knee flexion is provided to the knee prosthesis 10 by providing an articular surface on the proximal, anterior surface (or portion) of the posterior condyles of the femur. At least some embodiments of the present invention embrace an additional or increased articular surface on the proximal, anterior portion of either or both of the medial or lateral posterior condyles of the femoral component 12. Embodiments of the femoral component 12 add increased articular surface area to the proximal end of the posterior condyles of the femoral component 12 in an anterior direction such that when the patient bends his or her knee during deep knee flexion, contact between the femoral component 12 and the tibial component 14 is maintained, and a greater, deeper knee flexion can be achieved.

Four different examples of how this may be achieved are demonstrated with reference to the Figures. Any method of increasing an articular surface area to the proximal end of the posterior condyles of the femoral component 12 in an anterior direction is embraced by the embodiments of the present invention.

Figure 8B:
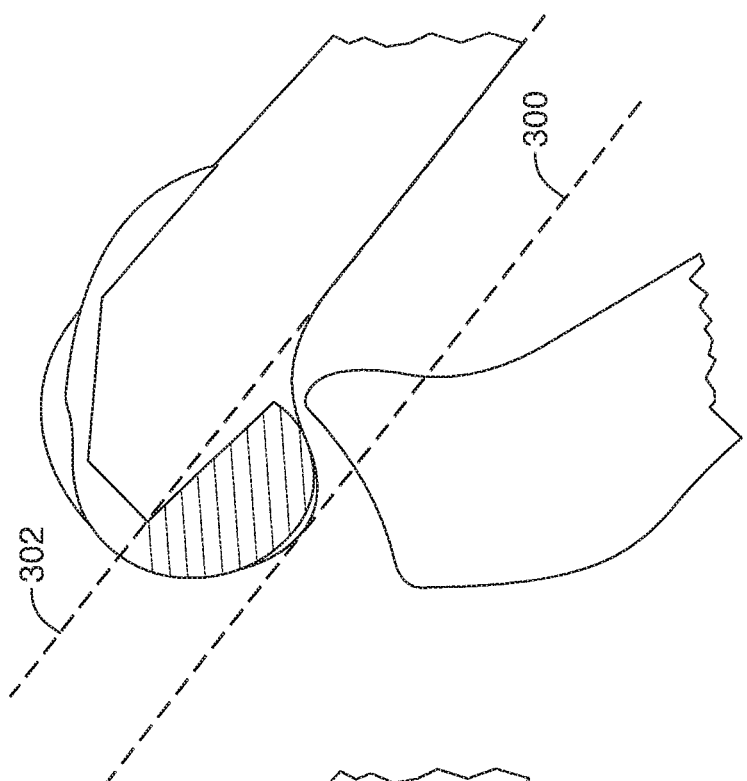
FIG. 8B illustrates an embodiment of a femoral component in accordance with the present invention.
Figure 8A:
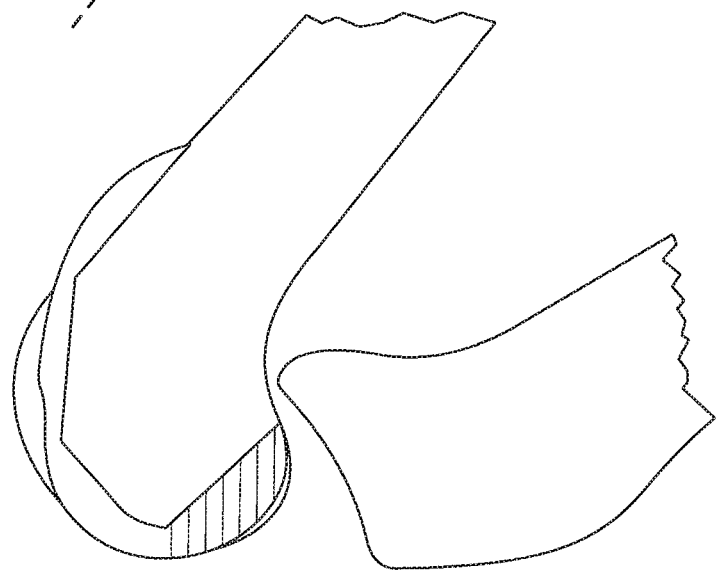

FIGS. 8A and 8B illustrate a femoral component 12 and method of increasing an articular surface area to the proximal end of the posterior condyles of the femoral component 12. FIG. 8A illustrates a side view of a conventional femoral component 12. In the first embodiment of the inventive prosthesis, the shaded area of the femoral component 12 of FIG. 8A (i.e., the posterior condyle) is thickened in the anterior direction until the resulting surface opposing the bone is approaching the same plane as the posterior surface of the shaft of the distal femur. This thickening may be seen with reference to FIG. 8B. In particular, FIG. 8B shows that, in some embodiments, the posterior condyle is thickened from its posterior most edge (as illustrated by line 300) towards a plane 302 of a distal portion of posterior surface of the shaft of the distal femur. This results in a greater articular surface area of the posterior condyles of the femoral component 12. This requires resection of more bone but is otherwise an easy modification to current prostheses and requires little to no modification of current surgical technique.

A second type of embodiment that extends the articular surface area is illustrated by FIGS. 4A-5C. Methods of utilizing this type of embodiment are illustrated with reference to FIGS. 9-10H. This type of embodiment utilizes an extension attachment to the femoral component 12 of an embodiment of the knee prosthesis 10, which when integrated with both the femoral component 12 and a patient's femur, results in a greater surface area of the femoral component 12.

As illustrated in FIGS. 4A-5D, this type of embodiment has a modular attachment 30 that provides a modular flexion attachment surface to extend the articular surface area of the anterior portion of the proximal portion of the posterior condyles. The modular attachment 30 may be attached to the inside, or non-articular surface, of a relatively conventional total knee femoral component 12. The modular attachment 30 has a portion that may be partially received, in one embodiment, within a recessed receiving area on the flat anterior surface of one or both of the posterior condyles of the femoral component 12 and may thus be used on the medial posterior condyle, the lateral posterior condyle, or both. Alternatively, it may be implanted in a groove within either or both of the resected posterior condyles of the femur itself.

The modular attachment 30 provides an increased articular contact area as an anterior continuation of the medial femoral condylar surface 20 and/or of the lateral femoral condylar surface 22 of the femoral component 12. In some embodiments, the modular attachment 30 may be initially placed onto the femoral component 12 and then attached to the distal end of the patient's femur. In other embodiments, the modular attachment 30 may be connected first to the posterior condyles of the distal end of the femur and then integrally connected with the femoral component 12. The modular attachment 30 may be used on the medial side, on the lateral side or on both sides.

Figure 4A:
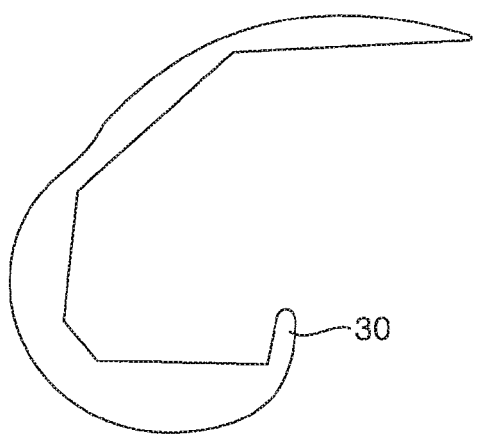
FIGS. 4A-4D depict representative perspective views of embodiments of a femoral component of a knee prosthesis in accordance with embodiments of the present invention.
Figure 4B:
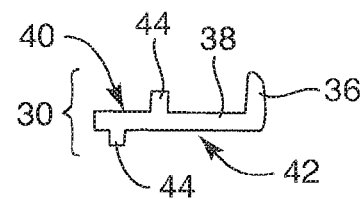
Figure 4C:
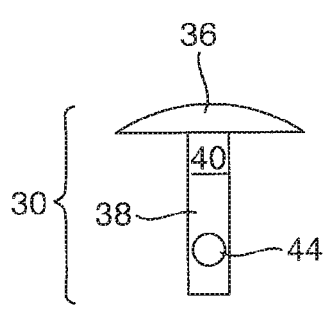
Figure 4D:
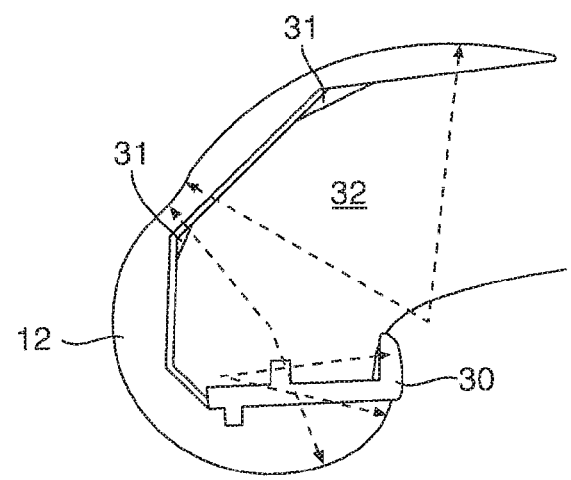

FIGS. 4A-4D depict perspective views of embodiments of the femoral component 12 and the modular attachment 30. As described, the modular attachment 30 attaches to the femoral component 12 and to the femur of a patient to enlarge the surface area of the femoral component 12 and, ultimately, to enable deep knee flexion beyond 140 degrees in a knee prosthesis patient. FIG. 4A depicts a simplified side view of an embodiment of the femoral component 12 having the modular attachment 30 attached to the posterior condyle of the femoral component. FIG. 4D depicts a side view of the attachment integrally attached to a patient's femur and to the femoral component of the knee prosthesis. The modular attachment 30 may be modular as shown in FIGS. 4B-4D and may fit within a recess in either or both of the medial receiving area 16 and the lateral receiving area 18 (i.e., in the anterior interior surface of the posterior condyles of the femoral component 12, as shown in FIG. 2B) and/or in either or both of the medial and the lateral posterior condyles of the femur or in both the femoral component 12 and the femur. In another embodiment the modular attachment 30 may be a permanent part of the femoral component, as discussed below.

FIG. 4B depicts a side view of one embodiment the modular attachment 30 and FIG. 4C depicts a top view of the depicted embodiment of the modular attachment 30. Specific dimensions of the depicted embodiment of the modular attachment 30 are not given and one of skill in the art will recognize that the dimensions may be modified from patient to patient and will also recognize that the various portions of the modular attachment 30 may all be formed in some embodiments to be as wide as the condyle of the femoral component 12.

In some embodiments, the modular attachment 30 includes a first portion roughly perpendicular to a second portion. The first portion of the modular attachment 30 entails a flanged articular area 36 ("flanged area 36") at one end of the modular attachment 30, and an elongated stem 38 extending therefrom, which extends roughly perpendicular from the flanged area, distally from the flanged area 36. The elongated stem 38 therefore is attached to the non-articular side of the flanged area 36. Although the elongated stem is illustrated in FIG. 4C as having a medial-lateral width substantially shorter than the medial-lateral width of the flanged area 36, the elongated stem 38 of other embodiments may be of any medial-lateral width up to the medial-lateral width of the posterior condyles of the femoral component 12 itself.

The elongated stem 38 has an upper side 40 and a lower side 42. Nodules 44 may be placed on either or both of the upper side 40 and the lower side 42, to enable an integral connection with the femur 32 on the upper side 40, and the femoral component 12 on the lower side 42. Some form of a nodule-receiving groove or recess (not shown) may be made in the femur 32 and/or the femoral component 12 to receive these nodules 44 and to secure the integral connection between the femur 32, the attachment 30, and the femoral component 12; with the modular attachment 30 being disposed between the femur 32 and the femoral component 12.

In embodiments having no nodules 44 on the elongated stem 38, the attachment 30 may fit within a recess made on either or both of the medial receiving area 16 and the lateral receiving area 18 of the femoral component 12. The elongated stem 38 of the modular attachment 30 would fit within such recesses and integrally connect thereto. The modular attachment 30 may simultaneously connect with the femur 32 on the upper side 40 (generally) of the elongated stem 38. In embodiments having no nodules on the elongated stem, the stem of the modular portion may further fit into a groove prepared in the resected posterior condyles of the femur.

The modular attachment 30 increases the overall surface area of the femoral component 12 and prolongs the interface and contact that exists between the femoral component 12 and the tibial component 14. This enables greater knee flexion in prosthetic knee patients because the femoral component 12 remains interfaced with the tibial component 14 throughout the full range of flexion resulting in pain-free knee flexion.

Without this increased surface area, the medial and lateral proximal edges of the posterior femoral condyles of a prosthesis may push into the proximal surfaces of the tibial component 14 and may produce wear of the tibial component 14. In addition, the tibial component 14 may contact the bone of the distal femur 32 that is anterior and/or proximal to the proximal edges of the posterior condyles of the prosthesis and cause pain to and limit flexion of the prosthetic knee patient and may cause wear to the tibial component. Further, without this added surface area, with flexion beyond 140 degrees, the tibial component 14 may exert a force in the distal direction on the femoral component 12, which may result in loosening of the femoral component 12. Therefore, the modular attachment 30 extends the life of the prosthetic knee, decreases pain to the patient, and ultimately, enables a prosthetic knee patient to achieve deep knee or full functional flexion.

Figure 5B:
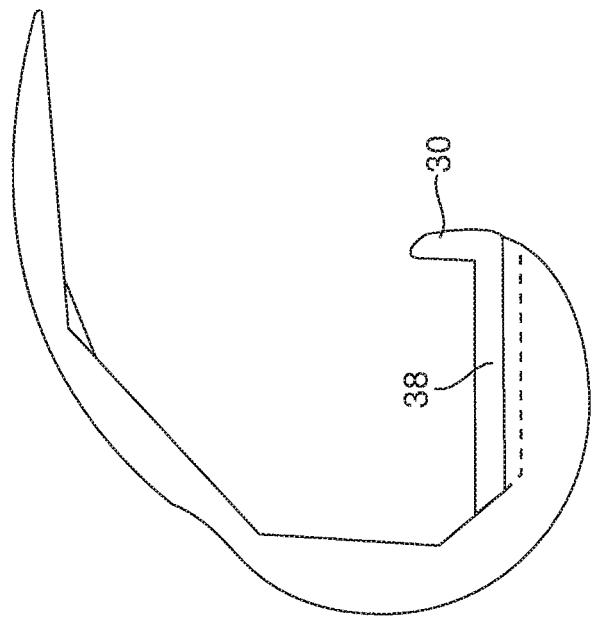
FIGS. 5A-5D depict representative perspective views of embodiments of a femoral component of a knee prosthesis in accordance with embodiments of the present invention.
Figure 5A:
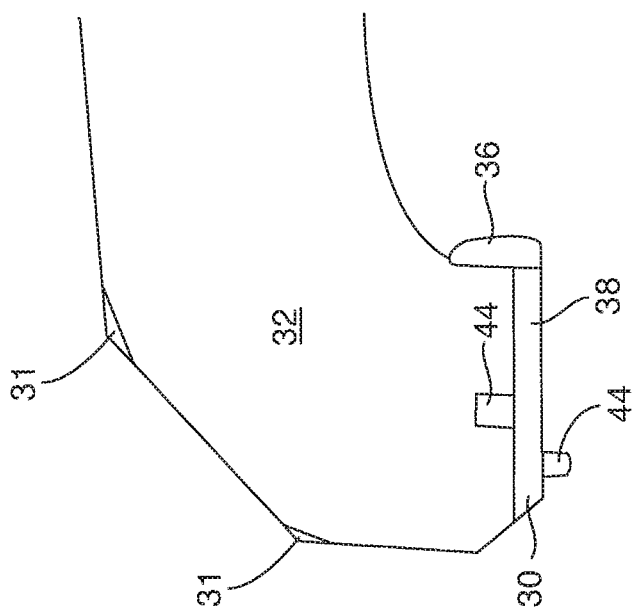
Figure 5D:
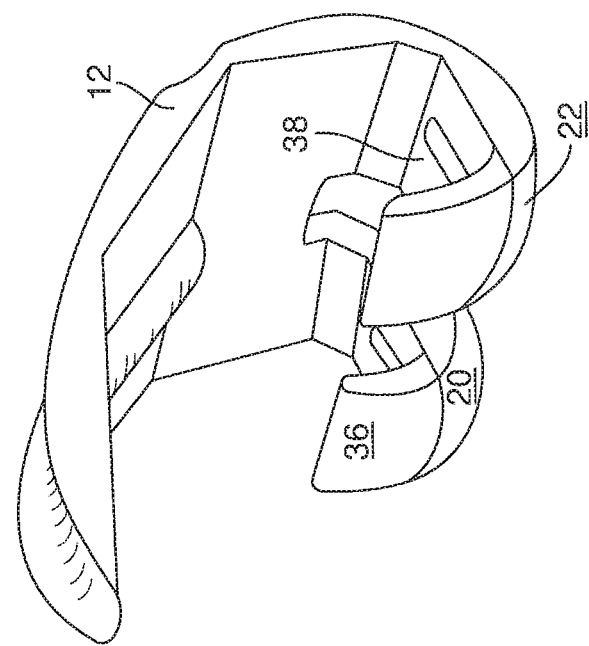
Figure 5C:
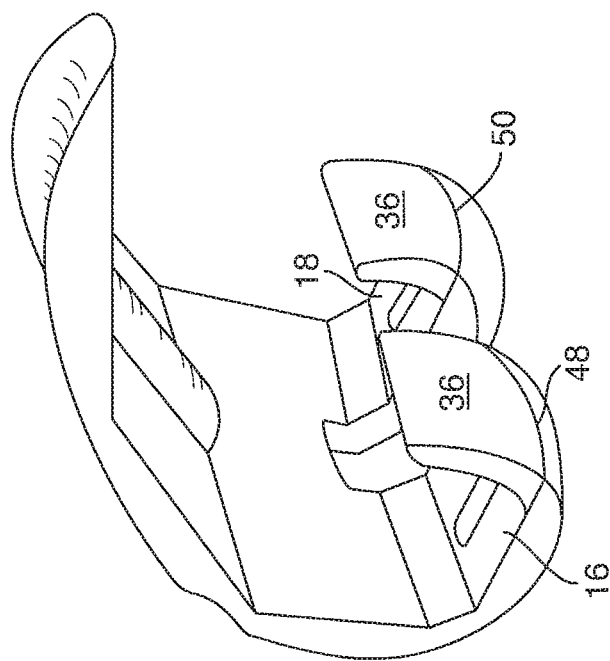

FIGS. 5A-5D depict various perspective views of the modular attachment 30 as it is attached to the femoral component 12 and to the femur 32. FIG. 5A is illustrative of the modular attachment 30 as it is attached to the femur 32 prior to attachment of the femoral component 12. FIGS. 5B-5D are illustrative of the modular attachment 30 as it is recessed within the femoral component 12 prior to attachment to the femur 32, and specifically, as the modular attachment 30 is integrally connected to either or both of the medial femoral receiving area 16 and the lateral femoral receiving areas 18.

Figure 9:
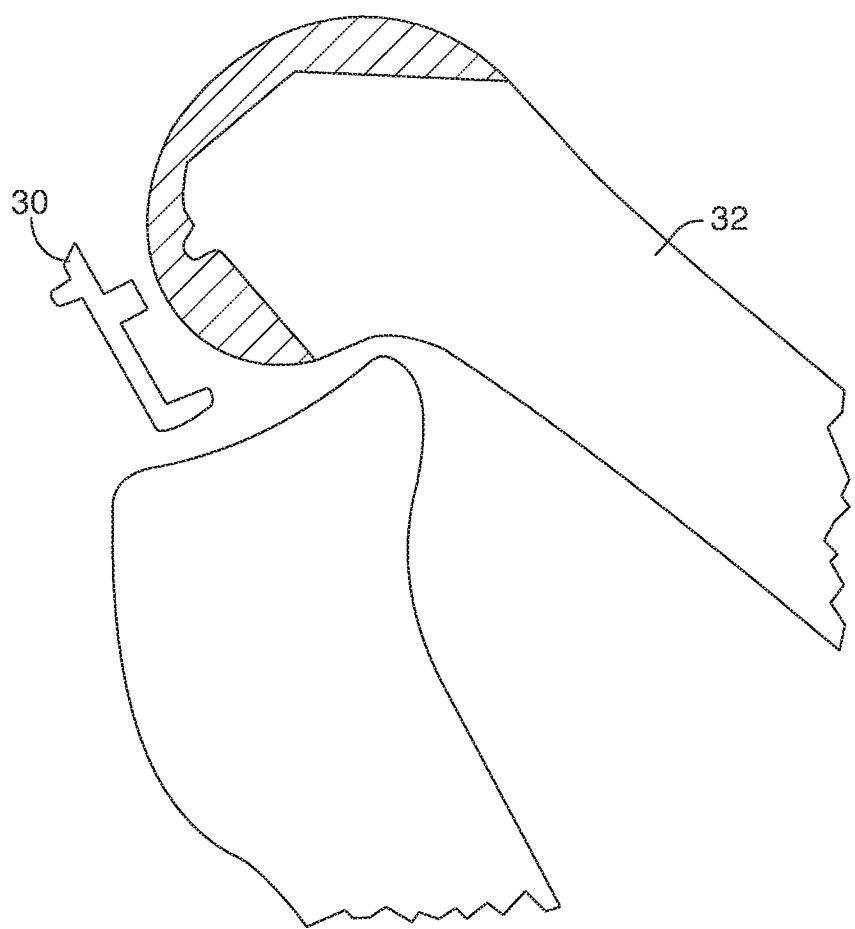
FIG. 9 illustrates a modular attachment for use with embodiments of a femoral component in accordance with embodiments of the present invention.
Figure 10A:
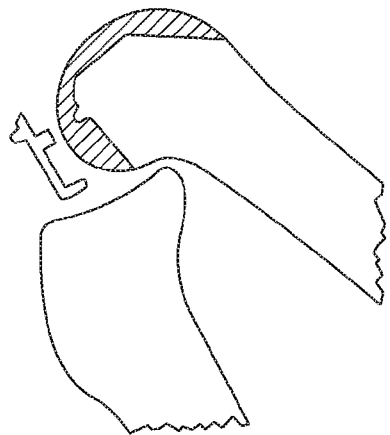
FIGS. 10A-10H illustrate representative steps for attaching an embodiment of a femoral component to a femur, the resectioned portions of the femur shown in phantom.
Figure 10B:
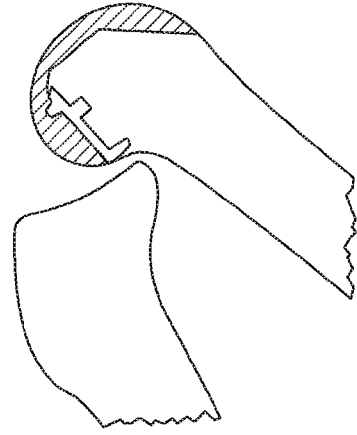
Figure 10C:
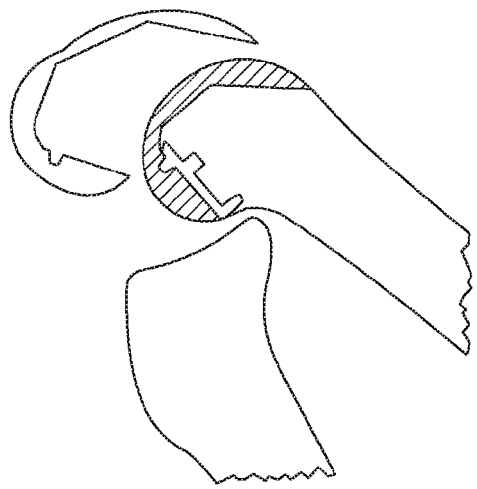
Figure 10D:
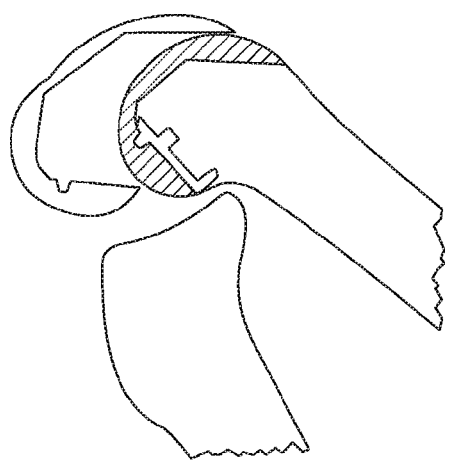
Figure 10E:
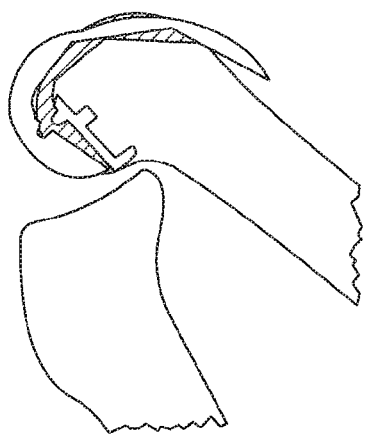
Figure 10F:
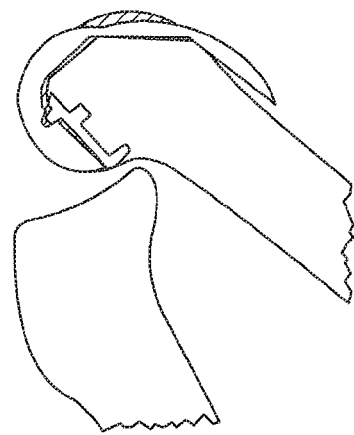
Figure 10G:
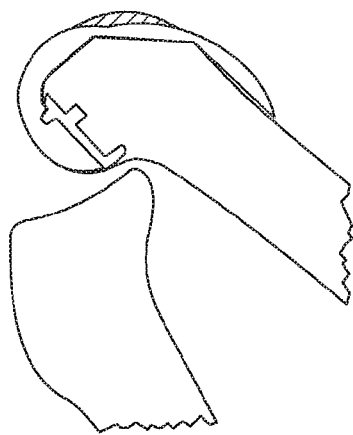
Figure 10H:
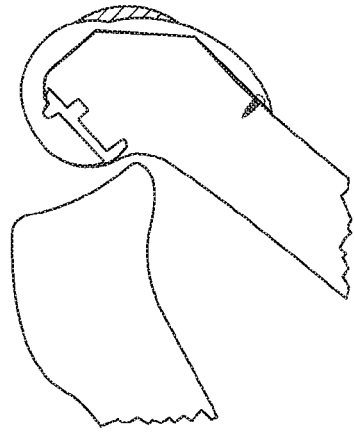

FIG. 9 and FIGS. 10A-10H illustrate methods of attaching the modular attachment 30 to the femur 32, followed by attaching the femoral component 12 to the femur 32 and modular attachment 30. FIG. 9 illustrates the resection needed on the femur 32 prior to creating the recess in the femur to allow attaching the modular attachment 30. FIG. 9 and FIGS. 10A-10H do not illustrate the specific resection needed for the modular attachment 30, but the resection needed will be appreciated by one of skill in the art. After resection is completed, as at FIG. 10A, the modular attachment 30 may be attached to the femur as at FIG. 10B. The femoral component 12 may then be attached to the femur 32 (and to the modular attachment 30, if desired) by positioning and moving the femoral component 12 as illustrated in FIGS. 10C-10H. As may be appreciated from the sequence of illustrations depicted in FIGS. 10C-10H, the femoral component 12 needs to be rotated or rolled into position, with initial contact beginning in the posterior region as illustrated in FIG. 10E and progressing to the fully-seated position illustrated in FIG. 10G. This is a new implantation technique that will require some additional practice and training over current techniques.

Figure 11A:
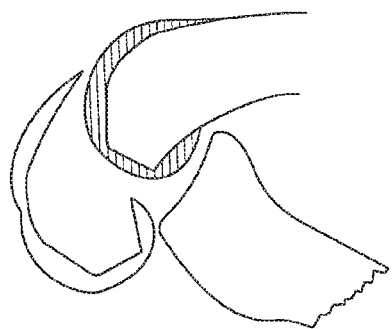
FIGS. 11A-11K illustrate representative steps for attaching an alternate embodiment of a femoral component to a femur.
Figure 11B:
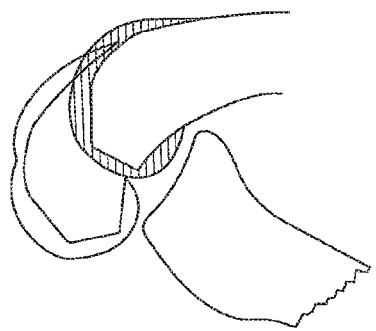
Figure 11C:
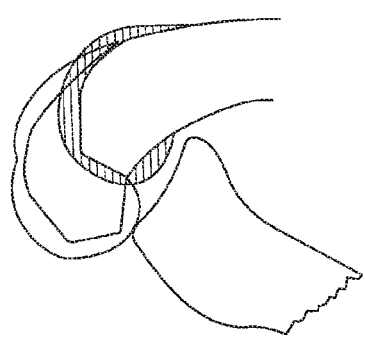
Figure 11D:
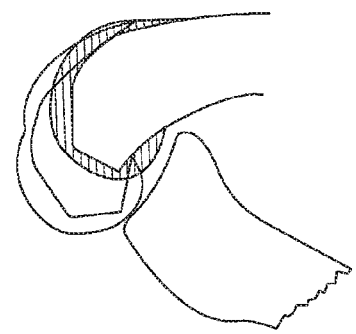
Figure 11E:
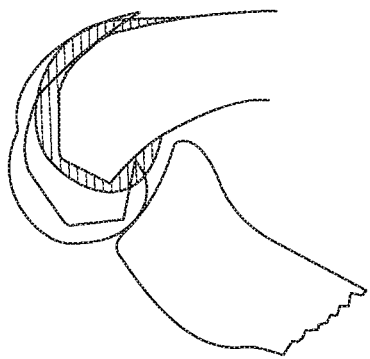
Figure 11F:
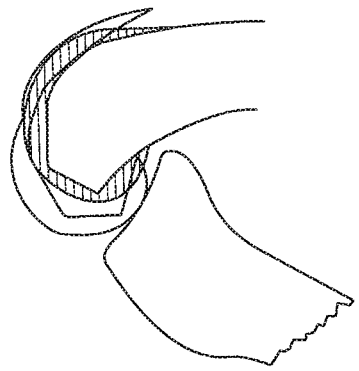
Figure 11G:
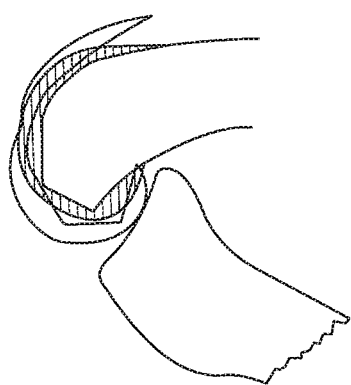
Figure 11H:
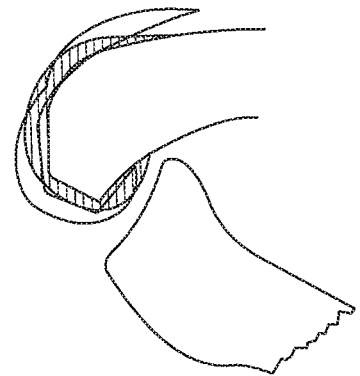
Figure 11I:
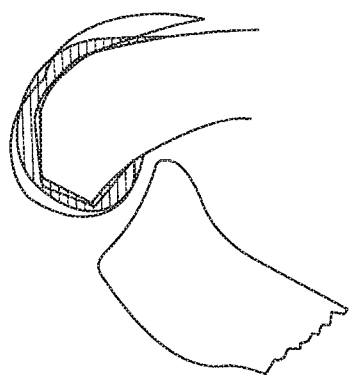
Figure 11J:
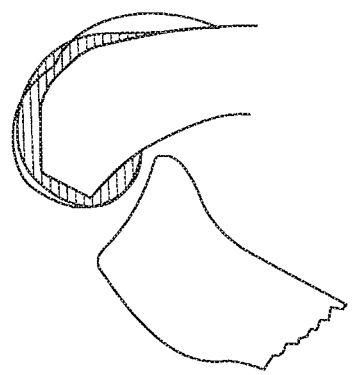
Figure 11K:
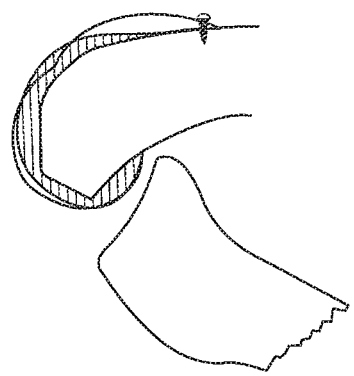

As has been set forth above in reference to FIG. 4A, a third type of embodiment having an extended articular surface is not modular and does not utilize a separate modular attachment 30. In such embodiments, an extended articular surface corresponding to the flanged area 36 of the modular attachment 30 may be integrally formed as part of one or both condyles of the femoral component 12. Placement of one such embodiment is illustrated with reference to FIGS. 11A-11K. As may be appreciated with reference to these Figures, placement of such an embodiment also utilizes a similar rotational placement technique to that illustrated in FIGS. 10C-10H. As may be appreciated by reference to FIGS. 10H and 11K, any of the modular or non-modular embodiments may, optionally, be further secured by one or more screws placed in an anterior flange of the femoral component 12.

Figure 12B:
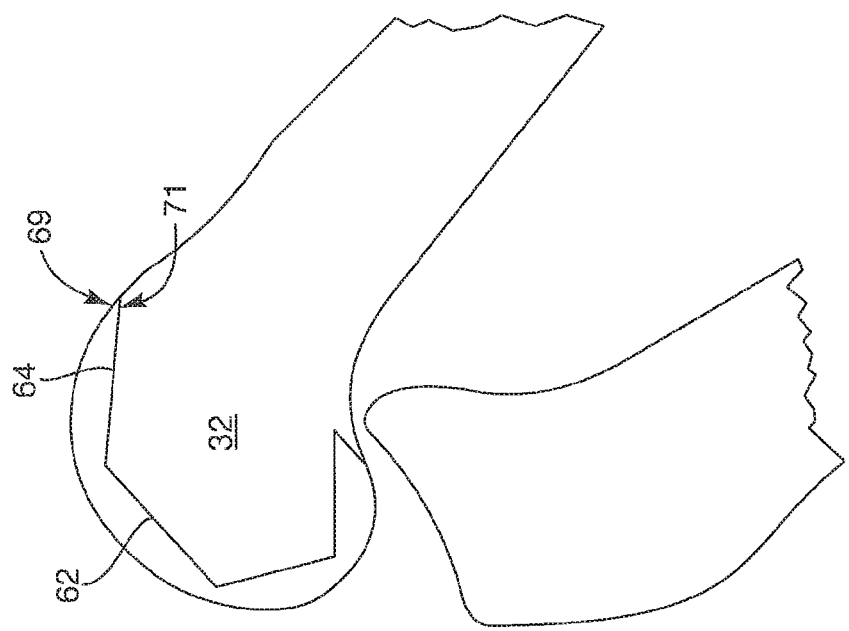
FIGS. 12A-12C and FIG. 13 illustrate comparisons between a conventional femoral component and some embodiments of a femoral component in accordance with embodiments of the present invention.
Figure 12A:
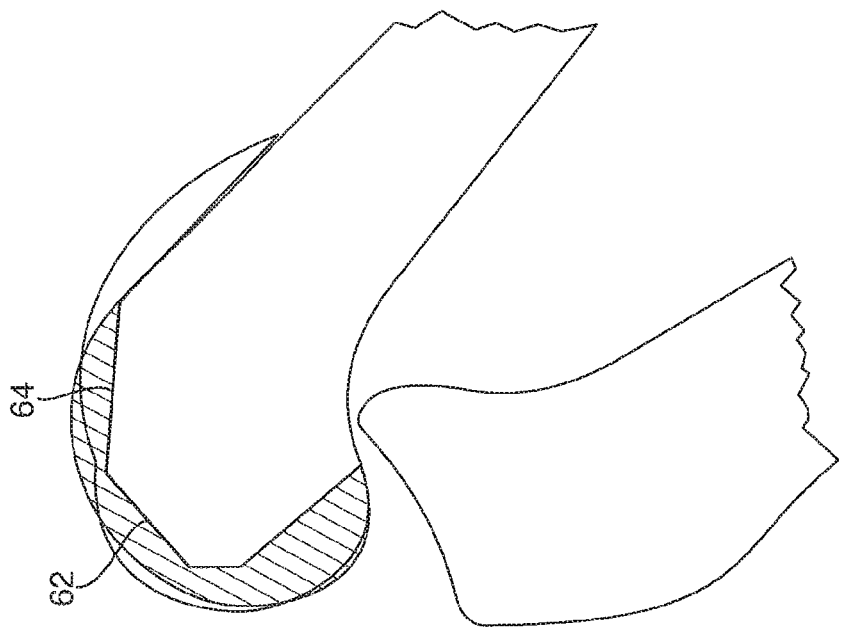
Figure 12C:
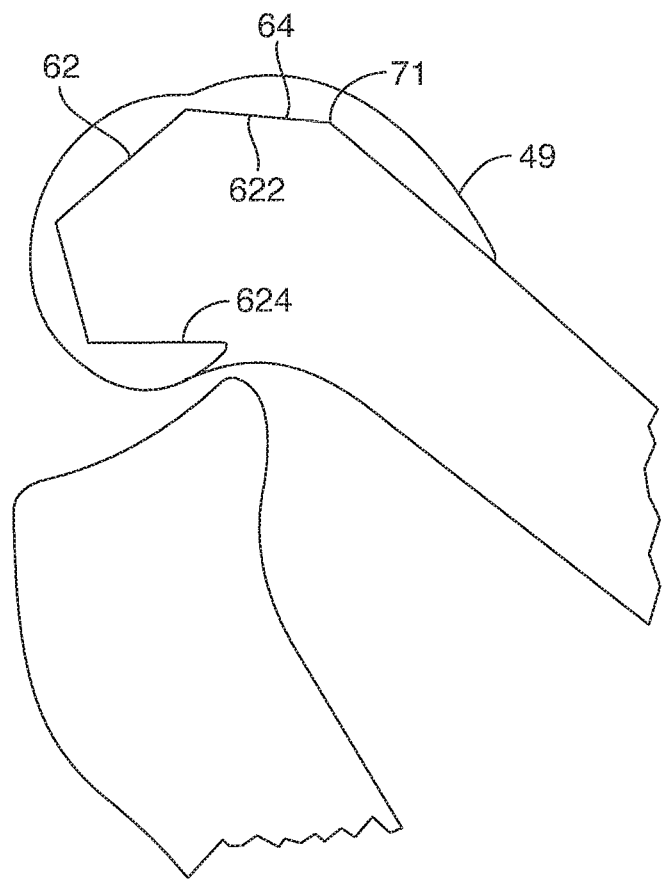
Figure 13:
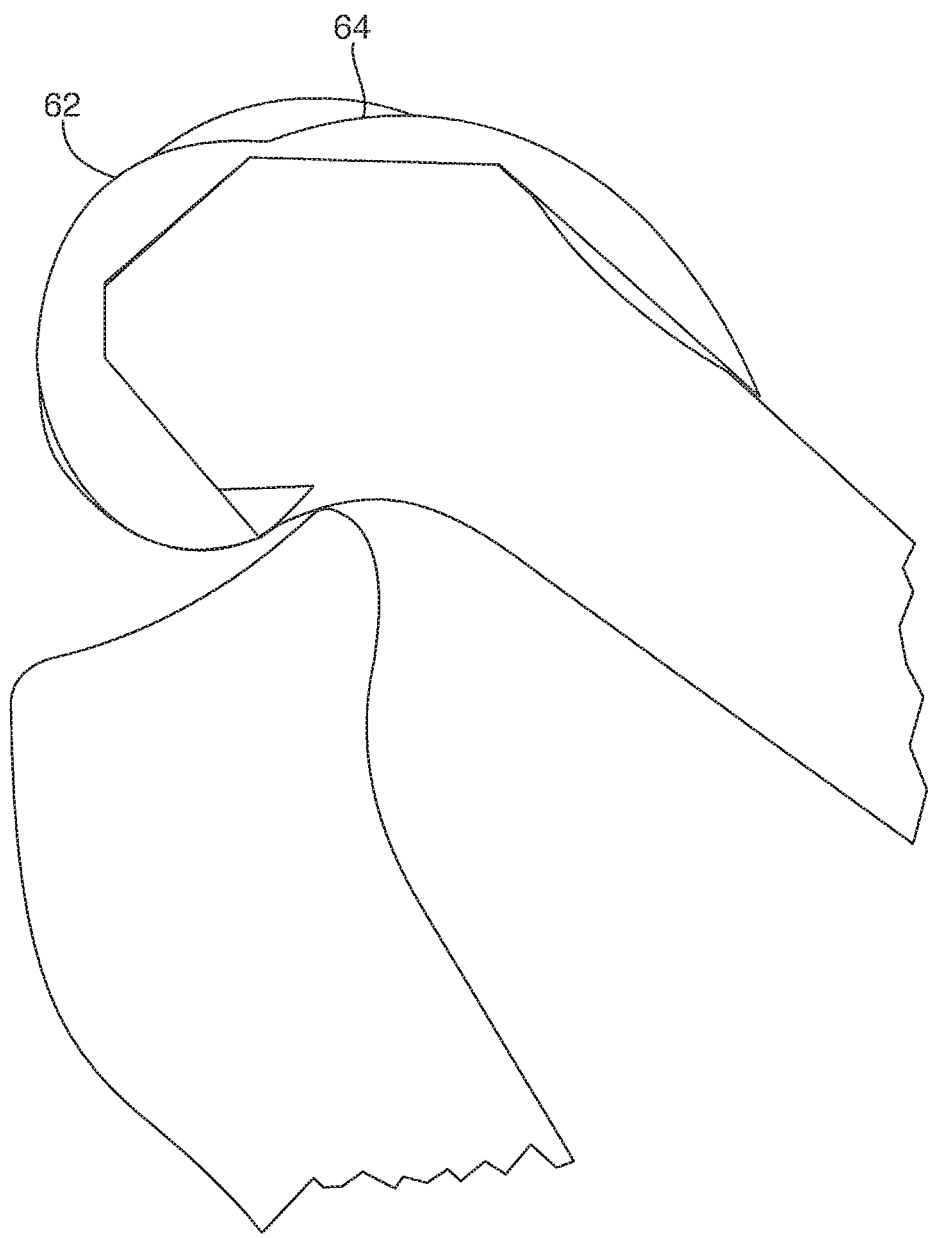

One advantage of the embodiment illustrated in FIGS. 11A-11K is that the implanting surgeon may decide whether to utilize the illustrated embodiment or a traditional femoral component 12 after the distal and anterior oblique cuts have been made. This is illustrated in FIGS. 12A through 12C. FIG. 12A shows a traditional femoral component 12. FIG. 12B shows an embodiment of the described femoral component 12 without an extended anterior flange. In other words, FIG. 12B shows that, in some embodiments, when the femoral component is seated on the femur 32, a proximal anterior end 69 of the femoral component is configured to terminate at or near a proximal end 71 of the anterior oblique cut 64 (e.g., at between about 0 and about 15 mm on either the proximal side or the distal side of the proximal limit of the knee's natural articular cartilage). FIG. 12C, on the other hand, shows an embodiment of the femoral component 12 illustrated in FIGS. 11A-11K, which include an anterior flange 49 that extends proximally past the anterior oblique cut 64. As may be appreciated by reference to the Figures, the distal cuts 62 and anterior oblique cuts 64 are essentially identical. This may be further appreciated by reference to FIG. 13, which shows a superimposed view of FIGS. 12A and 12B, not only showing that the distal femoral cuts 62 and the anterior oblique cuts 64 are identical, but also showing that the total amount of bone resected for the illustrated embodiment is similar to or less than the amount resected using current techniques and femoral components 12.

In a non-modular embodiment of the femoral component 12 as shown in FIGS. 11A-11K and in a modular embodiment of the femoral component as shown in FIGS. 4A-5D, there are junctions where the inside flat surfaces of the prosthesis (which when implanted are in contact with the bone) meet. These flat surfaces, rather than coming together at a sharp angle, may or may not have a radius connecting the two flat surfaces. Not all of the junctions of the flat surfaces necessarily need a radius and in some embodiments none of the junctions of flat surfaces will have radii. The flat surfaces may or may not be in exactly the same planes as on conventional knees and will provide for the placement of a non-modular surface that will provide an articulation for the proximal, anterior portion of the posterior femoral condyles extending to or almost to a plane that is a continuation of the posterior cortex of the distal femoral shaft. In embodiments where one or more radii are provided to the junction(s) of the inside flat surfaces of the femoral component 12, corresponding radii 31 or curvatures may be provided to the resected bone surface of the femur, as is illustrated in FIG. 5A. As may be appreciated by one of skill in the art, the presence of the corresponding radii 31 may assist in the rotational placement of the femoral component 12 as illustrated in FIGS. 10A-10H and 11A-11K.

This internal configuration allows the femoral component 12 to be initially applied to the femur in a flexed position and then rotated into the fully extended position as it is implanted fully, as illustrated and discussed with reference to FIGS. 10A-10H and 11A-11K. Screw(s) may, optionally, be placed in the anterior flange (or other portion) of the femoral component 12 to firmly stabilize the component. This ability facilitates implanting the non-modular femoral component 12 or a modular femoral component 12 with the modular attachment 30 already implanted on the posterior condyles of the femur 32.

Figure 14:
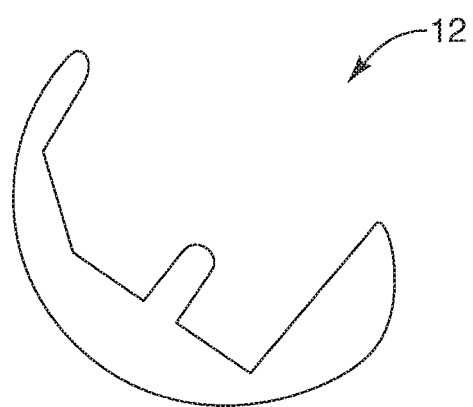
FIG. 14 illustrates an alternate embodiment of a femoral component in accordance with embodiments of the present invention.

A fourth type of embodiment of the femoral component 12 is illustrated in FIG. 14. This type of embodiment has a femoral component 12 that replaces the weight-bearing distal femoral condyles, and some or all of the anterior femoral articular surface and, in addition to some or all of the articular surface of the posterior condyles extending proximally and anteriorly to an area that is in the same plane as a continuation of the posterior cortex of the distal one fourth to one third of the femur. Such an embodiment may comprise separate medial and lateral components or they may be attached together to form one component that replaces or resurfaces the medial and lateral condyles.

Historically, many early total knee femoral components 12 did nothing regarding the patello-femoral joint. Because a certain percentage of those patients had anterior knee pain, an anterior flange was added to the femoral component 12 to resurface the trochlea (patellar groove). This weakened the patella and resulted in fractures in some patients. Recently techniques have been developed to minimize patellar pain which do not require implantation of a component. The embodiment shown in FIG. 14 does not have an anterior flange that is an integral part on the condylar portion of the prosthesis. It is anticipated that such a device 12 alone may, in some patients, be adequate to replace the femoral condyles and allow the surgeon to treat the patello-femoral joint as he/she felt was indicated. Alternatively, a separate patello-femoral articular surface or surfaces could be implanted. The patello-femoral implant(s) could be entirely separate or could be modular and attached to the device shown in FIG. 14. In some instances, the embodiment illustrated in FIG. 14 includes the ability to attach a modular anterior flange (trochlear groove) to the device shown in the Figure. In this regard, FIGS. 16T-16W (discussed below) illustrate some methods for attaching various embodiments of a modular anterior flange 57 (or modular patella-femoral component).

Implementations of the present invention embrace a femoral component 12, a tibial component 14, a modular attachment 30, stem 500 (discussed hereafter), and/or any other suitable components that each comprise a metal, metal alloy, ceramic, carbon fiber, glass, polymer (including, without limitation, bone cement, nylon, polyethylene, polyester, polytetrafluoroethylene (Teflon®), and/or any other suitable polymer), organic material, retrieved human or animal tissue, cementless material, and naturally occurring or synthetic materials used either separately or in any combination of two or more of the materials.

As may be appreciated by reference to the above discussion and the corresponding Figures, currently-existing femoral components 12 provide an articular surface that only extends a short distance in the proximal anterior direction of the posterior condyle. For example, as may be seen with reference to FIGS. 2A and 8A, the articular surface at the anterior end of the posterior condyle typically extends to and replaces at most the posterior third of the posterior condyle, as measured from the most posterior portion of the patient's original posterior condyle (or from the most posterior portion of the femoral component 12) to a plane that is a continuation of the distal one fourth to one third of the posterior cortex of the femoral shaft.

In contrast, the various embodiments of the femoral component 12 illustrated in the Figures and discussed above provide an extended articular surface for either or both of the medial condyle and the lateral condyle that extends in a proximal anterior direction so as to extend half or more of the anteroposterior distance between the most posterior portion of the posterior condyle and the plane that is a continuation of the distal one fourth to one third of the posterior cortex of the femoral shaft. In some embodiments, the extended articular surface extends at least two-thirds of the anteroposterior distance between the most posterior portion (e.g., as shown by line 300 in FIG. 8B) of the posterior condyle and the plane (e.g., as shown by line 302 in FIG. 8B) that is a continuation of the distal one fourth to one third of the posterior cortex of the femoral shaft. In other embodiments, the extended articular surface extends nearly the entire anteroposterior distance between the most posterior portion of the posterior condyle and the plane that is a continuation of the distal one fourth to one third of the posterior cortex of the femoral shaft. In still other embodiments, the extended articular surface may extend even further, to encompass a distal portion of the posterior cortex of the femoral shaft, as illustrated in FIGS. 16A-16D.

The surface of the extension, which may or may not contact bone and is a continuation of the femoral articular surface, can be referred to as the full flex articulation. There may be a corresponding surface on the posterior edge of the medial and or lateral tibial articulation which is not part of the articular surface of the tibia when the tibia is in full extension. For example, in some implementations of the current invention there is a corresponding surface on the posterior edge of the medial tibial articulation where the center of the medial articular surface is more than 20% of the distance from the posterior edge of the component to the anterior edge.

Figure 19A:
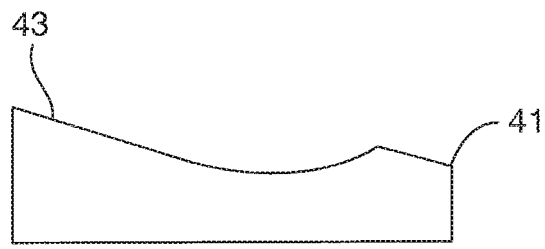
FIG. 19A illustrates a tibial component that does not have an articular surface posterior to the main articular surface.
Figure 19B:
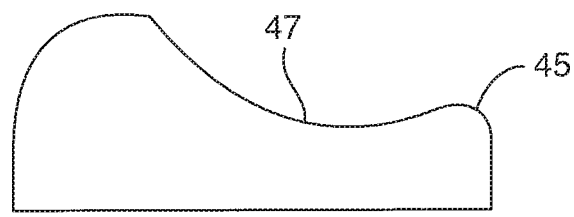
FIG. 19B illustrates the tibial full flex articulation being posterior to the main weight bearing articulation.

The embodiment illustrated in FIG. 19A shows a non-articular surface 41 posterior to the main articular surface 43. FIG. 19B illustrates a full flex articular surface 45 and an articular surface 47. The tibial full flex articulation of FIG. 19B is posterior to the main weight bearing articulation and articulates with a specific articular area on the femoral component, the femoral full flex articulation (proximal extension 50) shown in FIGS. 16A-16Q and shown in a slightly shortened embodiment in FIG. 16E.

Figure 16A:
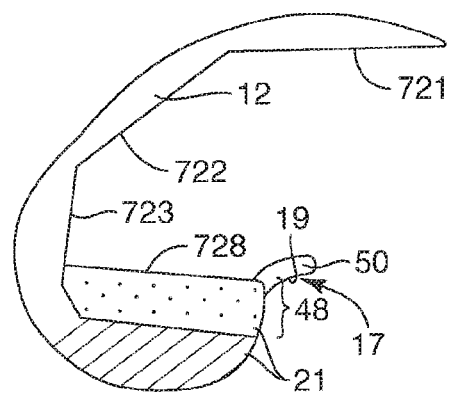
FIGS. 16A-16D illustrate a manner in which an articulating surface of the femoral components shown in FIGS. 15A-15D may be extended.
Figure 16B:
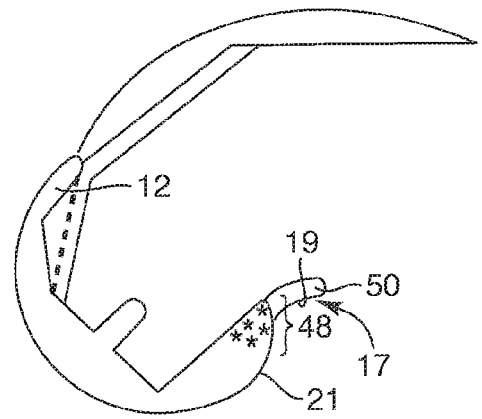
Figure 16C:
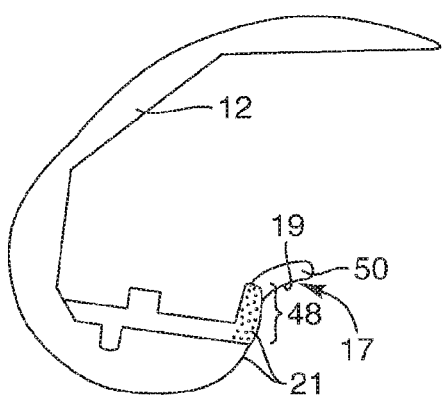
Figure 16D:
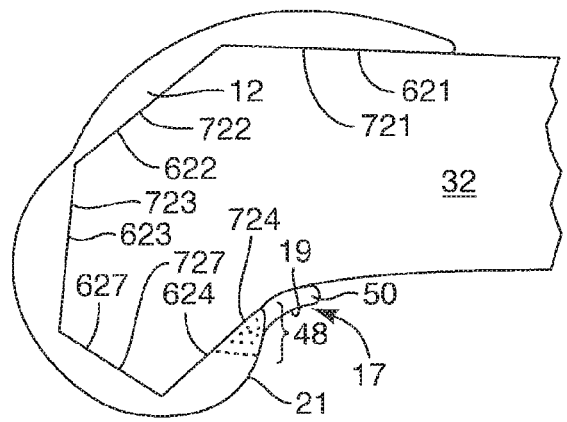
Figure 16E:
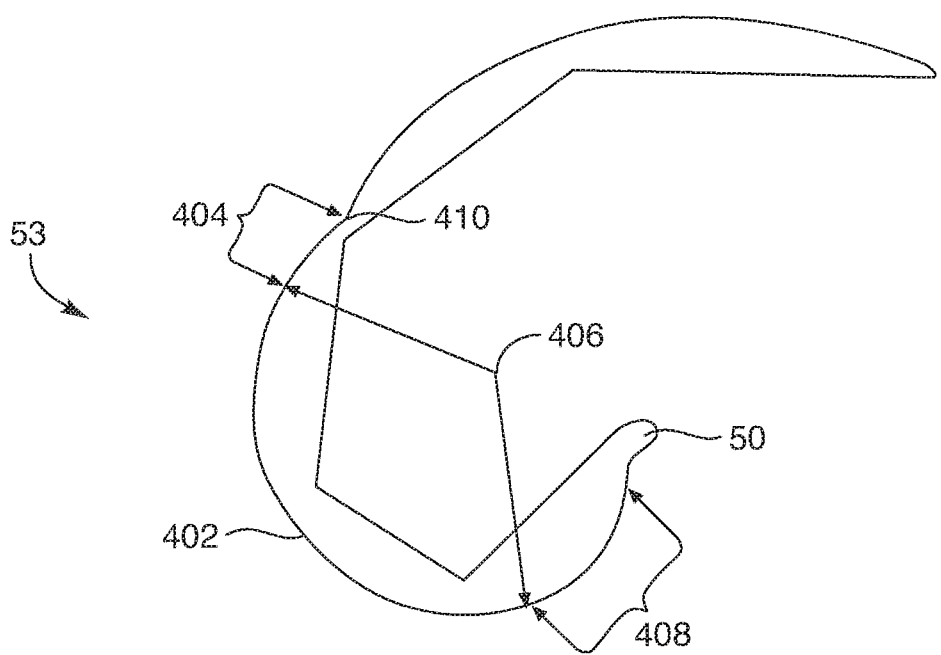
FIG. 16E illustrates a shortened embodiment in which an articulating surface of the femoral component may be extended.

With continued reference to FIG. 16E, in some embodiments of the present invention the articular surface 402 of femoral component 53 comprises sections of various surface radii 404, 406 and 408. Each section is provided as a means for controlling the relationship between the femoral component 53 and the tibial component (not shown) throughout the range of flexion for the knee. However, in some embodiments, radius 406 may be constant and replace radii 404 and 408.

Figure 16F:
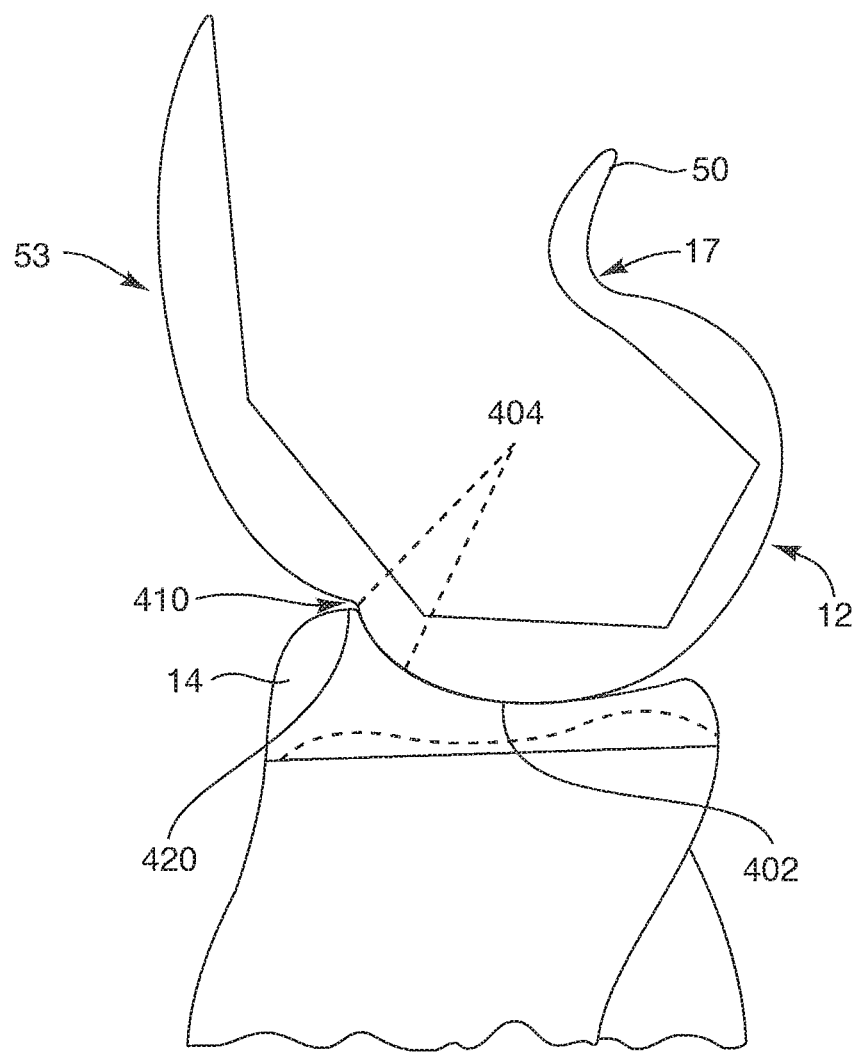
FIGS. 16F-16P illustrate flexion of a non-limiting embodiment of a femoral component having a decreasing radius, wherein the decreasing radius provides laxity over a portion of the range of flexion in accordance with a representative embodiment of the present invention.
Figure 16G:
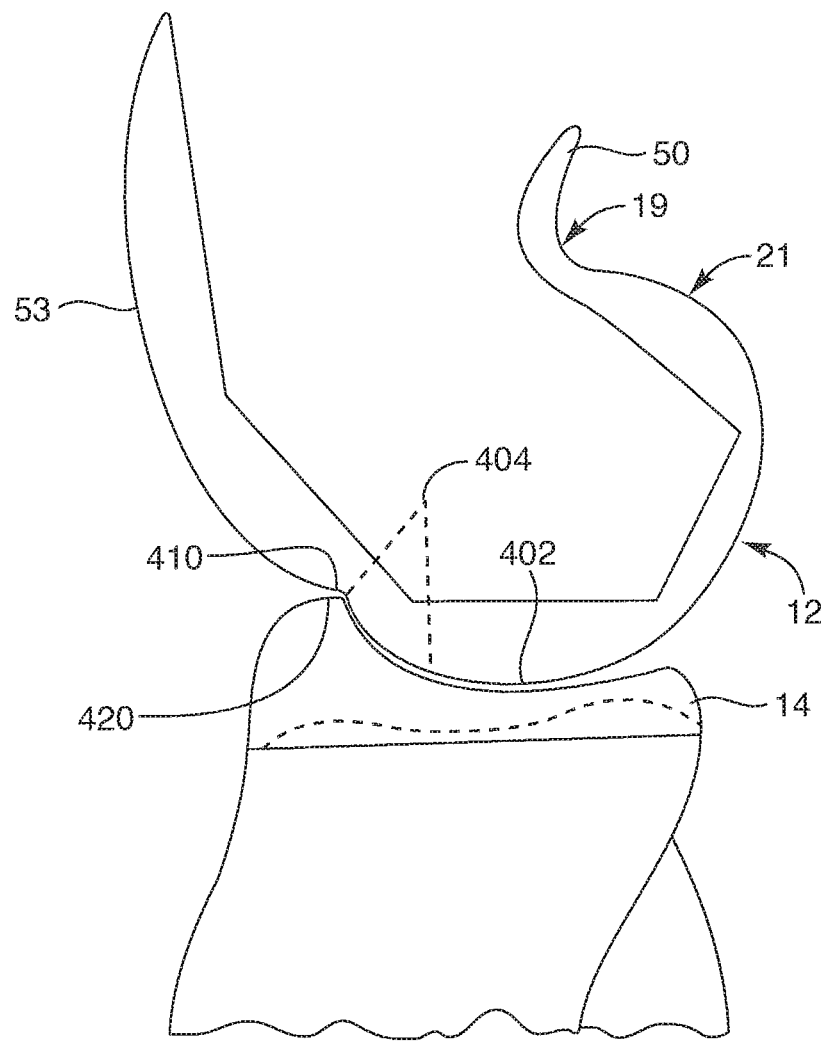

Radius 404 is characterized as having a decreasing radius such that an indentation 410 is formed on the articular surface 402. In some embodiments, indentation 410 is configured to receive anterior ridge 420 of tibial component 14 when the knee joint is hyper extended to approximately −10°, as shown in FIG. 16F. Upon further hyperextension, as shown in FIG. 16G, indentation 410 further impinges upon anterior ridge 420, such that the interface between indentation 410 and anterior ridge 420 acts as a fulcrum between femoral component 53 and tibial component 14. Therefore, as the knee joint is hyper-extended beyond approximately −10°, radius 404 of the articular surface 402 is distracted from the tibial component 14, as shown. As this distraction increases, the dense connective tissues of the knee joint are stressed thereby limiting further hyper-extension of the knee joint.

Figure 16H:
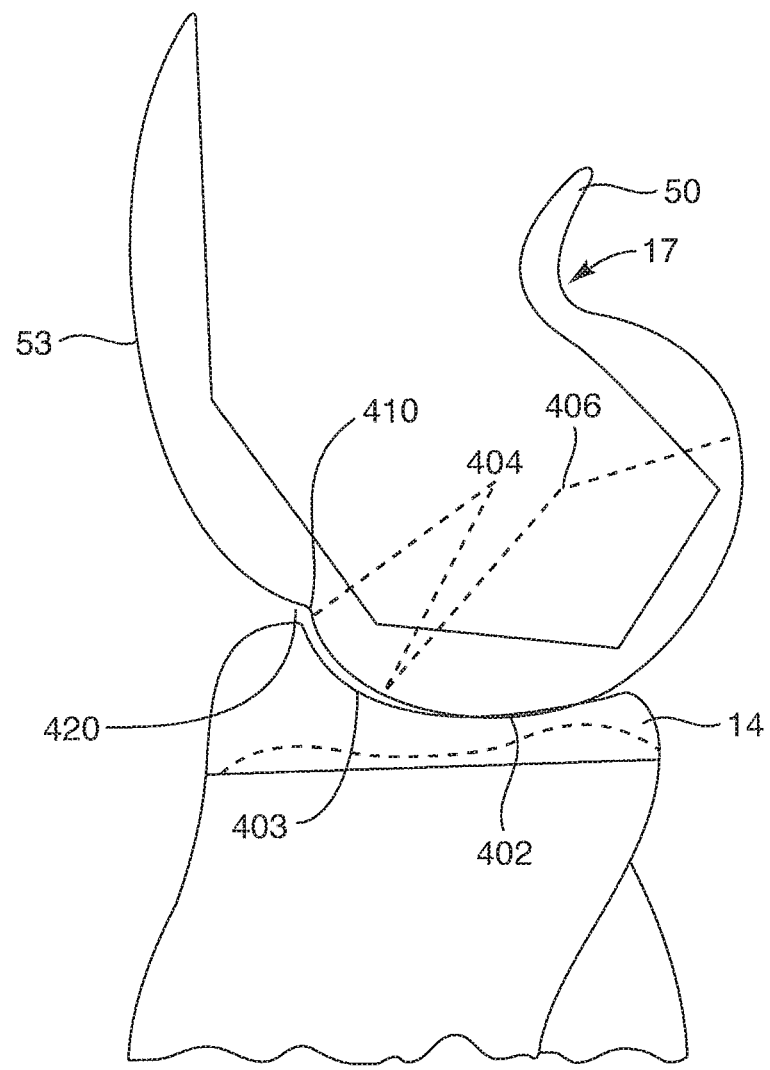

Referring now to FIG. 16H, a knee joint is shown in a neutral, extended position at approximately 0° flexion. At approximately 0° flexion, radii 404 and 406 are partially in contact with tibial articular surface 403, yet the knee joint is not fully constrained. As such, femoral component 53 is permitted to move anteriorly and posteriorly relative to the tibial component 14. In some embodiments, radii 404 and 406 provide laxity within the knee joint between approximately 0° and 20° flexion. In other embodiments, radii 404 and 406 provide laxity within the knee joint between approximately 0° and 40° flexion.

Figure 16I:
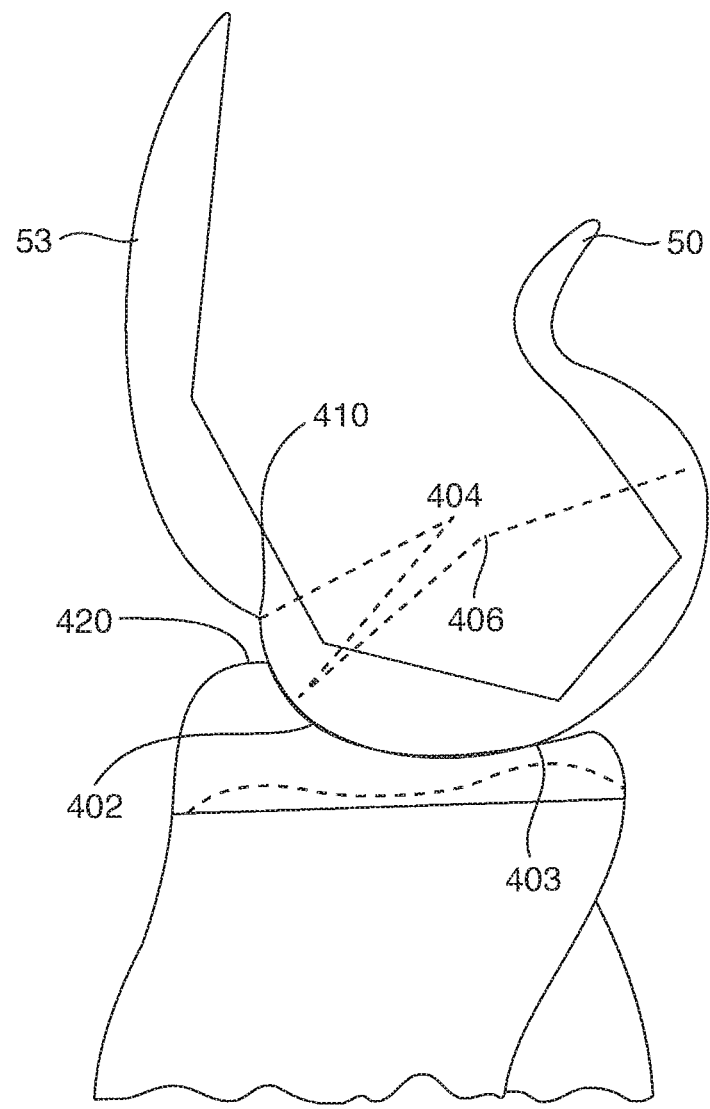
Figure 16J:
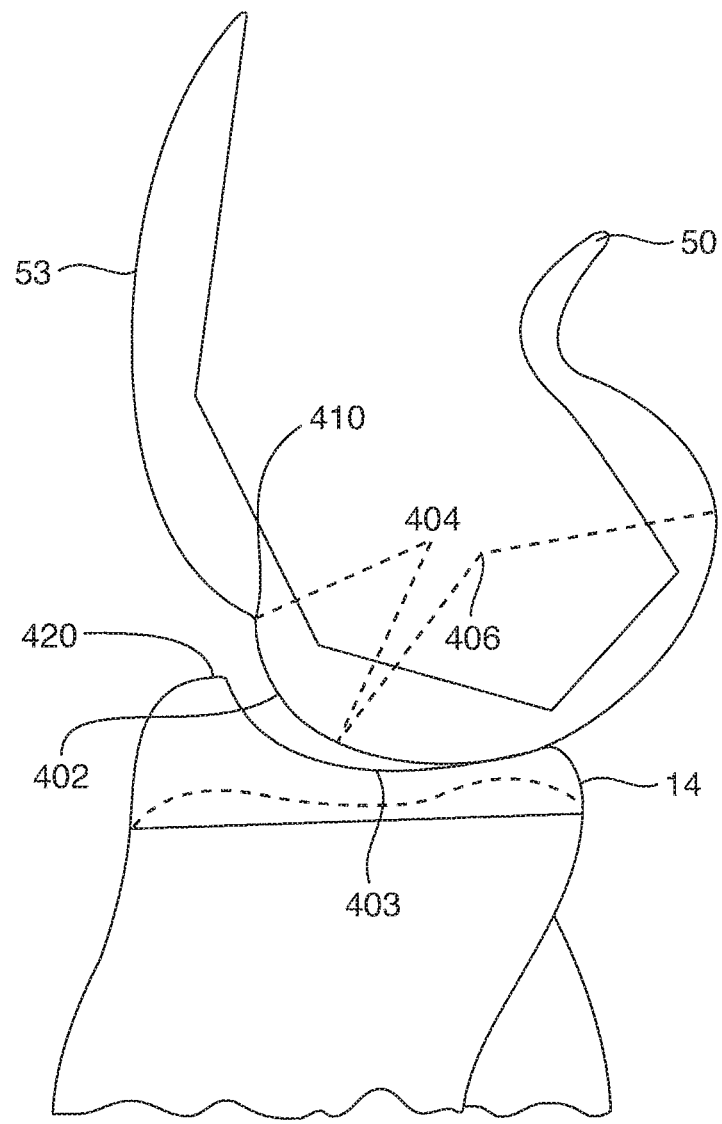

Referring now to FIG. 16I, a knee joint is shown at approximately 10° flexion with the femoral component 53 being shifted anteriorly relative to tibial component 14. FIG. 16J shows a knee joint at approximately 10° flexion wherein the femoral component 53 has been shifted posteriorly relative to tibial component 14. Anterior and posterior laxity within the knee joint, as provided by radius 404, is limited both by tension within the dense connective tissues of the knee joint, and by the curvatures of the opposing femoral and tibial articular surfaces 402 and 403. By providing laxity between approximately 0° and approximately 20° the natural mechanics of knee flexion are preserved, as sensed or experienced by the user. In some embodiments, laxity is eliminated between approximately 0° and approximately 20°, thereby modifying the natural mechanics of knee flexion as may be desired. This is achieved by having radii 404 and 408 replaced by radius 406.

Figure 16K:
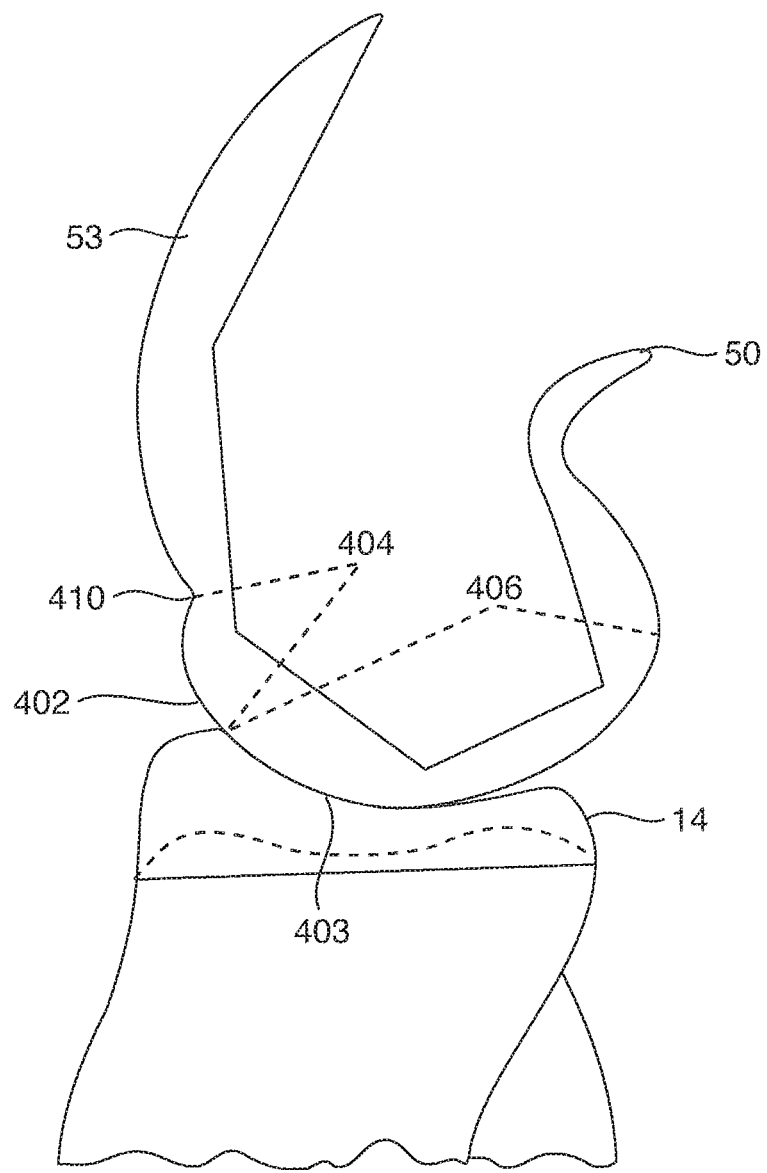
Figure 16L:
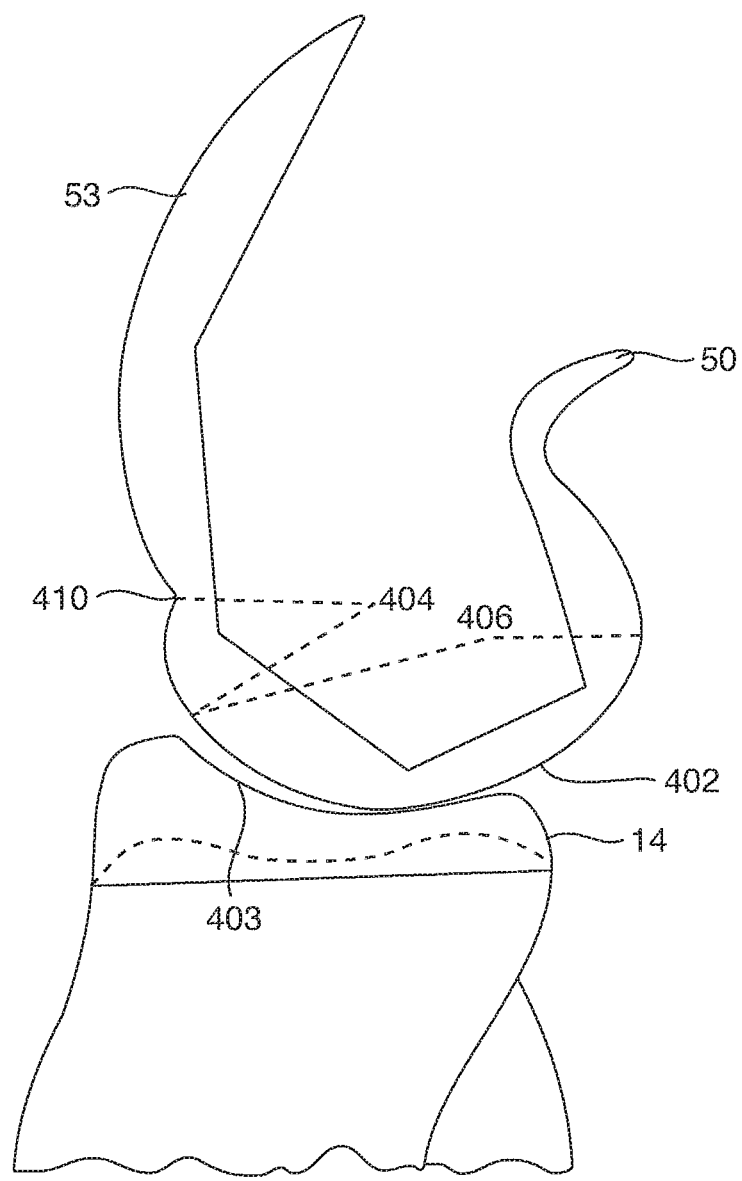
Figure 16M:
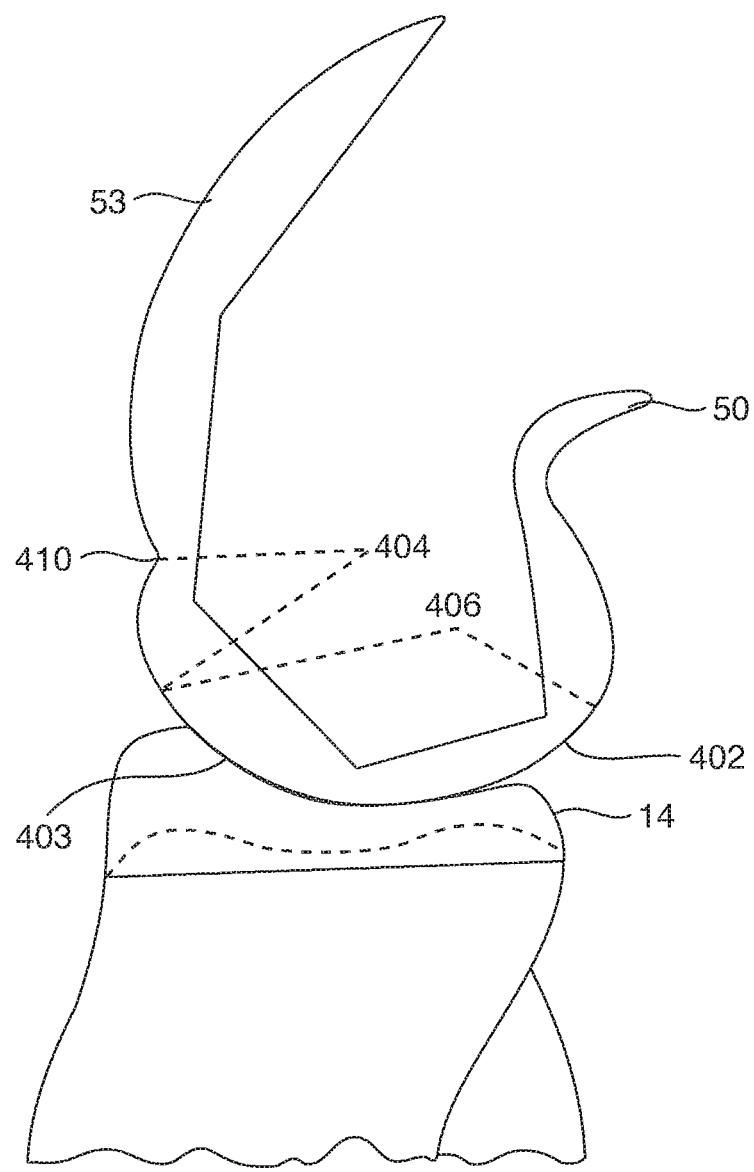
Figure 16N:
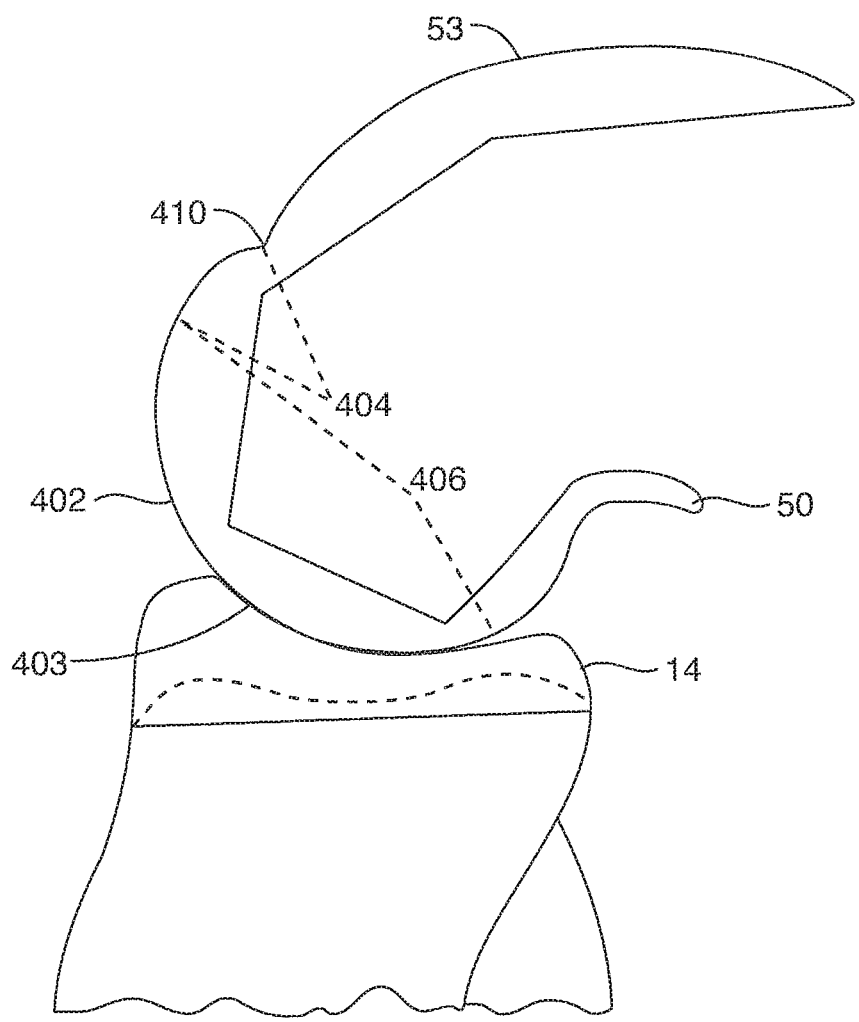
Figure 16O:
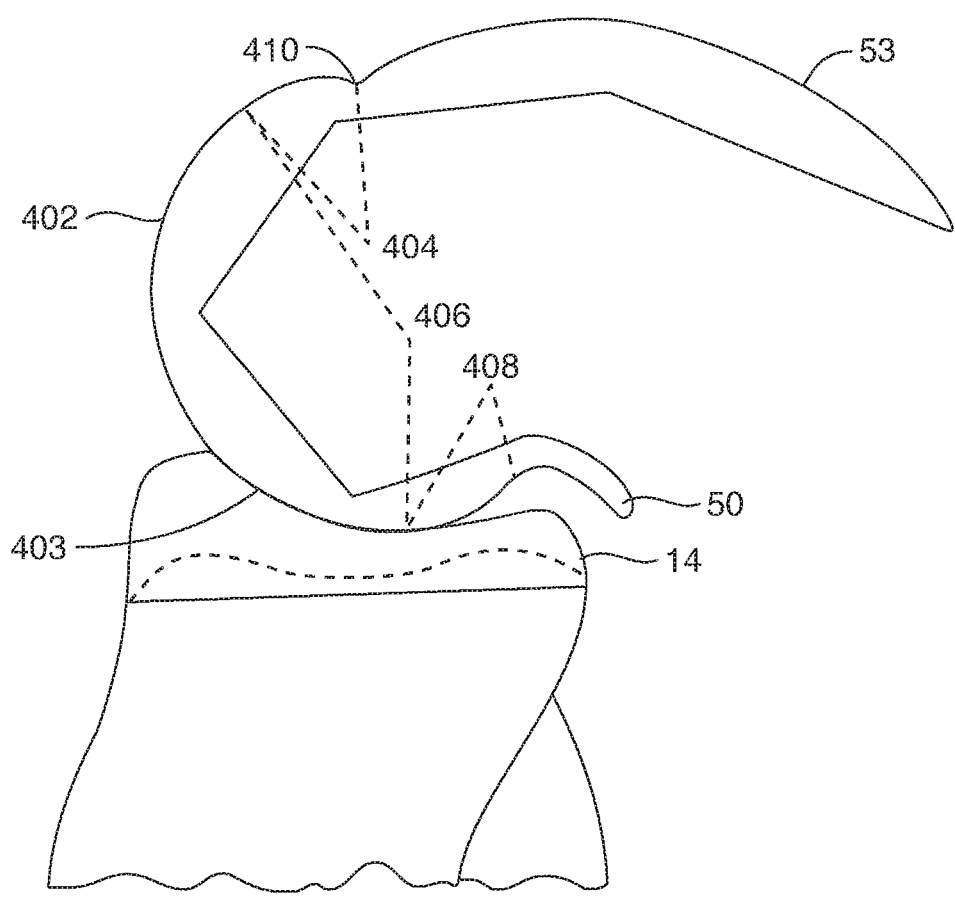
Figure 16P:
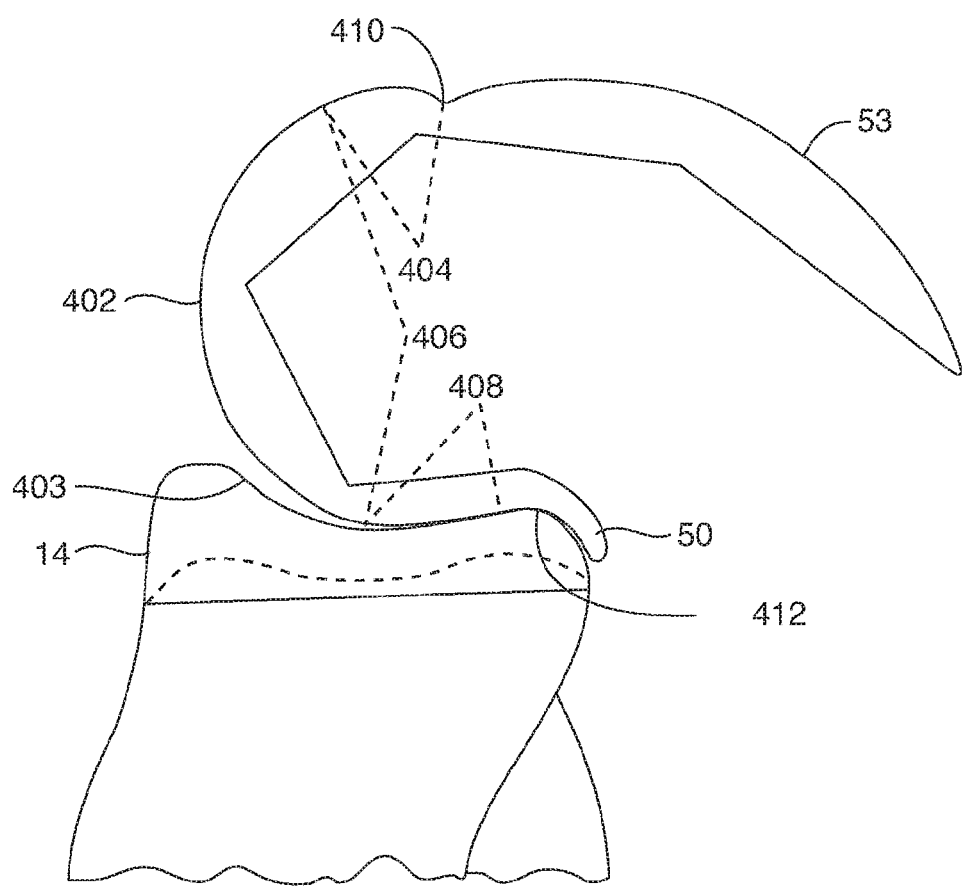

Upon further flexion of the knee joint to approximately 20°, radius 406 is largely in contact with tibial articular surface 403, as shown in FIG. 16K. However, in some embodiments laxity within the knee joint is maintained at approximately 20° flexion such that the femoral component 53 is permitted to shift anteriorly (FIG. 16K) and posteriorly (FIG. 16L) relative to the tibial component 14. As the knee joint is further flexed, radius 406 assumes full contact with the opposing tibial articular surface 403 thereby fully constraining anterior and posterior movement within the knee joint, as shown in FIG. 16M. Full contact and constraint within the knee joint is thereafter maintained through the remaining mid-flexion movement of the joint, as shown in FIGS. 16N and 16O. Beyond approximately 110° flexion, radius 408 begins to pick up contact with tibial articular surface 403 thereby causing distraction of the femoral and tibial components 53 and 14, as shown in FIG. 16P. As the knee joint is further distracted, proximal extension 50 maintains contact with posterior articular feature 412 of the tibial component 14.

Figure 16Q:
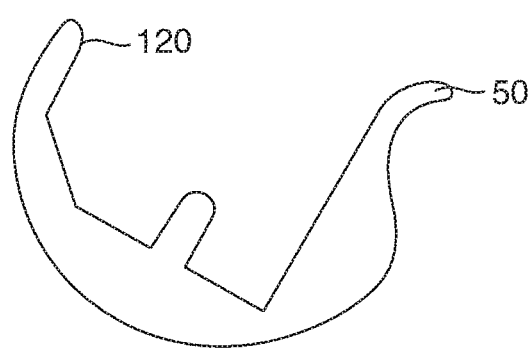
FIG. 16Q illustrates a unicompartmental femoral component including an extended articulating surface in accordance with a representative embodiment of the present invention.
Figure 16R:
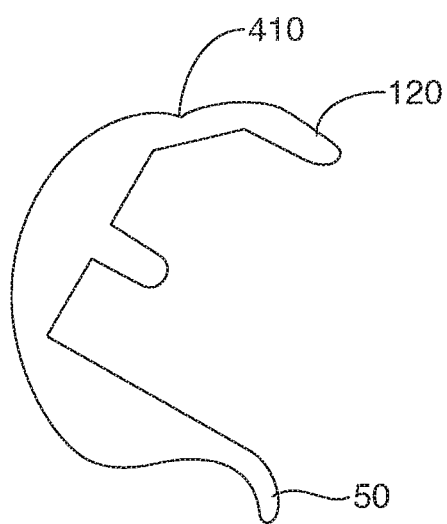
FIG. 16R illustrates a unicompartmental femoral component including a decreasing radius and an indentation in accordance with a representative embodiment of the present invention.
Figure 16S:
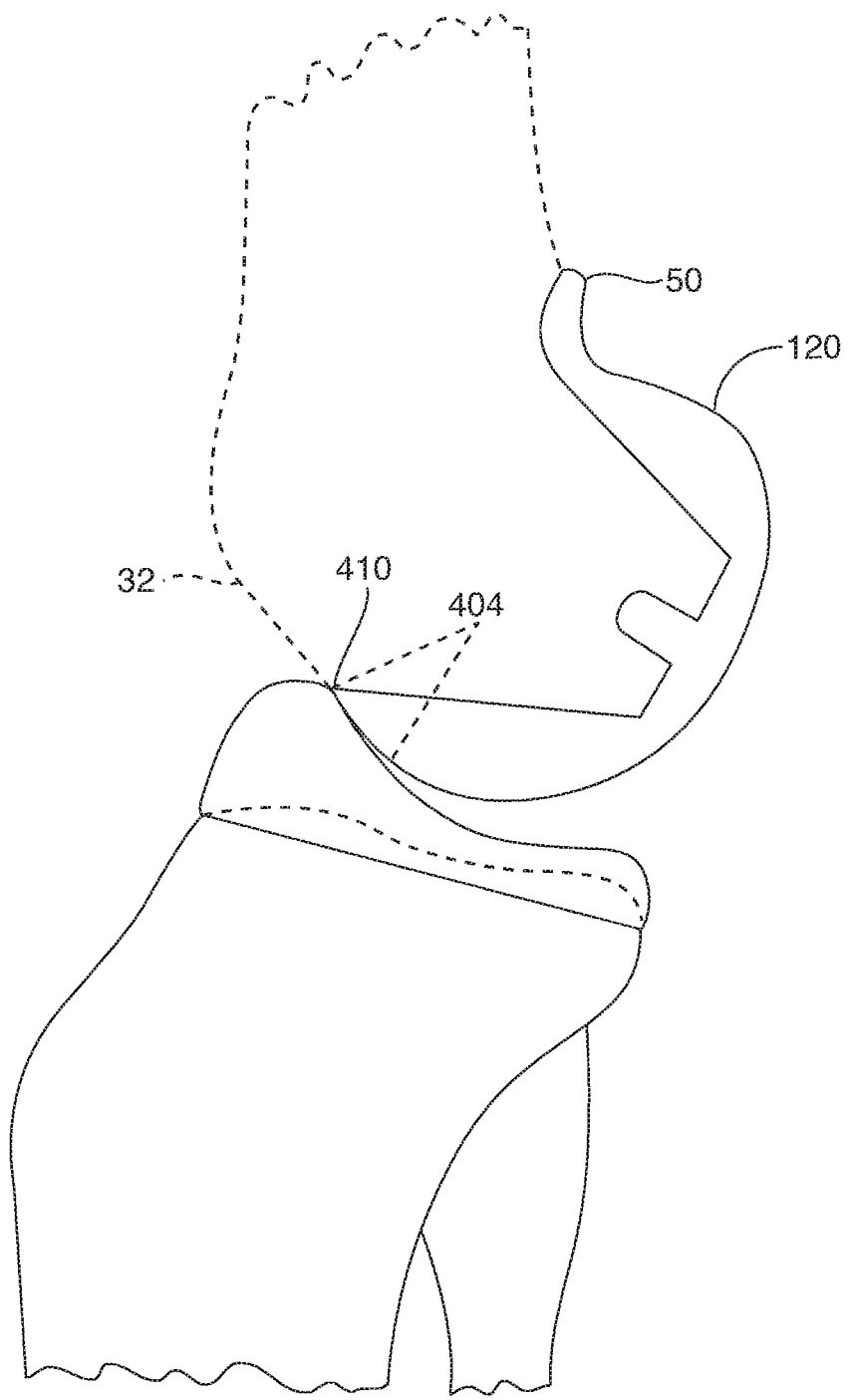
FIG. 16S illustrates a truncated femoral component including an indentation in accordance with a representative embodiment of the present invention.

With reference to FIG. 16Q, a representative embodiment of a unicompartmental femoral component 120 is shown. The various components of the present invention may be substituted with a unicompartmental component, as discussed below. In some embodiments, unicompartmental femoral component 120 further comprises a decreasing radius 404 providing indentation 410, as shown in FIG. 16R. In other embodiments, unicompartmental femoral component 120 is truncated thereby providing indentation 410 at intersection between component 120 and non-resectioned anterior condylar surface of femur 32, as shown in FIG. 16S.

The unicompartmental component is generally implanted to replace the weight bearing portion of the knee joint medially or laterally. The unicompartmental component may be used medially and/or laterally as two separate femoral and two separate tibial components on just the weight bearing portion of the joint. In some embodiments, the unicompartmental component is used with two femoral or two tibial components joined, but ignoring the patellofemoral joint. In other embodiments, the unicompartmental component is used as one femoral component replacing the medial and lateral weight bearing portions of the distal femur and also a portion of, or all of the patello-femoral joint with either a one piece tibial component or separate medial and lateral tibial components. Finally, in some embodiments the unicompartmental component is a one-piece, femoral component replacing the patello-femoral joint and either the medial or lateral weight-bearing portion of the femur.

In some embodiments, the unicompartmental component 120 includes a full flex femoral articulation surface 50. As previously discussed, the articulation surface or extension 50 is configured to provide extended contact between the unicompartmental femoral component 120 and a full flex tibial articulation surface 55 of a tibial component during deep flexion of the knee. In some embodiments, a portion of the popliteal surface 202 of the femur is removed to accept placement of the articulation surface 50. In other embodiments, a unicompartmental component (not shown) is provided for use in conjunction with a modular full flex femoral articulation surface (not shown). Thus, in some embodiments a first portion of the femur is prepared to receive the unicompartmental component 120, and a second portion of the femur is prepared to receive a modular full flex femoral articulation surface (not shown). As such, a combination of the unicompartmental component and the modular full flex femoral articulation surface provide a unicompartmental femoral component that is functionally equivalent to the unicompartmental femoral component 120.

In some embodiments, the unicompartmental femoral component 120 is used in conjunction with a unicompartmental tibial component. In other embodiments, the unicompartmental femoral component 120 is used in conjunction with a full tibial component. Finally, in some embodiments, the unicompartmental femoral component 120 is used directly in conjunction with a natural surface of the opposing tibia.

Where permitted, implementation of a unicompartmental femoral component 120 provides several advantages over total knee replacement procedures. For example, while an eight-inch incision is typically required for a total knee replacement surgery, a partial knee replacement utilizing a unicompartmental femoral component 120 requires an incision of approximately three-inches. Thus, one benefit of a unicompartmental femoral component 120 is decreased scarring following the partial knee replacement procedure.

Other benefits of a partial knee replacement include decreased recovery time, increased range of motion, and decreased overall damage to the knee. A total knee replacement procedure may require the patient to remain in the hospital for up to four days. It can also take up to three months, or longer, to recover from the surgery. However, with a partial knee replacement procedure, a patient typically requires no more than two days of hospitalization followed by one month of recovery. Additionally, a patient is typically able to walk without assistance a week or two following the partial knee replacement procedure.

Unlike some total knee replacement procedures, insertion of the unicompartmental femoral component 120 generally preserves more ligaments thereby providing a fuller range of motion. For example, in some partial knee replacement procedures, the anterior and/or posterior cruciate ligaments are preserved, as desired. A partial knee replacement also generally results in less damage to the knee because the surgery is minimally invasive thereby causing minimal tissue, muscle and tendon damage to the knee.

For some partial knee replacement procedures, various methods may be implemented to address pain and discomfort caused by patello-femoral arthritis. For example, for some partial knee replacement procedures denervation of the patella is performed. In other partial knee replacement procedures, denervation of the opposing femoral groove is performed. In some embodiments of the present invention the unicompartmental femoral component 120 is designed to reproduce the natural patello-femoral joint throughout the range of motion and to facilitate tracking of the patella in the femoral groove. In other embodiments, a combination of denervation and natural design of the unicompartmental femoral component 120 are implemented to adequately address the patello-femoral arthritis.

Figure 20A:
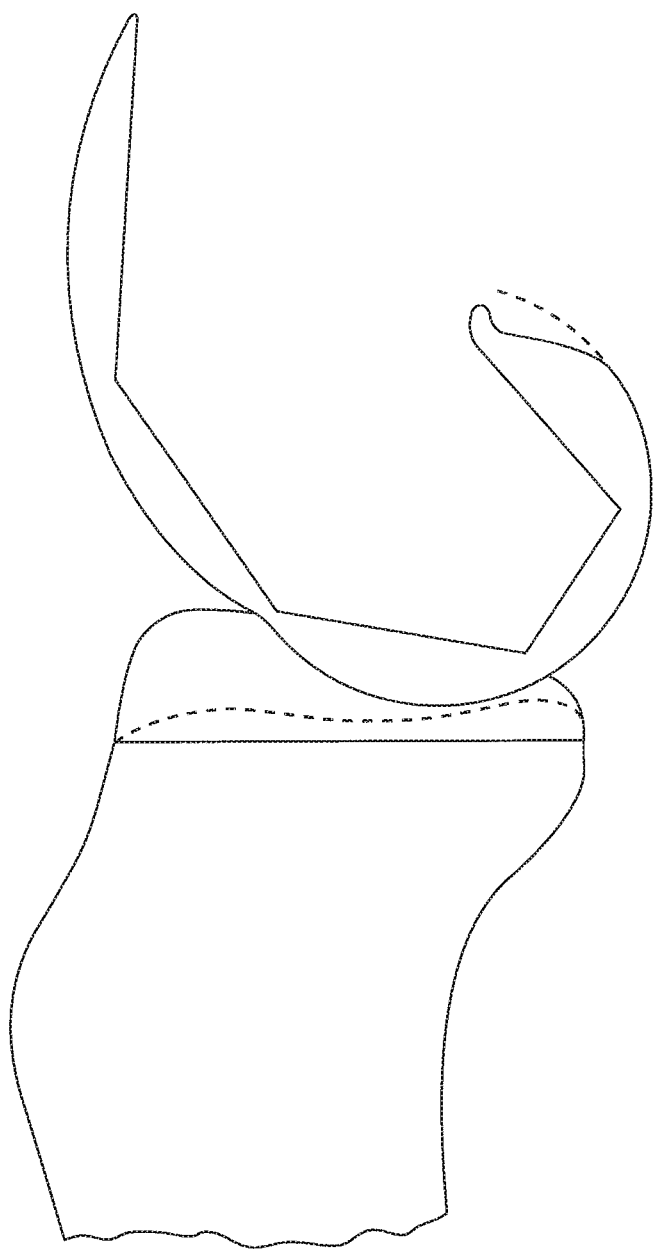
FIGS. 20A-20I illustrate a representative interaction of a femoral full flex articulation and a tibial full flex articulation.
Figure 20B:
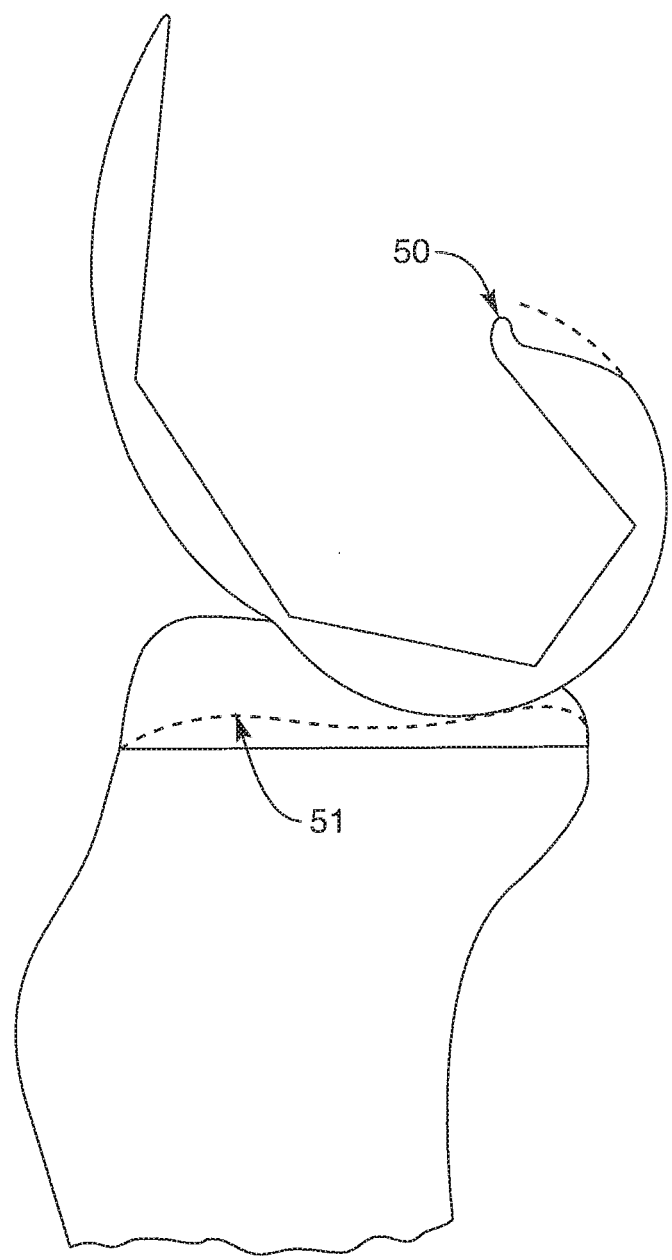
Figure 20C:
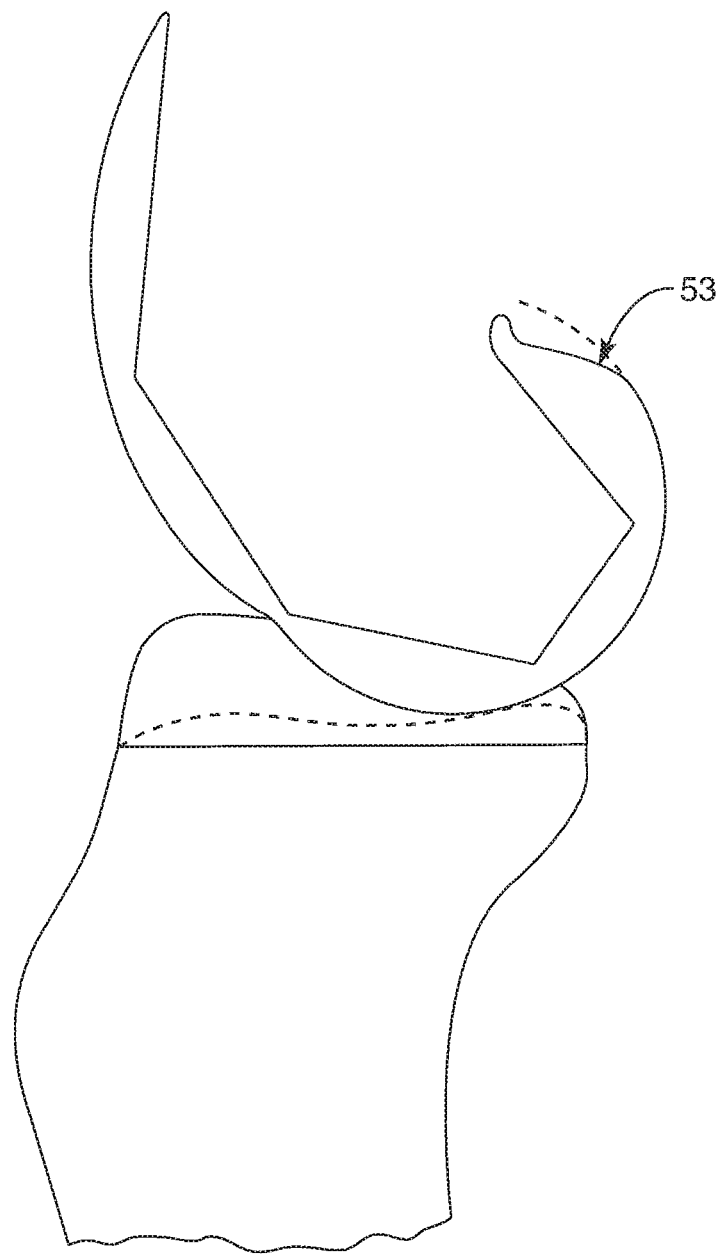
Figure 20D:
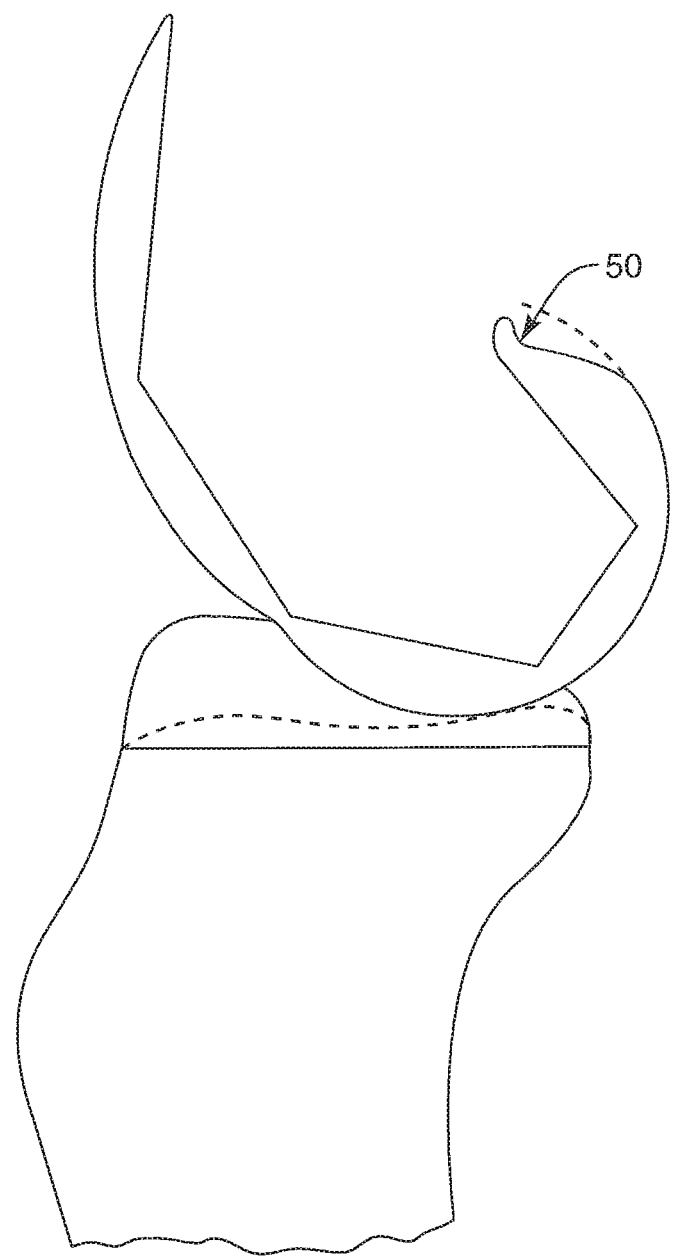
Figure 20E:
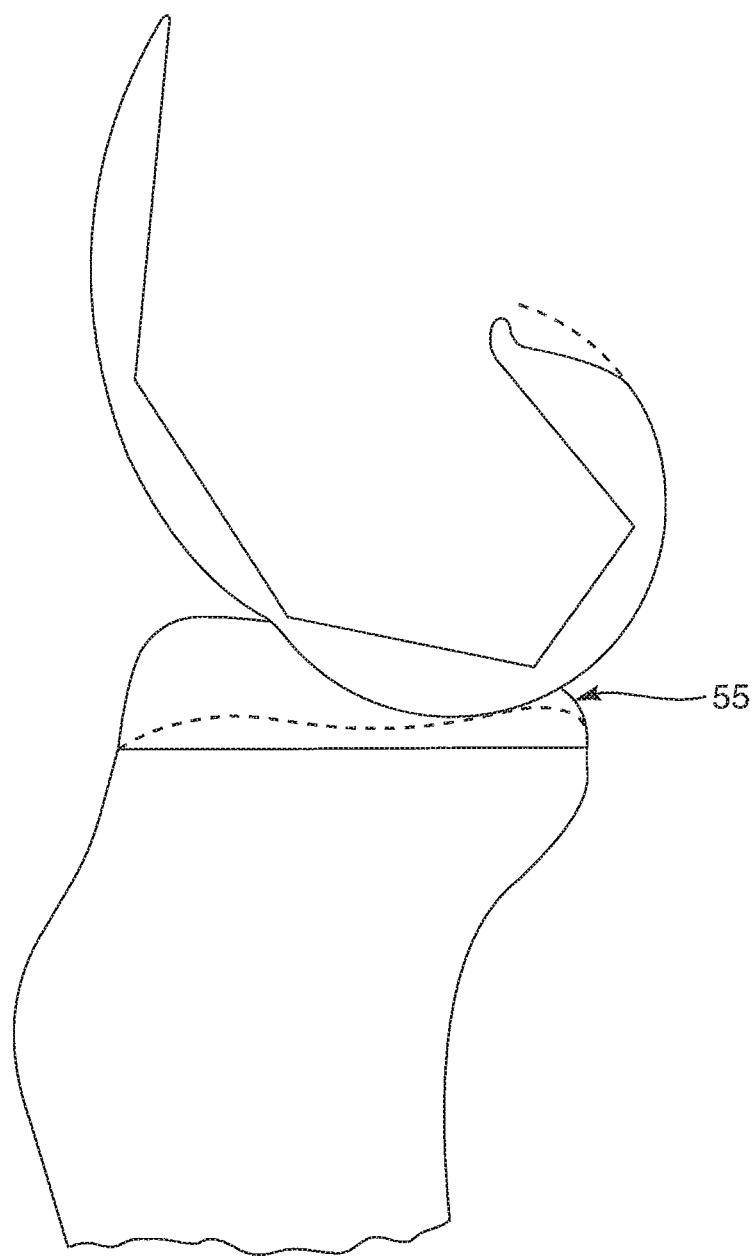
Figure 20F:
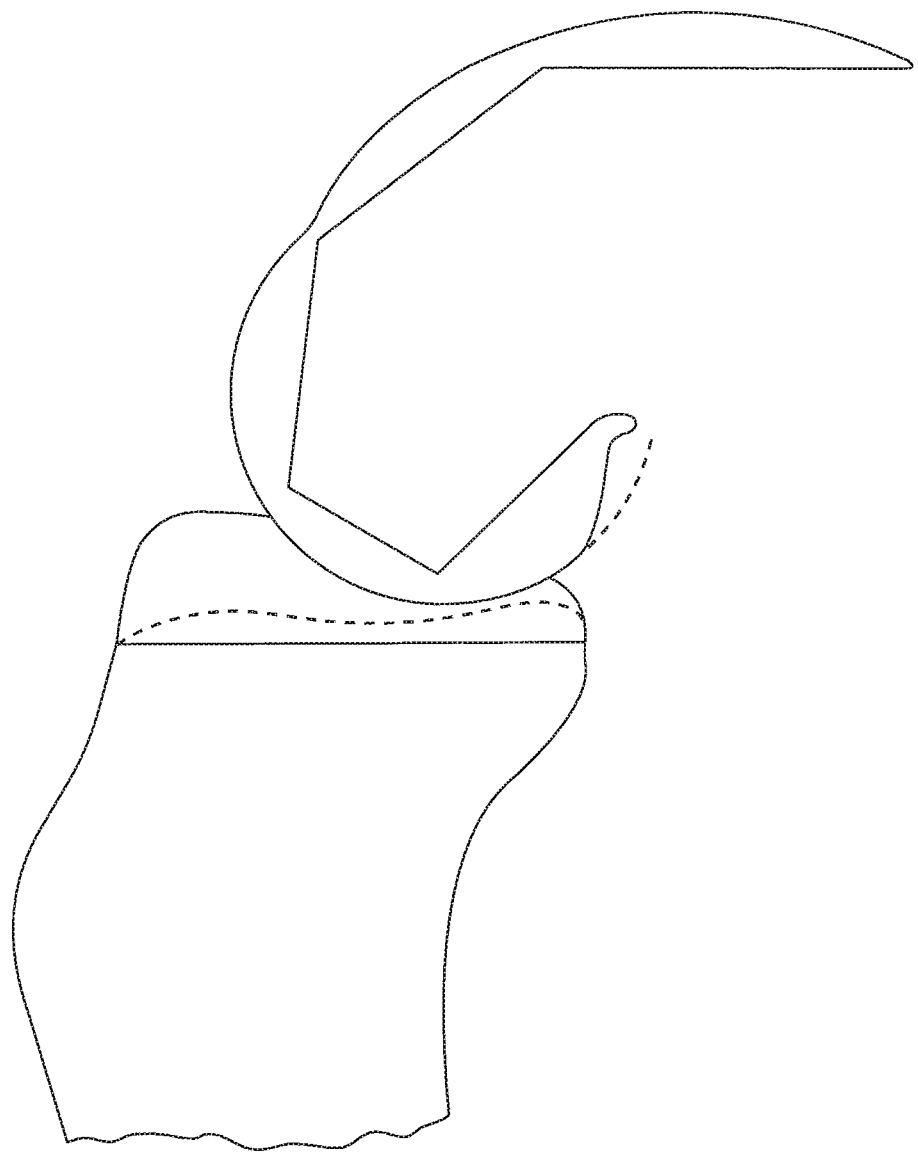
Figure 20G:
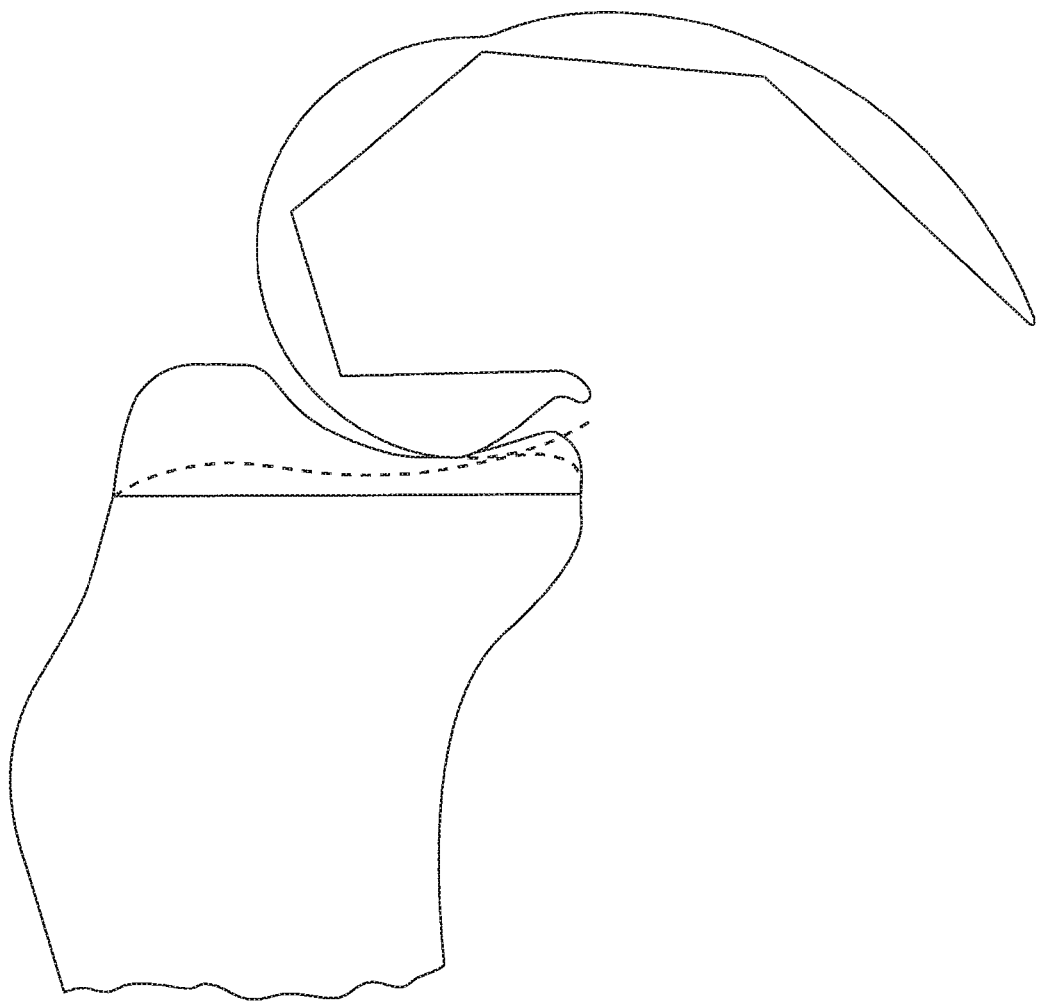
Figure 20H:
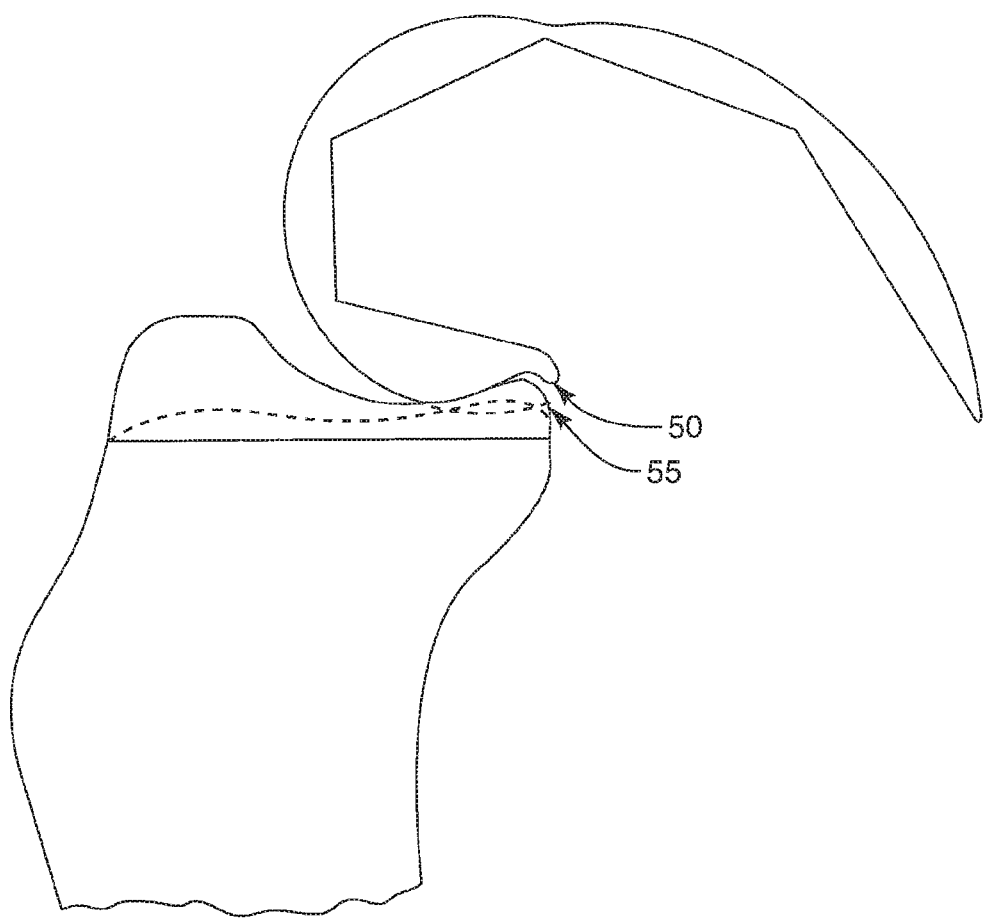
Figure 20I:
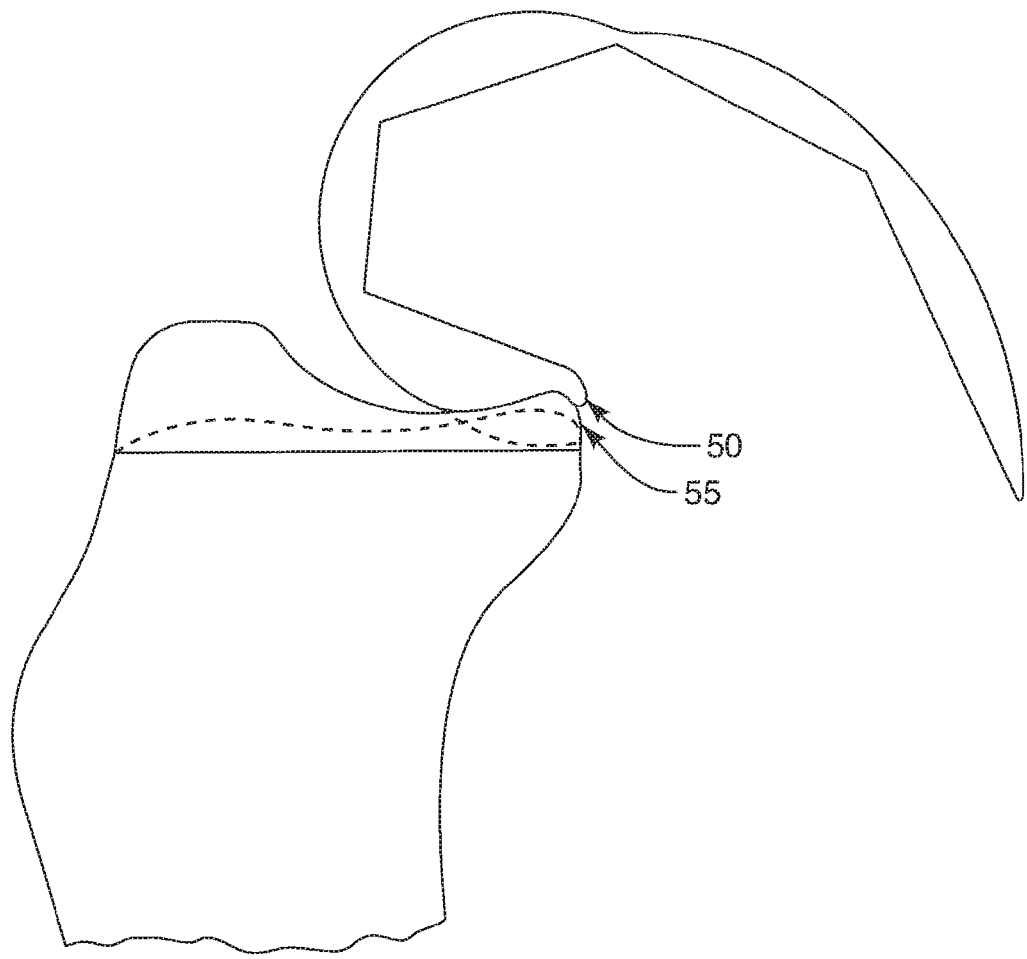

The interaction of the femoral full flex articulation 50 and the tibial full flex articulation 55 is illustrated in FIGS. 20A-20I, wherein FIGS. 20A-20E are at 0 degrees, FIG. 20F is at 90 degrees, FIG. 20G is at 130 degrees, FIG. 20H is at 150 degrees, and FIG. 20I is at 160+ degrees. FIG. 20B identifies a representative position of unresected tibial plateau 51. FIG. 20C identifies a representative closing radius on a posterior portion of a femoral component 53. FIG. 20D identifies a representative full flex femoral articulation 50. FIG. 20E identifies a representative full flex tibial articulation 55. FIG. 20H identifies a representative approach of the full flex femoral articulation 50 to the full flex tibial articulation 55 during flexion. FIG. 20I identifies a representative contact of the full flex femoral articulation 50 to the full flex tibial articulation 55 during deep flexion.

FIGS. 15A-15D illustrate the various manners in which the four previously-discussed embodiments of the femoral component 12 provide an extended articular surface 48. The concept of adding more articular surface to the proximal portion of the posterior condyles of the femoral component may be generally accomplished by extending the proximal portion anteriorly until the articular surface approaches, or extends beyond the plane of the posterior surface of the shaft of the distal femur, if that plane were to extend distally. For example, as may be seen from FIGS. 15A-15D, the extended articular surface 48 of each embodiment extends the articular surface at the anterior end of one or both of the medial posterior condyle or the lateral posterior condyle. As illustrated in FIGS. 16A-16D, the articular surface may be further extended in a proximal direction from the end of the extended articular surface 48. This further extension may be provided by a proximal extension 50. The proximal extension 50 may be an integral part of the femoral component 12, it may be a part of the modular attachment 30 (as discussed herein), or it may be provided as a separate and additional component. In one embodiment where the proximal extension 50 is provided, the proximal extension 50 acts as a fulcrum that interacts with the tibia or with the tibial component 14 to increase separation between the femur 32 and the tibia during full functional flexion to improve the deep knee flexion. In another embodiment, the proximal extension 50 allows the normal relationships between the tibia and femur in full functional flexion to exist while maintaining contact between the two surfaces.

Where the femoral component 12 comprises a proximal extension 50 (or a femoral full flex articulation), the proximal extension can comprise any suitable shape. Indeed, in some embodiments (as illustrated by at least FIG. 16F, the proximal extension 50 extends from the femoral component 12 such that a concave articulation surface 17 (or a concave surface of any shape that is suitable for articulating against a portion of the tibia and/or tibial component 14) is disposed at or near a proximal, posterior portion of the femoral component 12. In some embodiments, FIG. 16G illustrates that the proximal extension 50 comprises a first curved articular surface 19, while the femoral component's posterior condylar surface (e.g., a lateral and/or medial condylar surface) comprises a second curved articular surface 21, wherein the first 19 and the second 21 articular surfaces form a reverse curve.

Additionally, where the femoral component 12 comprises a proximal extension 50, the proximal extension can be disposed in any suitable location on the femoral component that allows the concave articulation surface 17 to articulate against a portion of the tibia and/or the tibial component 14 when the knee is in (or is approaching) full flexion. Moreover, the proximal extension 50 can also be used in connection with any suitable femoral component (e.g., as a modular unit or as an integral part) that allows the proximal extension to function as described herein.

In some embodiments, the proximal extension 50 extends from the femoral component 12 so that the concave articulation surface 17 is disposed at or near a proximal, posterior portion of the femoral component (e.g., as shown in FIGS. 16A-16D). Indeed, in one illustration, FIG. 16D shows that in an embodiment in which the femoral component 12 has a first internal surface 721 for contacting an anterior femoral surface and/or cut 621 on the femur 32, a second internal surface 722 for contacting an anterior chamfer cut 622 on the femur, a third internal surface 723 for contacting a distal cut 623 on the femur, a fourth internal surface 727 for contacting a posterior chamfer cut 627 on the femur, a fifth internal surface 724 for contacting a full flexion cut 624 on the femur (or a cut that runs proximally and anteriorly from its distal end towards a posterior surface of the femur), the proximal extension 50 is disposed near the fifth surface 724 (e.g., so as to be disposed at or near a proximal, posterior portion of one or both of the condylar surfaces of the femoral component 24 and/or at or near a popliteal surface of the shaft of the femur).

Figure 16T:
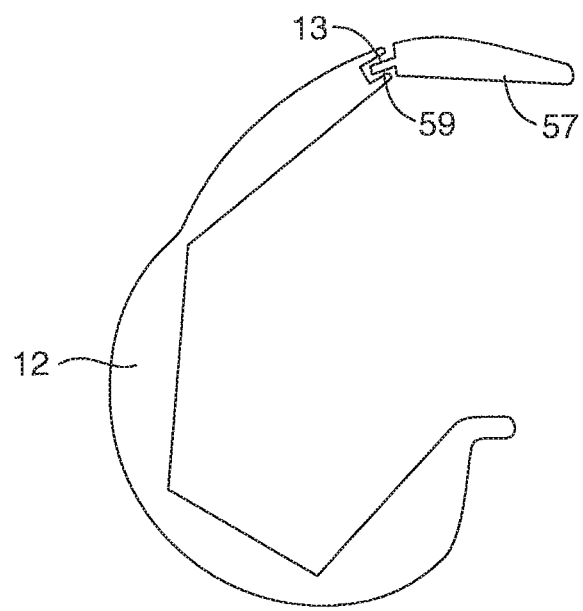
FIG. 16T illustrates a cross-section view of a femoral component coupled to a modular patella-femoral component in accordance with a representative embodiment of the present invention.
Figure 16U:
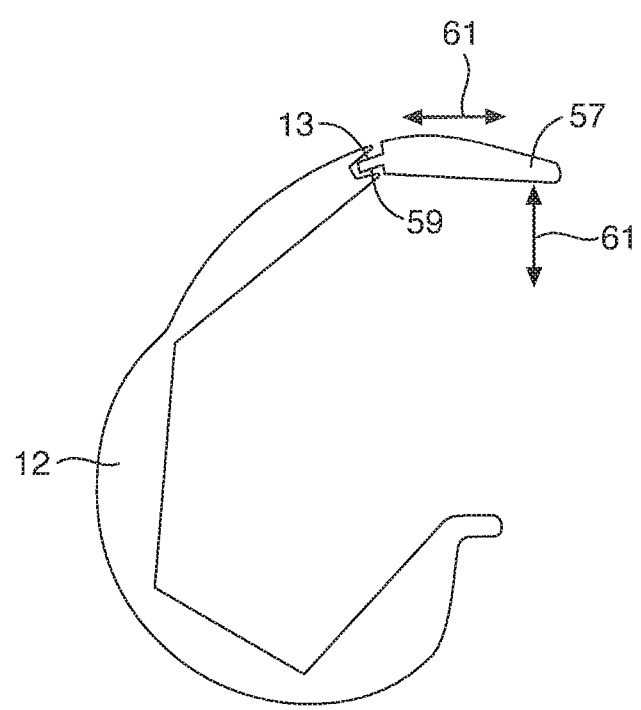
FIG. 16U illustrates a cross-section view of a femoral component slidably coupled to a modular patella-femoral component in accordance with a representative embodiment of the present invention.
Figure 16V:
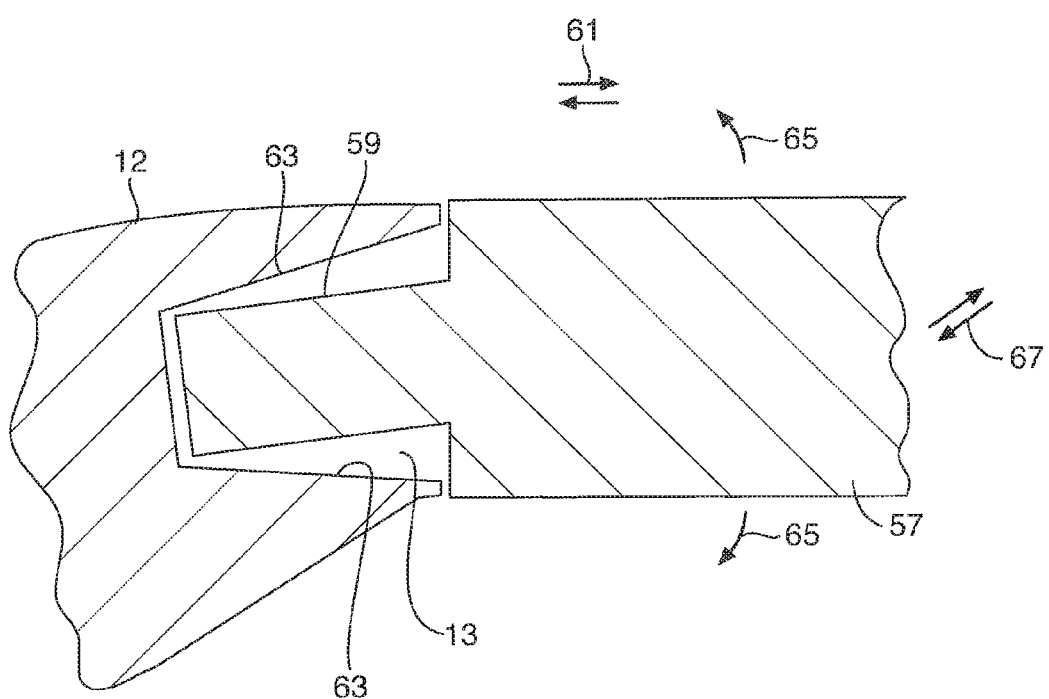
FIG. 16V illustrates a detailed cross-section view of a femoral component having a tapered opening adjustably and slidably coupled to a post of a modular patella-femoral component in accordance with a representative embodiment of the present invention.
Figure 16W:
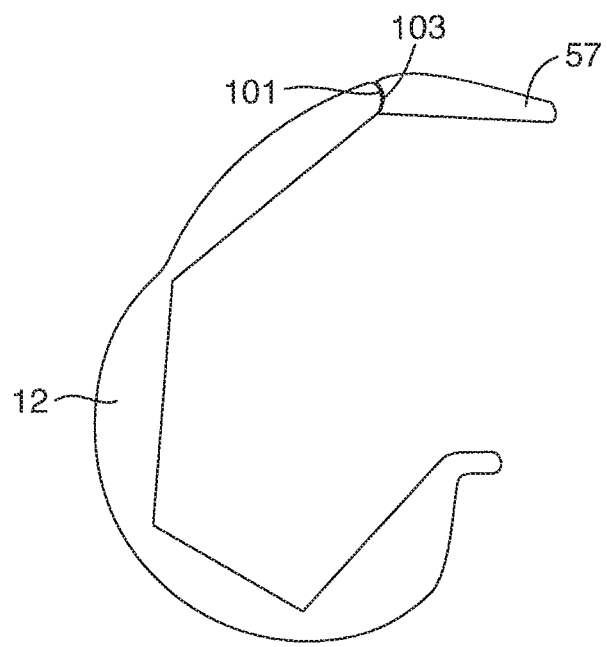
FIG. 16W illustrates a cross-section view of a femoral component having a convex surface abutted with a concave surface of a modular patella-femoral component in accordance with a representative embodiment of the present invention.
Figure 16X:
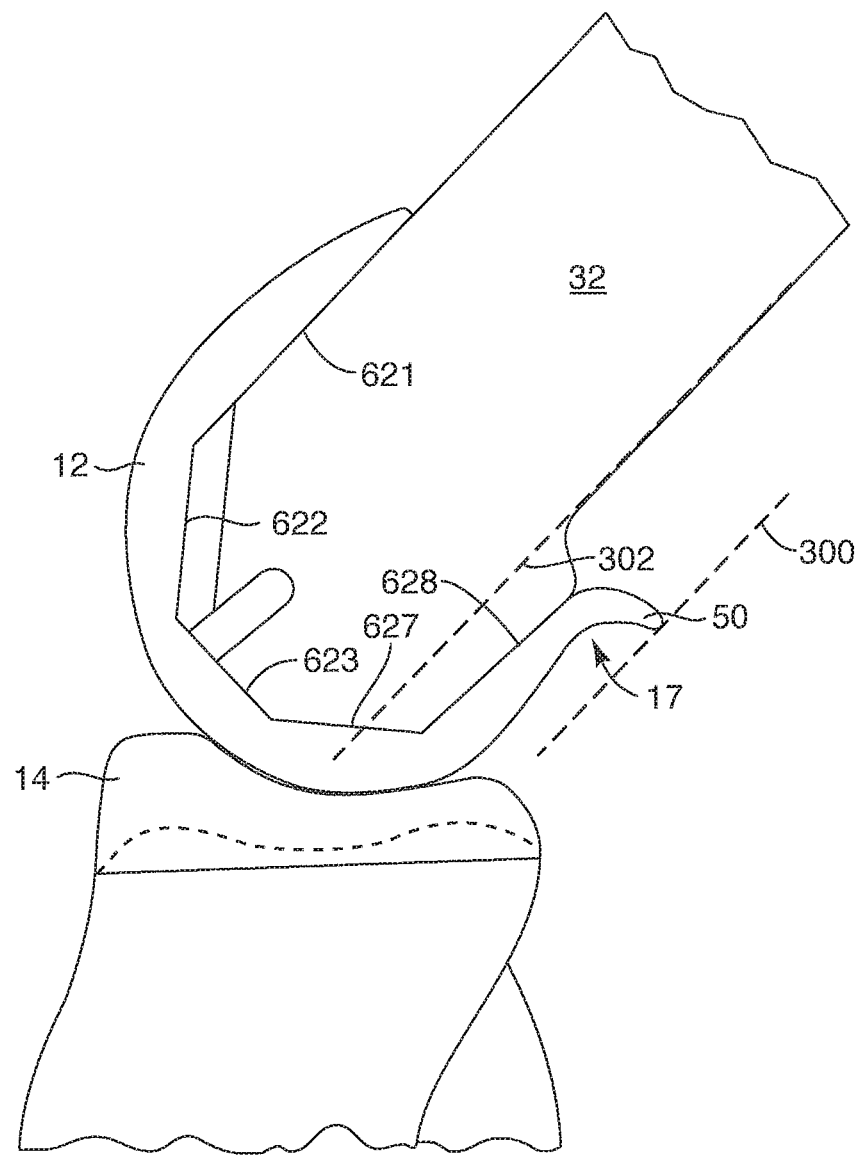
FIGS. 16X-16Z illustrate flexion of a non-limiting embodiment of a femoral component having femoral full flexion articulation in accordance with a representative embodiment of the present invention.
Figure 16Y:
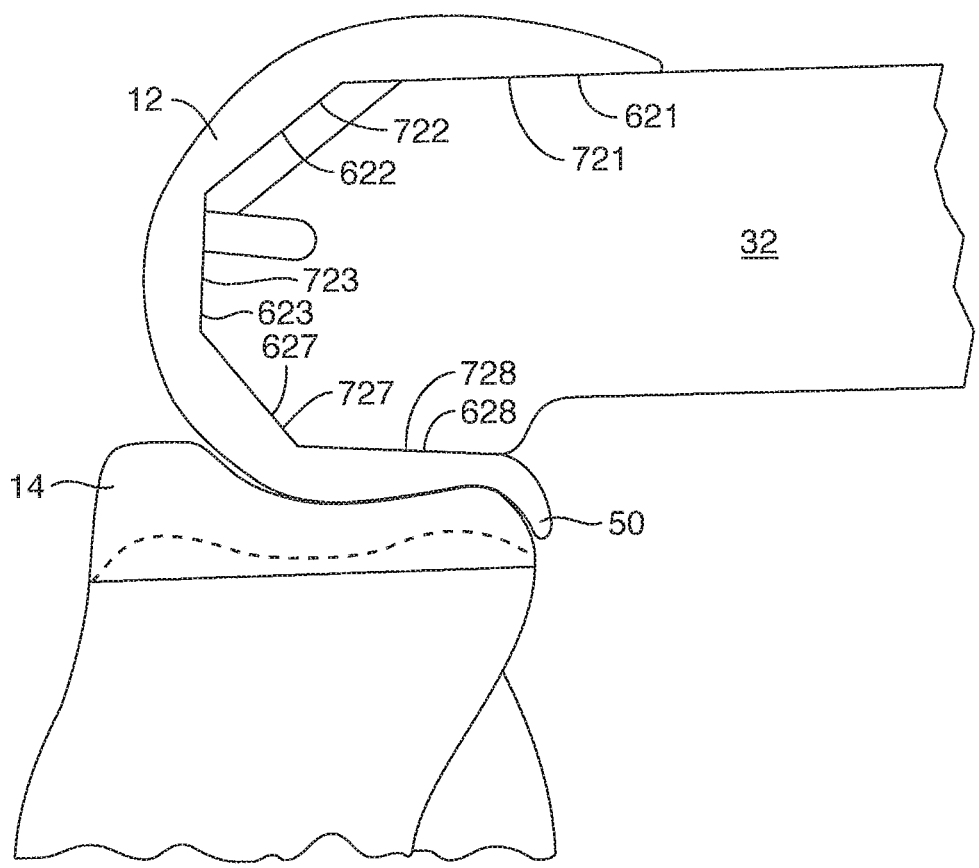
Figure 16Z:
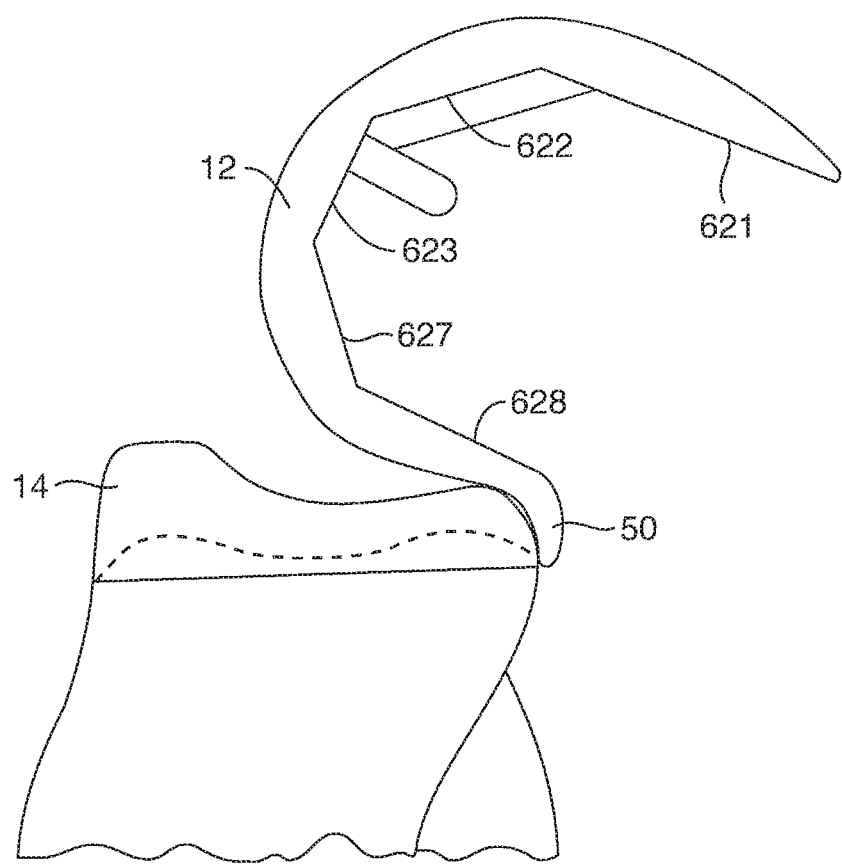

In other embodiments, FIGS. 16X-16Z show that, in some cases, the proximal extension 50 is disposed on a femoral component 12 that lacks a surface (e.g., surface 624) for contacting a full flexion cut 624 on the femur 32. In such embodiments, the proximal extension 50 can be disposed in any suitable location that allows it to perform its intended functions. Indeed, in some embodiments in which the femoral component 12 comprises a first internal surface 721 for contacting the anterior surface 621 of the femur 32, a second internal surface 722 for contacting an anterior chamfer cut 622 on the femur, a third internal surface 723 for contacting a distal cut 623 on the femur, a fourth internal surface 727 for contacting a posterior chamfer cut 627 on the femur, and an additional internal surface 728 for contacting a posterior condylar cut 628 on the femur (e.g., a cut that runs substantially parallel to, or that diverges by any suitable amount of less than about 50 degrees (e.g., any suitable amount less than 40 degrees) from the first interior surface 621), the proximal extension 50 is disposed proximal to surface 628.

Thus, FIGS. 16X-16Z show that conventional femoral components can easily be modified to include a femoral full flex articulation (e.g., by the addition of a modular and/or integral proximal extension 50). It should be noted that while FIGS. 16X-16Z show the femoral component 12 having a proximal extension 50 that is being used to articulate and/or act as a fulcrum against the tibial component 14 (e.g., a component comprising a tibial full flex articulation), such a femoral component can be used to articulate against an any suitable tibial articulation surface (e.g., from a unresected tibia, a partially resected tibia, and/or any suitable tibial component that can articulate with the proximal extension 50). Additionally, while FIGS. 16X-16Z show some embodiments in which the proximal extension is formed as an integral portion of the femoral components, in some embodiments (as described herein), the proximal extension comprises a modular unit that is attachable to the femoral component.

Thus, in some embodiments of the present invention, greater deep knee flexion is facilitated by providing an articular surface on the proximal posterior and/or anterior surfaces (or portions) of one or both of the posterior condyles of the femur. At least some such embodiments embrace an additional or increased articular surface on the proximal posterior and/or anterior portion (e.g., as shown in FIGS. 16A-16S and 16X-16Z) of either or both of the medial or lateral posterior condyles of the femoral component 12. Indeed, some embodiments of the femoral component 12 add increased articular surface area to the proximal end of the posterior condyles of the femoral component 12 (e.g., in an anterior direction such that when the patient bends his or her knee during deep knee or full functional flexion, contact between the femoral component 12 and the tibial component 14 is maintained, and a greater, deeper knee flexion may be achieved.

In at least some embodiments of the present invention, greater deep knee flexion may be provided or improved by modifying the tibial articulation, in which the center of the conforming medial tibial articular surface of the tibial component 14 is moved posterior relative to what is currently available. Additionally, in some such embodiments, the overall shape of the lateral and/or medial tibial articular surfaces may be modified. This is illustrated with reference to FIGS. 6A-6D and 6J-6K.

In some such embodiments of the tibial component 14, the condylar or articular plateau surfaces are asymmetric. Indeed, in some embodiments, the lateral undersurface side of the tibial component 14 is shorter in the anteroposterior dimension than the medial side, and the top of the tibial component 14 may also be asymmetric.

Anatomically, the tibial plateau typically has a greater anteroposterior dimension medially than it has laterally. In order to cover as much of the cut proximal tibia as possible and avoid anterior or posterior overhang of the lateral plateau, in some instances, the tibial component is larger in the anteroposterior dimension medially than it is laterally. In one embodiment, this is accomplished by moving the center of the medial articular surface posteriorly to compensate for the dimensional differences. In some cases, in order to achieve full flexion, it can be useful to have the medial center of rotation on the tibia (which is a concave segment of a sphere) more posterior than is currently available with other designs. This allows the proximal tibia, when the knee is flexed beyond approximately 120-130 degrees, to be positioned anteriorly enough so that there is no impingement of the posterior edge or portion of the medial tibial articular surface on the proximal portion of the posterior medial condyle of the femur. Current designs of tibial components 14, which will allow the tibia to move anterior with flexion, either have a non-spherical medial tibial articular surface or the center of rotation of the spherical articular surface is not as far posterior as is provided by the embodiments described below. However, embodiments of the current invention may be used in combination with any knee replacement design that will allow knee flexion to 120° or greater.

Currently, some available total knee tibial components 14 that have a fixed center of rotation medially, have the center of rotation located at a position that is around 35-45% of the entire anteroposterior dimension from the posterior surface of the tibial component 14. Nevertheless, in some embodiments of the tibial component 14 described herein, the center of rotation is moved posteriorly so that it is between about 18% and about 35% of the anteroposterior dimension from the posterior wall of the tibial component 14. In such embodiments, the center of rotation can be disposed in any location between about 18% and about 35% (or any sub-range thereof) of the anteroposterior dimension of the tibial component 14, as measured from the component's posterior edge. Indeed, in one non-limiting example, the center of rotation of the femur with respect to the tibial component is between about 20% and about 33% of the anteroposterior dimension from the posterior edge of the tibial component 14.

In the normal knee, the medial side of the knee is constrained in that for any degree of flexion the position of the medial femoral condyle relative to the tibial articular surface is roughly fixed and does not move anteriorly or posteriorly a significant amount in the flexion range of roughly 20-130 degrees. In contrast, on the lateral side, except for full extension and sometimes full flexion, after around 20-40 degrees of flexion the lateral femoral condyle can move anterior and posterior on the lateral tibial plateau. In full functional flexion to 160 degrees and beyond, the lateral femoral condyle may appear to be touching only the most posterior portion of the opposing tibial plateau or it may contact the plateau more anterior clearly on the flattened portion of the lateral tibial plateau.

Therefore, in embodiments of the tibial component 14, the lateral tibial articular surface is basically flat in the anteroposterior sense, except anteriorly where there is an anterior lip which prevents the tibial component from rotating too far externally and allowing the lateral femoral condyle to slide off the anterior edge of the tibial component. In some embodiments, the basically flat portion of the lateral tibial articular surface may comprise between about two-thirds and about seven-eighths (or any sub-range thereof) of the total anteroposterior dimension of the tibial component 14. In some embodiments, a slight lip may be present posteriorly on the lateral side, however, as long as the fixed center of rotation is positioned as described, no lip is required posteriorly on the lateral side. In other embodiments there is no anterior or posterior lip. In some embodiments, the lateral tibial articular surface is either flat or concave when viewed in the frontal plane and, if concave, may or may not be the same radius of curvature of the opposing femoral condyle or it may have a greater radius when viewed in the frontal plane. In some cases, this flat or concave groove is flat on the bottom when viewed in the sagittal plane, except for the anterior and posterior ends as noted above and is generated around a point that corresponds to the center of rotation of the medial condyle. In some embodiments, the posterolateral tibial articulation may be the same as described for the medial posterior full flex articulation. In other embodiments, the medial tibial articular surface may be the same as, or similar to the flat articular surface described for the lateral tibial plateau. However, in some embodiments, the position of the medial articular contact is mainly obligatory while the position of the lateral articular contact is non-obligatory. Thus, the position of the lateral articular contact is likely determined by the task being performed, by comfort, and/or by culture.

Figure 6A:
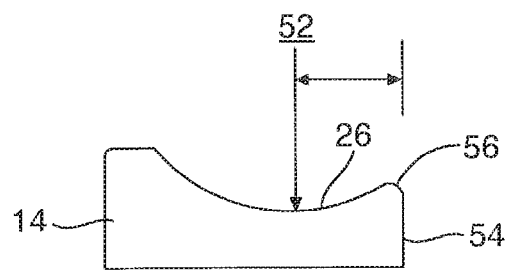
FIGS. 6A-6B depict side views of a representative prior art tibial component of a knee prosthesis.
Figure 6B:
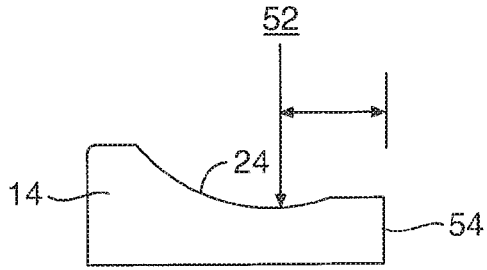
Figure 6C:
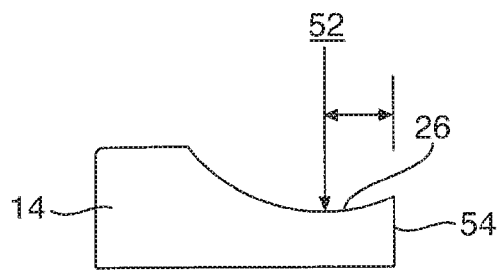
FIGS. 6C-6D depict side views of a representative embodiment of a tibial component in accordance with embodiments of the present invention.
Figure 6D:
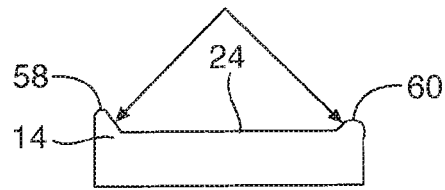
Figure 6J:
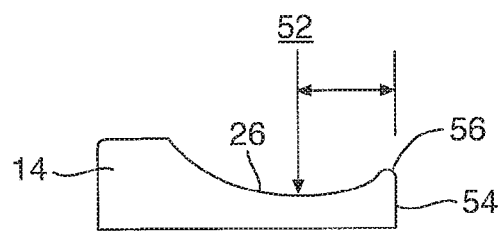
FIGS. 6J and 6K depict side views of a representative embodiment of a tibial component in accordance with embodiments of the present invention.
Figure 6K:
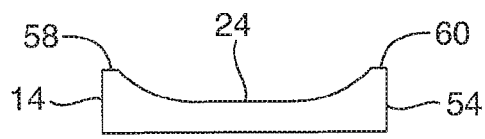

FIGS. 6A-6D and 6J-6K depict a comparison of a prior art tibial component 14's medial tibial condylar surface 26 and lateral tibial condylar surface 24 with some embodiments of the tibial component 14 as discussed above. Specifically, FIGS. 6A and 6B reflect side views of medial and lateral sides (respectively) of some currently available tibial components 14, while FIGS. 6C and 6J illustrate side views of medial sides, and FIGS. 6D and 6K illustrate side views of lateral sides of some embodiments of the tibial component 14, as discussed above. It will be appreciated that a number of varied configurations for the medial and lateral articular surfaces ranging from almost flat, both medially and laterally, to more conforming, as shown in FIGS. 6A and 6B, have been used in the past; however, it is currently believed that none have either a combination of a posteriorly-displaced medial articular surface and a relatively-flat lateral articular surface, or a medial femoral full flex tibial articulation. These configurations permit the lateral femoral condyle to move anteriorly and posteriorly on the lateral tibial articular surface as the knee flexes and extends. Other configurations may be provided, so that as long as the lateral tibial articular surface will allow this anteroposterior motion, the lateral tibial configuration does not need to be confined to a single configuration, as shown in FIGS. 6D and 6J.

The lateral tibial articulation may in some embodiments have no posterior lip, and in other embodiments the posterior surface may slope downward when it is accompanied by a medial tibial articulation that provides for flexion beyond 135 degrees.

In the prior art tibial component 14, the condylar surface has a curvature centered on a fixed point 52. The distance from the fixed point 52 (or from the low point of the curvature centered on the fixed point 52) to the posterior edge 54 of the tibial component is approximately 35-45% of the anteroposterior dimension of the tibial component 14. These measurements are similar for the medial (FIG. 6A) and lateral (FIG. 6B) sides of the tibial component 14. Some currently available tibial components 14 have a lip 56.

In the embodiment of the tibial component 14 illustrated in FIGS. 6C and 6D, there is no tibial component lip 56 associated with the medial condylar surface 26. Rather, the medial tibial condylar surface 26 runs along a smooth arc. As the arc is generated, a low lip may be present in some embodiments and may extend up to and include the tibial full flex posterior articulation. The amount of the lip will be determined by the relationship of the center of rotation to the posterior edge 54 of the tibial component 14. In another embodiment, however, FIG. 6J shows an implementation in which the tibial component 14 (e.g., at the medial tibial condylar surface 26) comprises a lip 56 at the end of a smooth arc.

Though the radius from fixed point 52 to the articular surface in FIGS. 6A and 6C is essentially the same, in some embodiments of the current invention, the distance from the fixed point 52 (or from the low point of the curvature centered on the fixed point 52) to the posterior edge 54 of the tibial component 14 is shorter. Indeed, as mentioned earlier, in some embodiments, the fixed point 52 is disposed at any location between (or sub-range of) approximately 18% and less than approximately 35% of the anteroposterior dimension from the posterior end of the tibial component 14, as may be seen in FIGS. 6C and 6J. For instance, in some non-limiting embodiments of the current invention, the distance from the fixed point 52 to the posterior edge 54 of the tibial component 14 is between about 20% and about 30% (e.g., about 28%±1.5%).

With respect to the lateral side of the tibial component 14, in the embodiment illustrated in FIGS. 6D and 6K, there is both an anterior lip 58 and a small posterior lip 60. In alternate embodiments, the posterior lip 60 may be omitted as discussed above. Additionally, with respect to FIG. 6J, in some embodiments, the posterior lip 56 can raise any suitable amount above the lowest point (e.g., fixed point 52) in the tibial articulation surface (e.g., medial tibial condylar surface 26). Indeed, in some embodiments, the posterior lip rises between about 0.5 and about 8 mm (or any sub-range thereof) above the lowest point in the medial tibial condylar surface 26. Indeed, in some embodiments, the posterior lip rises between about 2 and about 6 mm (or any sub-range thereof) above the lowest point in the medial tibial condylar surface 26. Moreover, in some embodiments, the posterior lip rises between about 3 and about 5 mm (or any sub-range thereof) above the lowest point in the medial tibial condylar surface 26.

Thus, as has been illustrated with reference to FIGS. 6A-6D and 6J-6K, in at least some embodiments of the present invention, greater deep knee flexion may be provided or improved by modifying the tibial articulation, in which the center of the conforming medial tibial articular surface of the tibial component 14 is moved posterior relative to what is currently available. This change alone, with some currently-available femoral components, will increase the amount of flexion achieved when compared to a standard tibial component. Additionally, in some such embodiments, the overall shape of the lateral tibial articular surface is modified. While such modification can be used for any suitable purpose, in some embodiments, the lateral tibial articular surface is modified to allow the proximal tibia, when the knee is flexed beyond approximately 120-130 degrees, to be positioned anteriorly enough so that there is no impingement of the posterior edge or portion of the medial tibial articular surface on the proximal portion of the medial condyle of the femur. Therefore, greater deep knee flexion may be achieved. It can thus be appreciated that the use of an embodiment of the above tibial component with a conventional femoral component will facilitate greater flexion than will the use of a conventional tibial component. Similarly, the use of any of the above-described femoral components with a conventional tibial component will facilitate more flexion than will use of a conventional tibial component with a standard femoral component.

One having skill in the art will appreciate that the knee may (as discussed above) include at least one of a lateral pivot and a medial pivot. Accordingly, the embodiments of the present invention will be understood to be compatible with either or both of the lateral and medial knee pivot configurations. In other words, while several embodiments described above discuss the lateral tibial articular surface 24 and the medial tibial articular surface 26 as having specific characteristics, in some embodiments, the placement of one or more of the aforementioned characteristics of the lateral tibial articular surface and the medial tibial articular surface are reversed. In this regard, the placement of each of the characteristics discussed above can be reversed in any suitable manner that allows the lateral tibial articular surface (or lateral tibial condylar surface) to comprise a fixed center of rotation and that allows the medial tibial articular surface (or medial tibial condylar surface) to allow the medial femoral condyle to move anteriorly and posteriorly on a medial tibial plateau of the tibial component 14. By way of non-limiting illustration, in some instances, FIGS. 6C and 6J illustrate portions of various tibial components 14 comprising a lateral tibial condylar surface (e.g., surface 26), while FIGS. 6D and 6K illustrate portions of various tibial components 14 that include the medial tibial condylar surface (e.g., surface 24).

In some embodiments of the present invention, greater deep knee flexion may be provided or improved by modifying tibial articulation, in which the articulated surface of the tibial component is modified to encourage or limit articulation of the femoral component relative to the tibial component. Examples of such modification are shown in FIGS. 6E-6I.

Figure 6E:
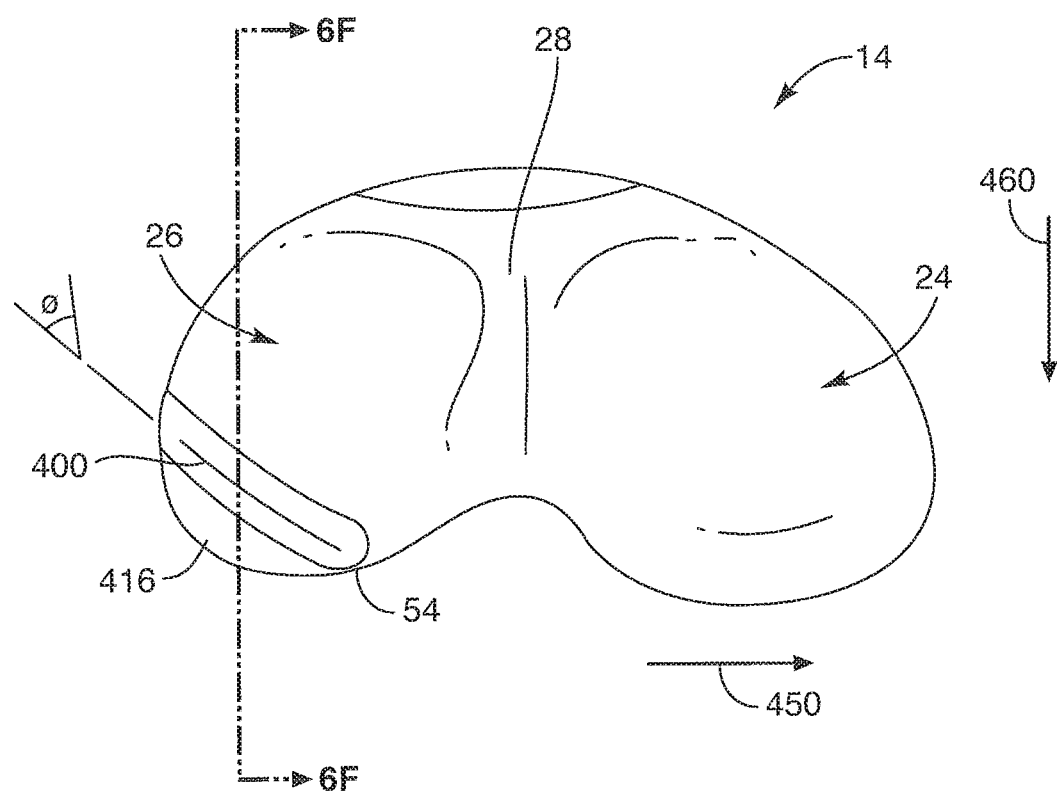
FIGS. 6E-6F depict an alternate embodiment of a representative tibial component modified to include a raised ridge articulation feature.
Figure 6F:
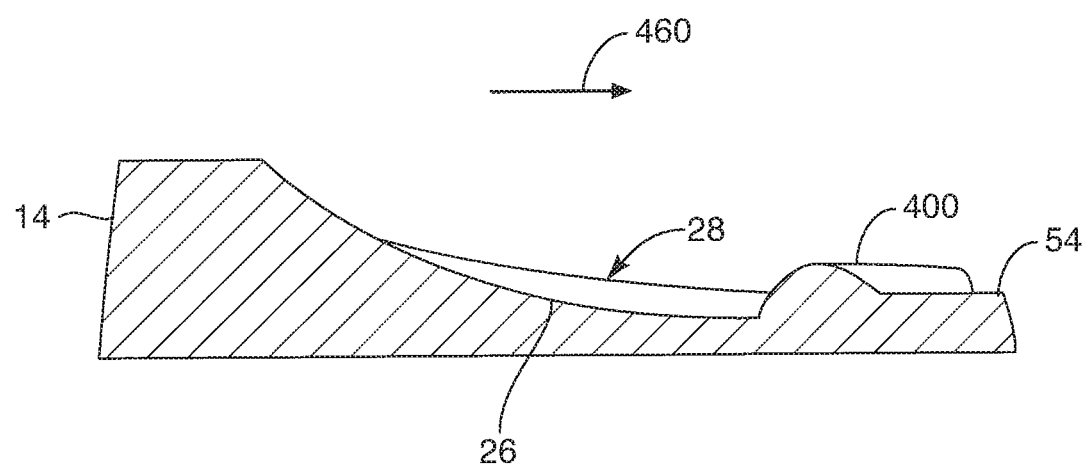

Referring now to FIGS. 6E, 6F, and 6I, a tibial component 14 is shown in accordance with a representative embodiment of the present invention. In some embodiments, the medial tibial condylar surface 26 of the tibial component 14 is modified to include an articulation feature. An articulation feature is generally provided to compatibly interact with an opposing articulation surface of the femoral component. During flexion of the knee, the articulation surface of the femoral component interacts with the articulation feature of the medial tibial condylar surface to guide or direct the articular movement of the femoral component relative to the tibial component. Thus, in some embodiments, an articulation feature is provided to control articulation of the knee during deep flexion.

Various types of articulation features may be used in accordance with the teaching of the present invention. For example, some embodiments of the articulation feature comprise an angled articular ridge 400. The articular ridge 400 is provided to compatibly interact with an opposing articular surface of the femoral component. The interaction between the articular ridge 400 and the articular surface of the femoral component affects a change in the articular movement of the femoral component during deep flexion of the knee. Indeed, in some embodiments, an interaction between the femoral component and the articular ridge 400 causes the posterior articulation of femoral component to shift when deep flexion is achieved. Additionally, in some embodiments, the articulation feature acts as the tibial full flex articulation.

The articular ridge 400 is generally disposed on the posterior surface of the tibial component 14 in a general medial-lateral direction 450. While the articular ridge can generally be disposed at any suitable angle with respect to an anteroposterior direction 460 of the intercondylar surface 28, in some embodiments, the articular ridge 400 is disposed or positioned on the posterior surface at an angle θ that is obtuse to an anteroposterior direction 460 of the intercondylar surface 28. In other embodiments, however, the articular ridge 400 is disposed or positioned on the posterior surface at an angle θ that is acute to an anteroposterior direction 460 of the intercondylar surface 28. Generally, angle θ of the articular ridge 400 is selected so as to achieve a desired articular shift of the femoral component during deep flexion. In some embodiments, an angle θ of approximately 0° to approximately 110° is selected. In some other embodiments, an angle θ of approximately 0° to approximately 90° is selected. In yet other embodiments, an angle θ of approximately 10° to approximately 45° is selected. Additionally, in some embodiments, an angle θ of approximately 20° to approximately 35° is preferred. In still other embodiments, the angle θ falls in any suitable sub-range of the aforementioned ranges. By way of illustration, FIG. 6E illustrates an embodiment in which the articular ridge 400 runs at an acute angle to the anteroposterior direction 460 of the intercondylar surface 28. Additionally, FIG. 6I illustrates an embodiment in which the articular ridge 400 runs substantially perpendicular to the anteroposterior direction 460 of the intercondylar surface 28.

The articular ridge 400 can have any suitable shape that allows the tibial component 14 to articulate against an articular surface of a femur and/or femoral component 12. Indeed, while some embodiments of the articular ridge are substantially straight along their length, in other embodiments, the articular ridge comprises an elongated ridge that is slightly bowed (as shown in FIG. 6E), that is curved along a portion of its length, that follows a contour of a posterior edge of the lateral articular surface 24, that follows a contour of a posterior edge of the medial articular surface 26 (as shown in FIG. 6I), that has a bent portion, and/or that is otherwise shaped to causes the posterior articulation of the femoral component to shift on the tibial component when deep flexion is achieved.

The articular ridge 400 may be positioned anywhere on the articular surface of the tibial component 14 so as to achieve a desired articular shift of the femoral component during deep flexion of the knee. For example, in some embodiments, the lateral tibial condylar surface 24 is modified to include the articular ridge (not shown). In this example, any suitable amount of the articular ridge (or another articulation feature) can be disposed within the lateral half (or completely within the lateral condylar surface) of the tibial component 14. Indeed, in some embodiments, the articular ridge (or other articulation feature) is disposed at the lateral half (e.g., lateral to a central axis of the intercondylar surface 28) and does not extend into the medial half of the tibial component (at least not as a single continuous articular ridge).

In other embodiments, the medial tibial condylar surface 26 includes the articulation feature. In such embodiments, any suitable amount of the articular ridge (or another articulation feature) can be disposed within the medial half (or completely within the medial condylar surface) of the tibial component 14. Indeed, in some embodiments, the articular ridge (or other articulation feature) is disposed at the medial half (e.g., medial to a central axis of the intercondylar surface 28) and does not extend into the lateral half of the tibial component (at least not as a single continuous articular ridge). By way of illustration, FIG. 6E shows a representative embodiment in which the articular ridge 400 is disposed completely within the medial condylar surface 26.

In still other embodiments, both the medial and lateral tibial condylar surfaces 26 and 24 include an articular ridge 400 (or other articulation feature). Although in some such embodiments, a single articular ridge spans between both the lateral and the medial condylar surfaces, in other embodiments, the lateral and the medial condylar surfaces each comprise a separate articular ridge (and/or other articulation feature).

In some embodiments, the articulation feature comprises a polyethylene coating or layer. In other embodiments, the polyethylene coating is strictly applied to the articular ridge 400 and precluded from extending beyond articular ridge 400 so as to impinge on the femur during flexion.

Figure 6G:
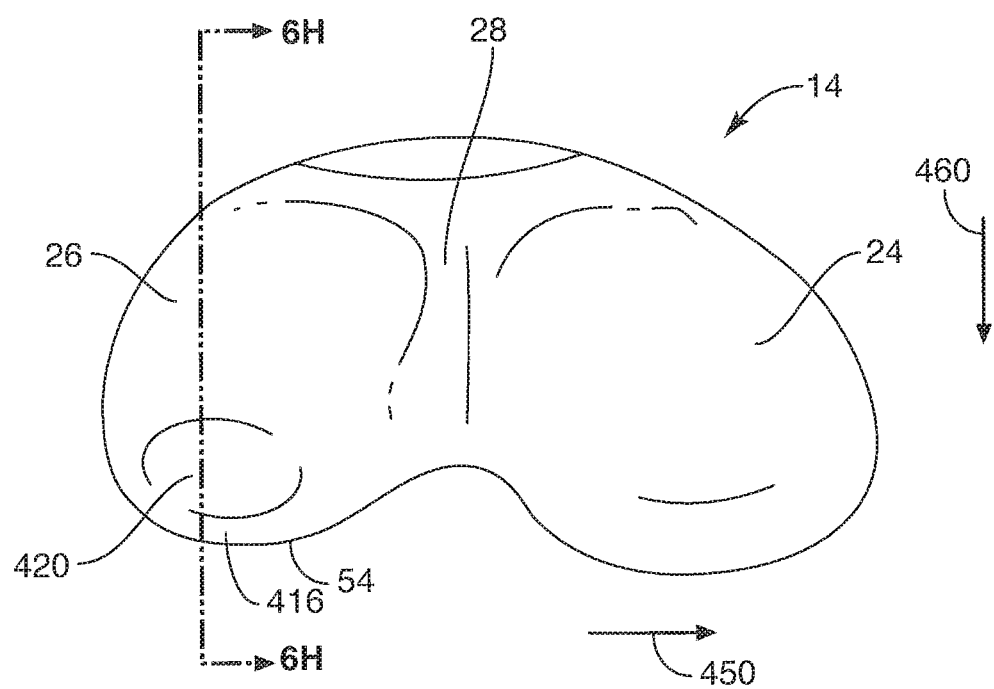
FIGS. 6G-6H depict an alternate embodiment of a representative tibial component modified to include a spherical articulation feature.
Figure 6H:
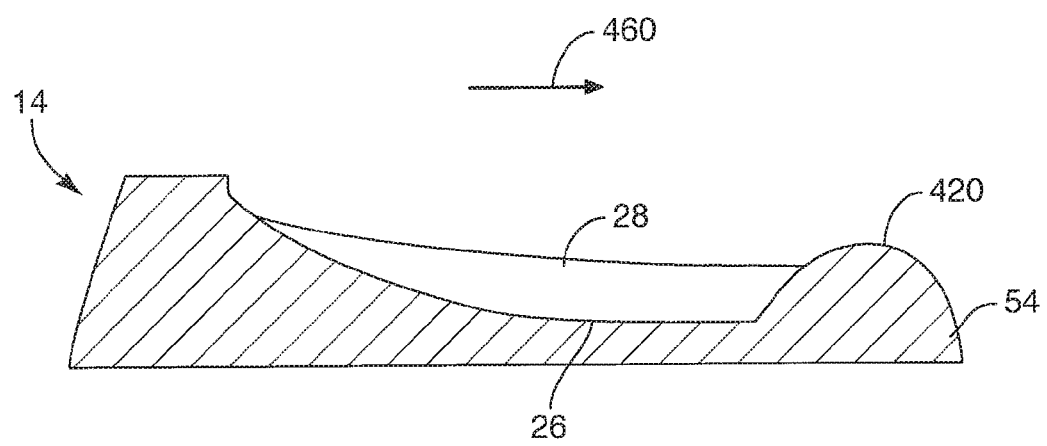
Figure 61:
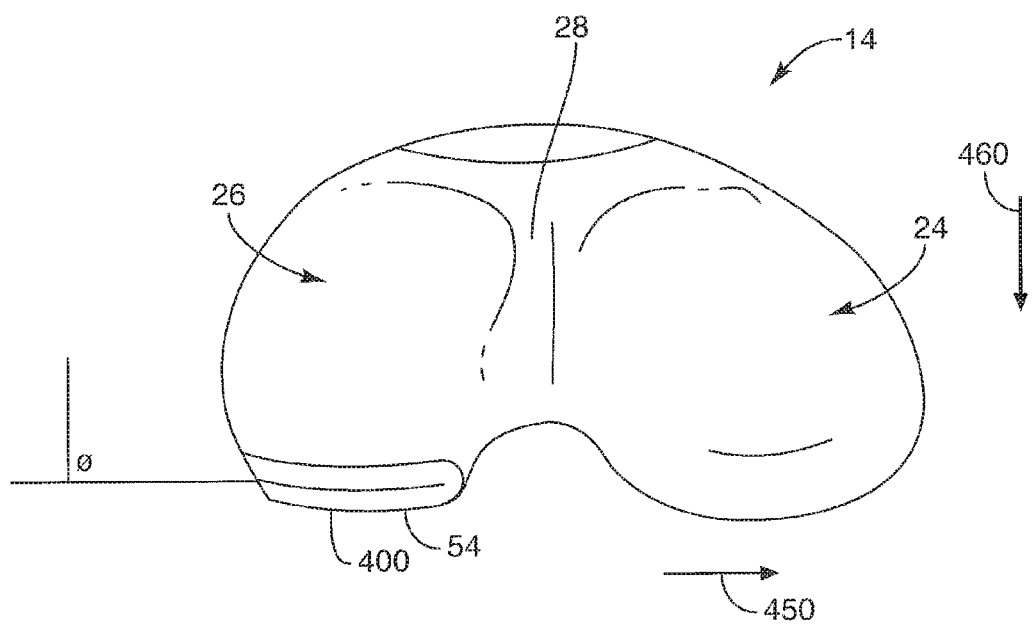

Referring now to FIGS. 6G and 6H, a tibial component 14 is shown in accordance with a representative embodiment of the present invention. In some embodiments, the medial tibial condylar surface 26 of the tibial component 14 is further modified to include an articulation feature comprising a spherical articular surface 420. The spherical articular surface 420 is provided to compatibly interact with an opposing articular surface of the femoral component. In some embodiments, the interaction between the spherical articular surface 420 and the articular surface of the femoral component enables unrestricted, natural, articular movement of the femoral component during deep flexion of the knee. In some embodiments, an interaction between the femoral component and the spherical articular surface 420 permits a natural posterior articulation of the femoral component when deep flexion is achieved. One of ordinary skill in the art will appreciate that the tibial component 14 may also be modified to permit femoral articulation on the lateral tibial condylar surface of the tibial component. Additionally, one of ordinary skill in the art will appreciate that the tibial component 14 may be modified to permit concomitant femoral articulation on both the medial and lateral tibial condylar surfaces of the tibial component, for desired applications.

The spherical articular surface 420 may comprise a true spherical shape, or may comprise any other suitable shape, including, without limitation, a parabolic shape; a protuberance; a convex shape; a rounded, raised bump; a raised, polygonal shape; a raised elliptical shape; a raised irregular shape; and/or any other suitable shape that projects from an articular surface of the tibial component (and/or tibia). One of skill in the art will appreciate that variations in the surface structure of the articular surface 420 may be required to provide an articular surface that is optimally configured for a specific application or use.

The spherical articular surface 420 may be positioned anywhere on the articular surface of the tibial component so as to achieve a desired natural movement to the femoral component during deep flexion of the knee. Indeed, in some embodiments, the lateral tibial condylar surface 24 is modified to include the spherical articular surface (not shown). In such embodiments, any suitable amount of the spherical articular surface can be disposed within the lateral half (or completely within the lateral condylar surface) of the tibial component 14. Indeed, in some embodiments, the spherical articular surface is disposed at the lateral half (e.g., lateral to a central axis of the intercondylar surface 28) and does not extend into the medial half of the tibial component (at least not as a single, continuous spherical articulation surface).

In other embodiments, the medial tibial condylar surface 26 includes the spherical articular surface (or articulation feature). In such embodiments, any suitable amount of the spherical articular surface can be disposed within the medial half (or completely within the medial condylar surface) of the tibial component 14. Indeed, in some embodiments, the spherical articular surface is disposed at the medial half (e.g., medial to a central axis of the intercondylar surface 28) and does not extend into the lateral half of the tibial component (at least not as a single continuous articular ridge). By way of illustration, FIG. 6G shows a representative embodiment in which the spherical articular surface 420 is disposed completely within the medial condylar surface 26.

In other embodiments, both the medial and lateral tibial condylar surfaces 26 and 24 include a spherical articular surface 420. Although in some such embodiments, a single spherical articular surface spans between both the lateral 24 and the medial 26 condylar surfaces, in other embodiments, the lateral and the medial condylar surfaces each comprise a separate spherical articular surface (and/or other articulation feature).

In some embodiments, the articulation feature comprises a polyethylene coating or layer. In other embodiments, the polyethylene coating is strictly applied to the spherical articular surface 420 and precluded from extending beyond spherical articular surface 420 so as to impinge on the femur during flexion.

Additionally, while the articulation feature (e.g., articular ridge 400, spherical articular surface 420, etc.) is disposed at posteriorly on the tibial component 14 (and/or on a tibial articular surface), the articulation feature can be disposed in any suitable location with respect to the posterior edge of the tibial component (and/or tibial articular surface). Indeed, while in some embodiments, the articular feature is disposed at and/or extends to the posterior edge of the tibial component, in some other embodiments, the articular feature terminates (or lowers in elevation) anterior to the posterior edge. Indeed, (as shown in FIGS. 6G, 6E, and 6F) in some embodiments, a substantially flat, concave, and/or raised articulation surface 416 is disposed between a posterior portion of the articulation feature (e.g., spherical articular surface 400 and/or spherical articular surface 420) and the posterior edge of the tibial component 14.

Where the tibial component 14 comprises a unicompartmental component, the articulation feature (e.g., the articular ridge 400, spherical articular surface 420, etc.) can be disposed in any suitable location on the unicompartmental component. Indeed, while in some embodiments, the articulation feature is simply disposed within the confines of the unicompartmental component (e.g., the lateral or medial unicompartmental component), in other embodiments, the articulation feature is disposed within the articular surface (e.g., the medial tibial condylar surface 26 or the lateral tibial condylar surface 24) of the unicompartmental component.

In some embodiments, the opposing surface of the femur and/or femoral component is modified to comprise a concave surface (not shown) configured to compatibly interface with the convex, spherical articular surface 420 of the tibial component. In other embodiments, the opposing surface of the femur and/or femoral component is modified to include a concave groove (not shown) configured to compatibly interface with the convex, articular ridge 400 of the tibial component. Further, in some embodiments the tibial component comprises a concave surface (not shown) and the femoral component comprises a convex surface (not shown) to compatibly interact with the tibial concave surface. Still further, in some embodiments the polyethylene coating (not shown) or the articular surface of the tibial component is configured to compatibly interface with a desired structure, shape or feature of the opposing femoral surface, thereby achieving normal knee function and movement throughout the knee's range of motion. For example, in some embodiments a tibial component is provided without an elevated, posterior portion or articulation feature. Rather, the surgeon may elect to leave the posterior portion of the patient's tibia which in turn interfaces with the femoral component to achieve normal knee function. Thus, in some embodiments a unicompartmental tibial component is provided to achieve normal knee function.

Figure 7A:
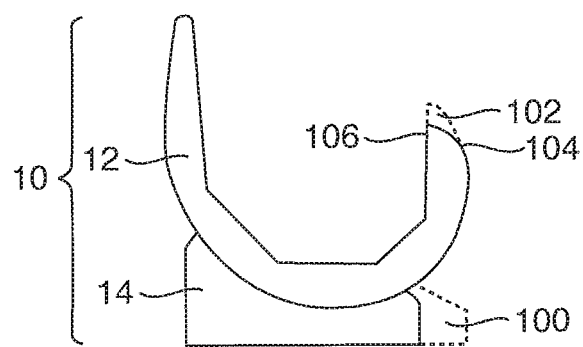
FIGS. 7A and 7B depict alternate embodiments of femoral and tibial components in accordance with embodiments of the present invention.
Figure 7B:
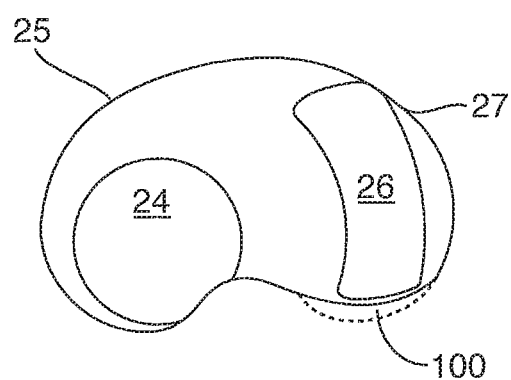

FIGS. 7A and 7B depict modifications to the femoral component 12 and the tibial component 14 to enable deeper knee flexion. Specifically, FIG. 7A depicts a sagittal sectional view of a knee prosthesis 10 with a modified femoral component 12 and tibial component 14. In FIG. 7A an area 102 of the femoral component 12 is removed, as represented by the dashed line. This area 102 is above and between the posterior extreme 104 and the anterior side 106 of the posterior extreme 104. By removing the area 102, deeper flexion for prosthetic knee patients is partially achievable.

Similarly, with the tibial component 14 in FIG. 7B, a medial side 25 may appear to be relatively lengthened in the anteroposterior dimension anteriorly by moving the articular surface 24 posterior and thereby having more of the tibial component anterior to the posteriorly-displaced medial articulation. This may give the appearance of having removed a posterior portion of the tibial component 14 and moved it to the anterior. A lateral side 27 of the tibial component may be shortened in the anteroposterior dimension relative to the medial side 25 (i.e., area 100). FIG. 7B illustrates the foregoing in plan view. In other words, by posteriorly shortening the lateral side 27 (i.e., by removing area 100) of the tibial component 14 and by displacing the medial articular surface 24 more posterior, deeper knee flexion is possible. And, these modifications create the opportunity for a prosthetic knee patient to achieve a deeper knee flexion than possible with currently-available prosthetic knees.

Figure 17:
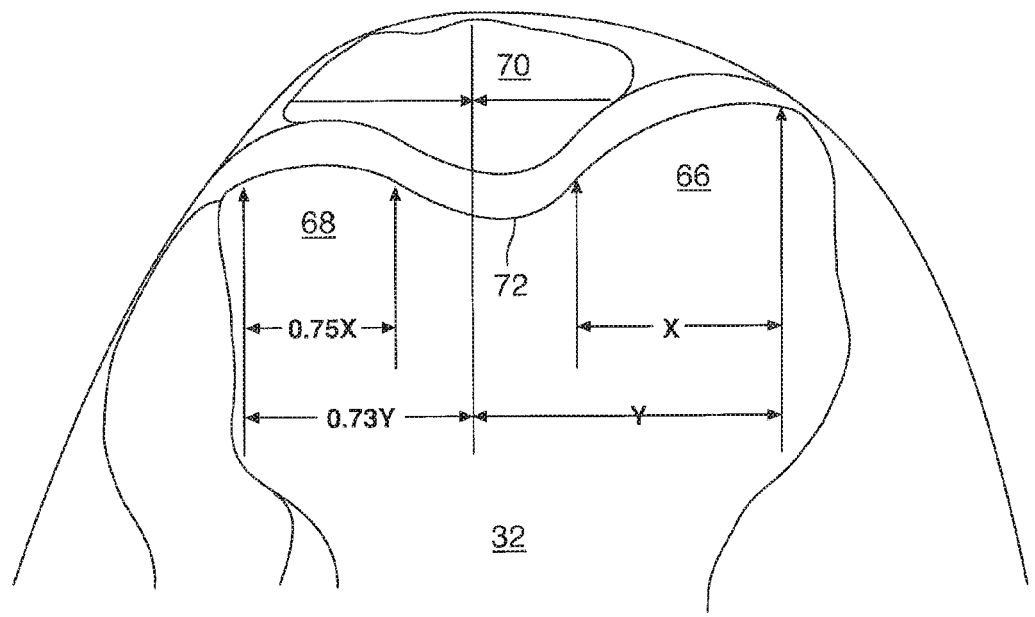
FIG. 17 illustrates drawing of a radiograph of a normal knee flexed to approximately 160 degrees, and further illustrating the position of the patella.

In at least some embodiments of the invention, greater deep knee flexion can be achieved by providing an asymmetrical femoral component 12. The asymmetrical femoral component 12 permits transfer of more than one-half of the force transmitted across the joint to be transmitted to the medial side, as occurs in the normal knee. Some such embodiments are illustrated with reference to FIGS. 17 and 18A. FIG. 17 illustrates a drawing from a radiograph of a knee at about 160-degree flexion. In the radiograph, the femur 32 is viewed in the anteroposterior direction, and a medial condyle 66 of the femur 32, a lateral condyle 68 of the femur 32, and a patella 70 are visible. As may be appreciated by reference to the Figure, the medial-lateral width of the articulating portion of the medial condyle 66 is larger than the medial-lateral width of the lateral condyle 68. Specifically, in the Figure, the medial-lateral width of the articular portion of the medial condyle 66 is represented by X. As may be seen in the Figure, in some embodiments, the medial-lateral width of the lateral condyle 68 is approximately 75% (or any suitable amount less) of the medial-lateral width X of the medial condyle 66. Indeed, in some embodiments, the medial-lateral width of the lateral condyle 68 is any suitable amount between about 10% and about 75% of the medial-lateral width X of the medial condyle 66. In still other embodiments, the medial-lateral width of the lateral condyle 68 is any suitable amount between about 30% and about 74% of the medial-lateral width X of the medial condyle 66. In yet other embodiments, the medial-lateral width of the lateral condyle 68 is any suitable amount between about 40% and about 70% of the medial-lateral width X of the medial condyle 66.

As may also be appreciated by reference to FIG. 17, the center of the patella 70 is lateral to the midline of the knee. Specifically, in the Figure the medial-lateral distance between the most medial portion of the distal end of the femur 32 and the center of the patella 70 is represented by Y. As may be seen, the corresponding medial-lateral distance between the most lateral portion of the distal end of the femur 32 and the center of the patella 70 is approximately 75% or less (73% in the Figure) of Y. In some embodiments of the invention, the femoral component 12 may mimic the actual physical structure of the knee represented in FIG. 17.

Figure 18A:
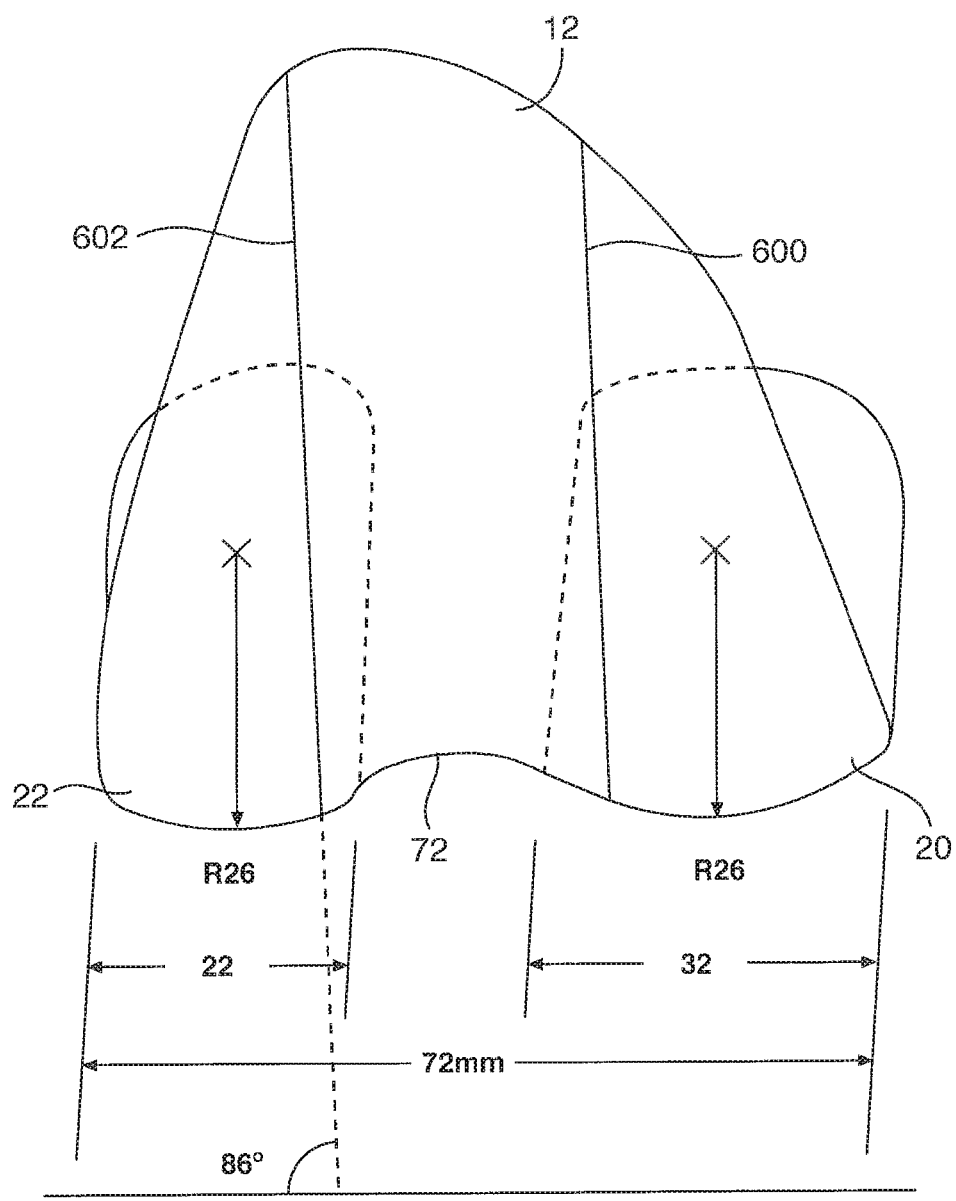
FIGS. 18A through 18C illustrate alternate embodiments of a femoral component in accordance with representative embodiments of the present invention.

In such embodiments of the femoral component as illustrated in FIG. 18A, the articular portion of the lateral condyle is, in its medial-lateral width, 75% or less than the width of the medial condyle. This allows for more than one half of the force that is transmitted across the joint to be transmitted to the medial side, which is what occurs in the normal knee. It also allows the patellar or trochlear groove to be lateralized because this groove distally is defined by its position between the medial and lateral condyles. In the normal knee the patella tends to be slightly lateralized on the femur and this lateral displacement of the groove accomplishes what many conventional total knee replacements accomplish by externally rotating the femoral component 12 in the total knee replacement. In one embodiment the condyles in the frontal plane are seen to be circular with a constant radius. The medial and lateral condyles do not need to be the same radius, but may both be circular when viewed in that plane. When viewed in the sagittal plane the condyles will be seen to have a closing radius posteriorly and anteriorly may blend into the anterior flange in the embodiments where an anterior flange is used.

FIG. 18A illustrates a front view of one embodiment of a femoral component 12 in accordance with the described embodiments. In the Figure, illustrative measurements are illustrated to show features of the described embodiment, and are not meant to be limiting of the features of the described embodiments. As shown in FIG. 18A, the total medial-lateral width of the femoral component 12 may be approximately 72 millimeters (mm). In this embodiment, the medial-lateral width of the medial femoral condylar surface 20 in the posterior portion of the medial posterior condyle is approximately 32 mm, while the medial-lateral width of the lateral femoral condylar surface 22 is approximately 22 mm. Thus, in the illustrated embodiment, the medial-lateral width of the lateral femoral condylar surface 22 is approximately 69% of the medial-lateral width of the medial femoral condylar surface 20.

In the illustrated embodiment, a patellar groove 72 is defined by the space between the medial femoral condylar surface 20 and the lateral femoral condylar surface 22. Because the medial-lateral width of the medial femoral condylar surface 20 is larger than the medial-lateral width of the lateral femoral condylar surface 22, the patellar groove 72 is displaced laterally, which is what occurs in the normal knee. As may be appreciated by reference to FIGS. 18A through 18C, the patellar groove 72 may be provided at an angle as the patellar groove 72 moves from a most proximal anterior portion to a distal anterior portion to a distal posterior portion and to a proximal posterior portion. For example, the angle of the patellar groove 72 in FIG. 18A, as measured from a sagittal plane is approximately 86 degrees. In other embodiments, however, the angle of the patellar groove can be any suitable angle that is less than about 90 degrees and about greater than about 15 degrees (or any sub-range thereof). Indeed, in some embodiments, the patellar groove extends laterally from a distal anterior portion of the femoral component to proximal-most, anterior portion of the femoral component at any suitable angle between about 40 degrees and about 89 degrees. In still other embodiments, the patellar groove extends at any suitable angle between about 50 and about 85 degrees.

Thus, the illustrated embodiment shows how a femoral component 12 in accordance with embodiments of the present invention may assist in achieving deeper knee flexion and, in some embodiments, full functional flexion, by providing an asymmetric femoral component 12. The asymmetric femoral component 12 may assist in achieving deeper knee flexion by better simulating physiologic loading and patellar tracking. The asymmetric femoral component 12 allows for more normal loading of the joint with the medial side taking more of the load than the lateral side. Additionally, the asymmetrical femoral component 12 allows for more anatomically correct lateral tracking of the patella which may decrease problems of patellar pain, subluxation, and dislocation. One of skill in the art will readily recognize that in some embodiments the tibial component 14 may be modified to accommodate an asymmetric femoral component 12.

As discussed herein, at least some embodiments of the present invention embrace providing deeper knee flexion capabilities where the medial femoral side stays relatively fixed and the lateral side glides forwards and backwards. While some embodiments embrace a knee with a tibial component that keeps the femoral component relatively fixed on the medial side and able to glide on the lateral side, other embodiments embrace a knee that is relatively fixed on the lateral side and able to glide on the medial side. This, for example, would apply to the tibial component.

Additionally, while the additional articular surface on the femoral component could be medial, lateral or both, at least some embodiments of the present invention embrace its application to use the tibial and femoral full flex articulations either medially, laterally, or both.

Figure 18B:
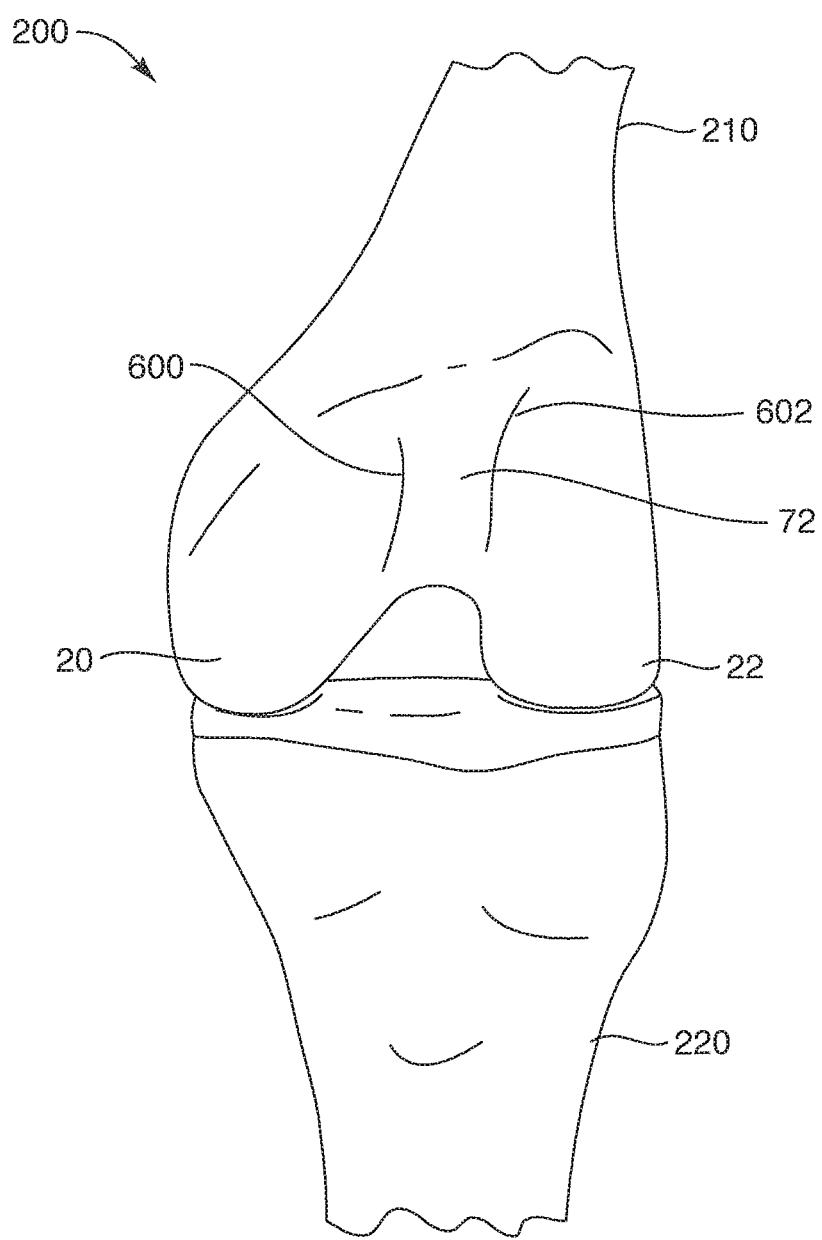
Figure 18C:
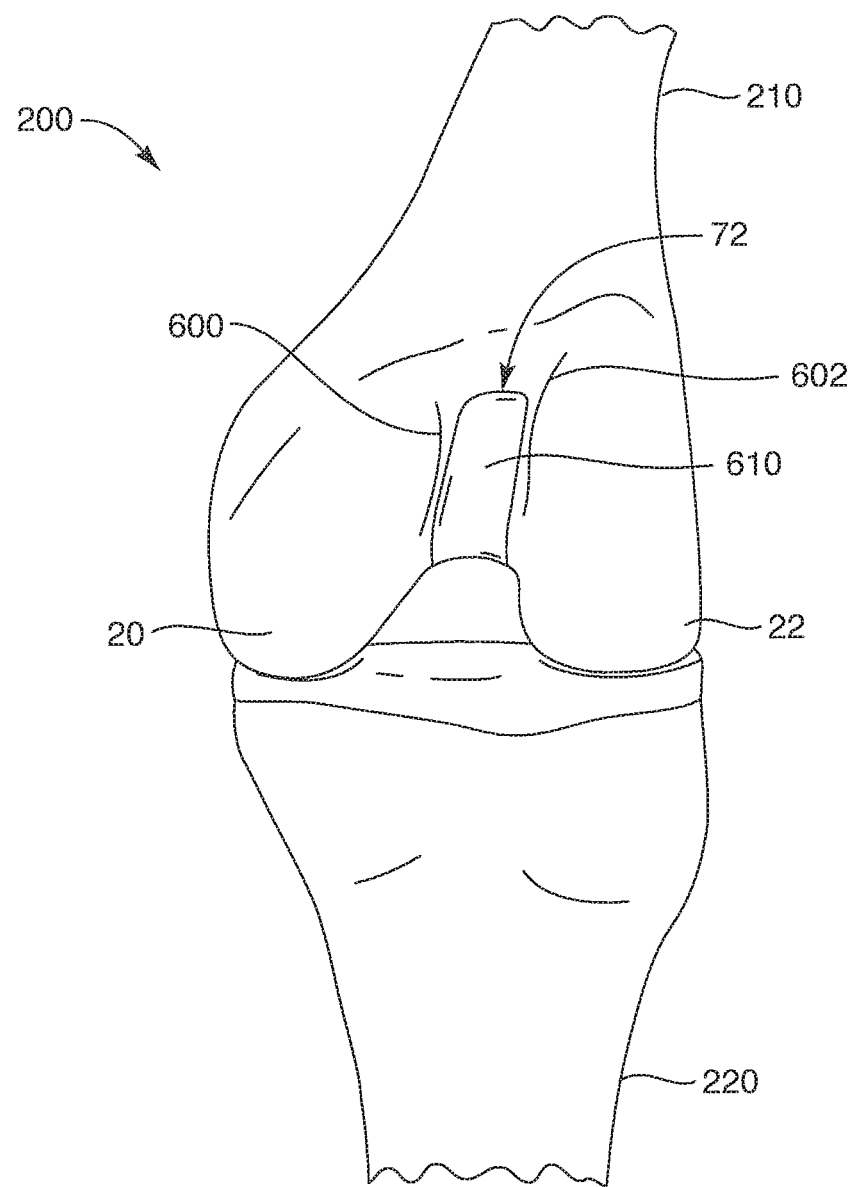

Referring now to FIGS. 18B and 18C, in some embodiments, an abbreviated anterior flange 610 is provided to replace the trochlear surface or groove 72. In some embodiments, articular cartilage and underlying bone is optionally removed, which is typically removed with the antero-distal chamfer cut. In some embodiments, anterior flange 610 is provided to compensate for individual patient anatomy where the lateral portion of the anterior condyle on a conventional prosthesis extends or sits more proud than the bony condyle of the knee 200. For these anatomies, the proud position of the conventional prosthesis tents or otherwise separates the lateral soft tissues which may result in decreased flexion and discomfort or pain. In some embodiments, anterior flange 610 is provided without replacing anterior condyles 20 and 22 of the distal femur 210, such as for use with a patient having severe patello-femoral arthritis that would not be adequately treated with the prosthesis shown in FIGS. 12A, 12B, 14 and 16Q through 16S. Providing only anterior flange 610 may also provide relief with reduced cost and/or reduced evasiveness. In other embodiments, anterior flange 610 is provided in addition to replacing the anterior condyles 20 and 22.

In some embodiments, the length of the abbreviated anterior flange 610 is very short so as to only replace a portion of the trochlear surface 72. In other embodiments, the length of anterior flange 610 is extended to entirely replace trochlear surface 72. Further, in some embodiments anterior flange 610 is extended distally between the distal condyles 20 and 22 to a length approximately equal to flanges of currently available, non-abbreviated prostheses.

Figure 21:
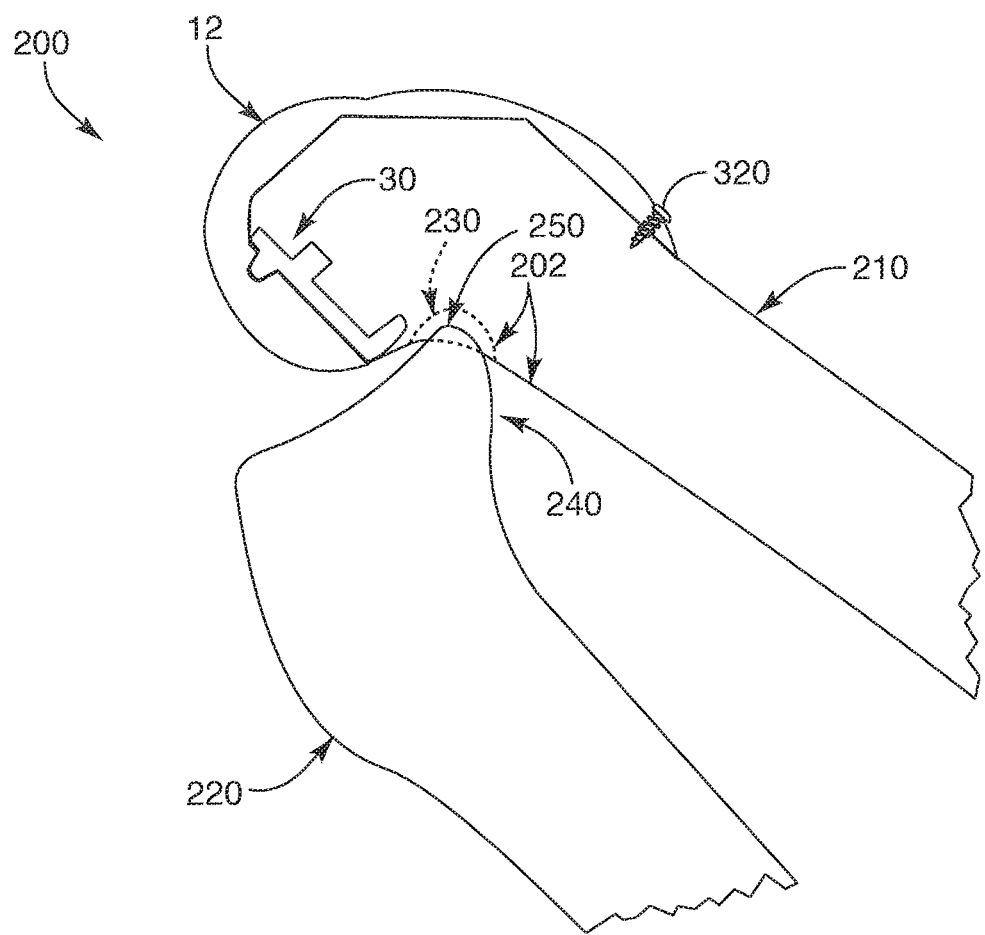
FIG. 21 illustrates a representative interaction of the posterior articulate surface of the medial plateau of the tibia and the popliteal surface during deep flexion of the knee.

Referring now to FIG. 21 a perspective side view of a knee 200 is shown. In at least some of the embodiments of the present invention, greater deep knee flexion may be further provided, improved, or enhanced by removing a portion of the popliteal surface 202 of the femur 210. The popliteal surface 202 may include bone proximal to the posterior articular surfaces of the medial condyle, the lateral condyle, or both the medial and lateral condyles. Resection of the popliteal surface 202 may be accomplished by any appropriate method known in the art. For example, in one embodiment a portion of the tibia is first resectioned thereby providing sufficient clearance to resect the necessary portion of the popliteal surface 230.

The amount of bone resected from the tibia, the femur or both will vary from individual to individual depending upon the specific anatomy of the tibia and the femur. The resectioned popliteal surface 230 provides additional clearance between opposing surfaces of the tibia 220 and the femur 210. Specifically, the resectioned popliteal surface 230 prevents an impingement of the posterior articulate surface 250 of the medial condyle 240 of the tibia 220 on the femur 210 during deep flexion of the knee 200. As such, the knee 200 may flex freely without the tibia 220 adversely binding on, or contacting any portion of the femur 210. Additionally, the resectioned popliteal surface 230 may provide flexion exceeding 140°. In one embodiment, the resectioned popliteal surface 230 provides flexion exceeding 160°.

Figure 22:
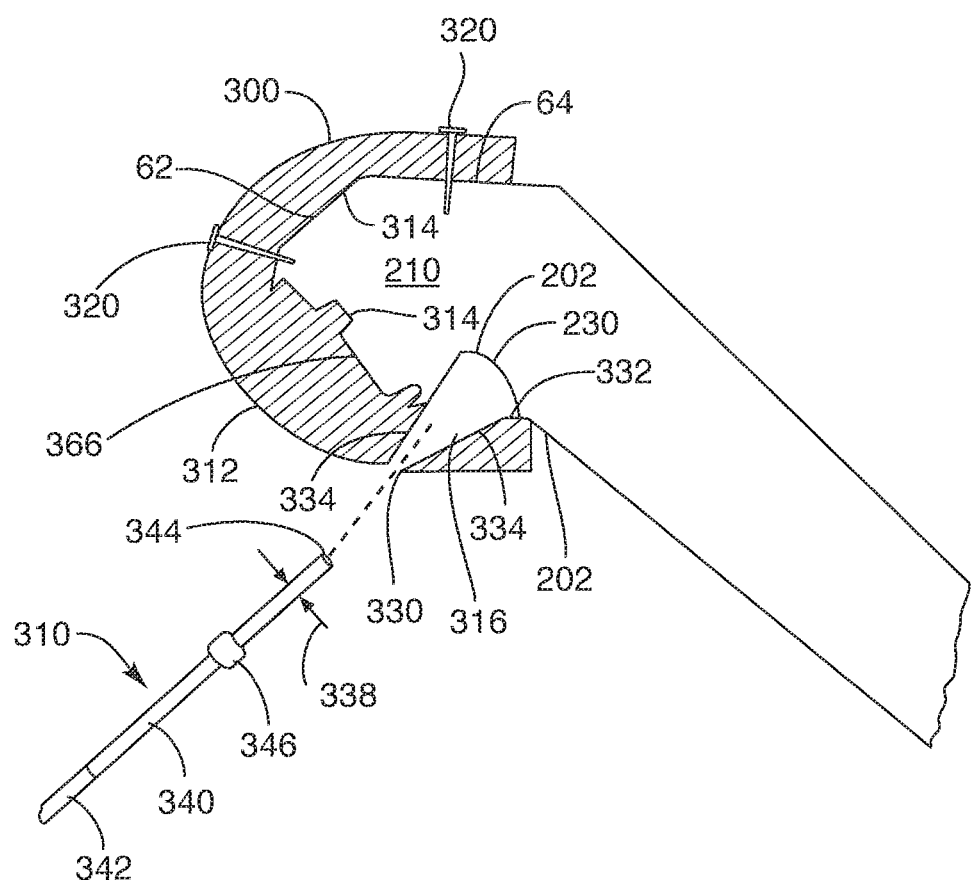
FIG. 22 illustrates a representative implementation of a resection block and the femur following resection of the popliteal surface.

Referring now to FIG. 22, a perspective side view of a knee 200 is shown following resection of the popliteal surface 202 to provide the resectioned surface 230. As previously discussed, resection of the popliteal surface 230 may be accomplished by any appropriate method known in the art. However, in one embodiment a resection block 300 is utilized to guide a cutting device 310 in making the resection 230. The resection block 300 is comprised of a metallic material, similar to the metallic materials previously discussed, and includes an outer surface 312, an inner surface 314, and a slot 316. The outer surface 312 is contoured and adapted to substantially overlap the lateral and medial condyles of the femur 210 however, in some embodiments, the guide would cover only the medial or lateral condyle. The inner surface 314 includes a plurality of angled surfaces that mirror the resectioned and shaped surfaces of the lateral and medial condyles of the femur 210. Thus, the inner surface 314 of the resection block 300 is adapted to compatibly engage the resectioned surfaces 62, 64, and 366 of the femur 210. The engaged resection block 300 and femur 210 are further secured via a plurality of fasteners 320, such as screws. This may not be necessary in all cases. The fasteners 320 are required only to firmly attach the guide to the femur. In some embodiments, the interaction between the guide and the femur is such that the guide is held firmly in place without fasteners. In another embodiment, the guide is held in place by any means to facilitate an accurate resection of the above mentioned area of the femur.

The interaction between the resection block 300 inner surface 314 and the resectioned surfaces 62, 64, and 366 of the femur 210 accurately aligns the slot 316 with the popliteal surface 202 of the femur 210. The slot 316 generally comprises an external opening 330 and an internal opening 332. The external opening 330 comprises a first width that is slightly greater than the width 338 of the cutting device 310. As such, the external opening 330 is adapted to compatibly receive the cutting device 310. The internal opening 332 is positioned exactly adjacent to the popliteal surface 202 and comprises a second width that is greater than the first width and approximately equal to the desired width of the popliteal resection 230. Thus, the walls 334 of the slot taper inwardly from the second opening to the first opening thereby providing a wedged slot 316.

The cutting device 310 may include any device compatible with the slot 316. In one embodiment an oscillating blade 340 is provided. The oscillating blade 340 includes a shank 342, a cutting head 344 and a stop 346. The shank 342 generally comprises a surface that is adapted to compatibly and securely engage a tool (not shown) capable of moving the blade 340 relative to the resection block 300 and femur 210. The cutting head 344 generally comprises a plurality of teeth suitable for removing the desired portions of the popliteal surface 202 to form the resection 230. The stop 346 generally comprises a ferule, a crimp, or some other feature that provides a point on the blade 340 that is wider than the first opening 330 of the slot 316. As such, the stop 346 is unable to enter the slot 316 thereby limiting the depth into which the blade 340 is permitted to enter the slot 316. Thus, the stop 346 acts as a depth gauge to control or limit the final depth of the popliteal resection 230. In one embodiment, the stop 346 further comprises a set screw whereby the stop 346 is loosened and repositioned on the blade 340 to change the depth into which the blade 340 is permitted to enter the slot 316. In another embodiment, the cutting device 310 is a burr bit having a stop 346 to limit the cutting depth of the burr.

Figure 22A:
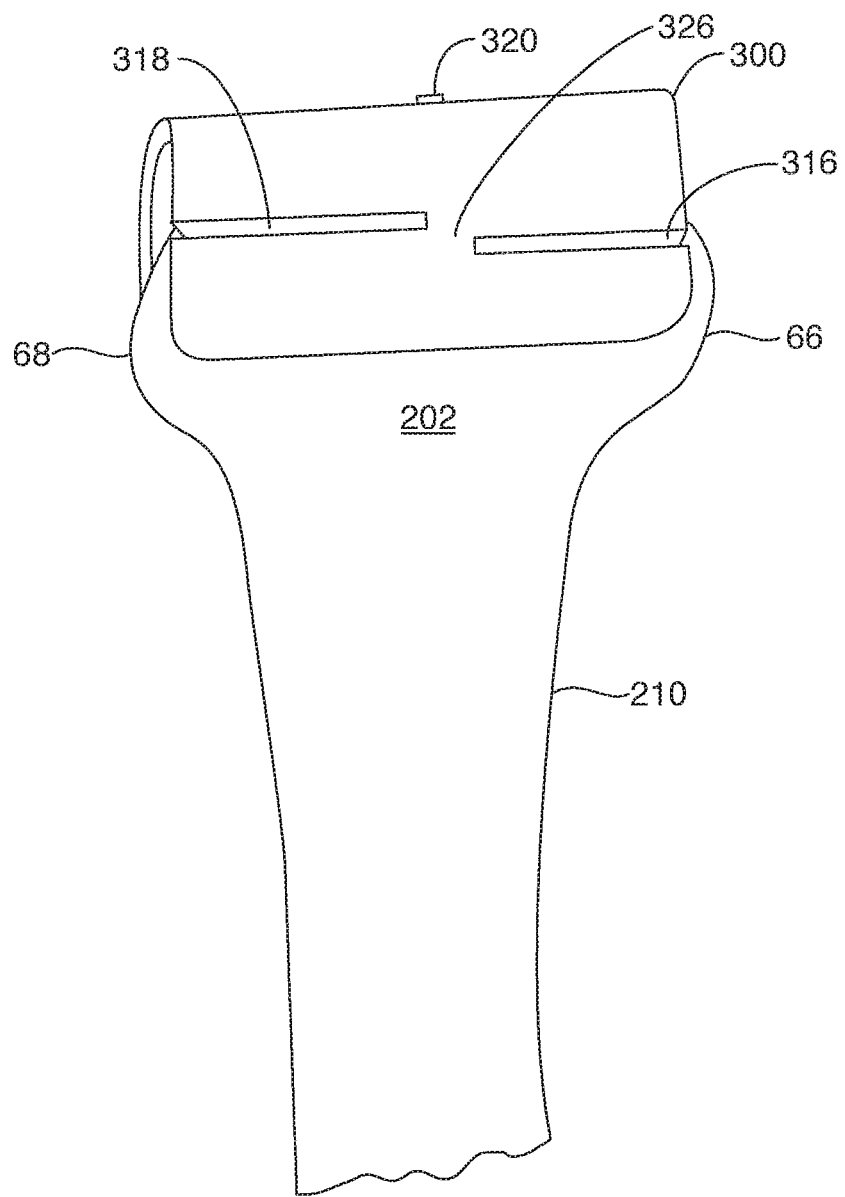
FIG. 22A illustrates a representative implementation of a resection block and the femur prior to resection of the popliteal surface.

Referring now to FIG. 22A, an underside, perspective view of the femur 210 and resection block 300 are shown. In one embodiment, the resection block 300 includes a first slot 316 and a second slot 318 separated by a connecting portion 326 of the resection block 300. The first slot 316 is positioned adjacent to the medial condyle 66 of the femur 210 and the second slot 318 is positioned adjacent to the lateral condyle 68. Each slot is positioned at a different height relative to the asymmetric, natural positions of the medial and lateral condyles 66 and 68. Thus, the first and second slots 316 and 318 of the resection block 300 are adapted to optimally resect the popliteal surface 202 of the femur 210 with respect to the asymmetric positions of the condyles 66 and 68. In another embodiment, the first and second slots 316 and 318 are positioned at equal heights so as to provide a resectioned popliteal surface 230 that is symmetrical without respect to the asymmetrical condyles 66 and 68. In yet another embodiment, the positioning of the external opening 330 relative to the internal opening 332 of the first slot 316 is different than the positioning of the external opening 330 relative to the internal opening 332 of the second slot 318. As such, the radius of each wedge opening 316 and 318 is different and the resultant contours or shapes of the resectioned popliteal surface 230 for the first and second slots 316 and 318 will be asymmetrical. In another embodiment, connecting portion 326 is eliminated thereby providing a single guide slot. In this embodiment, upper and lower portions of the guide are held in place relative to one another via lateral and medial bridges. The lateral and medial bridges maintain the position of the upper and lower portions of the guide, as well as define the outer edges of the slot. In another embodiment, lateral and medial bridges are used to provide multiple slots within the guide.

Referring now to FIGS. 22 and 22A, the popliteal resection 230 is made by inserting the cutting device 310 into the slot 316 and removing the popliteal surface 202 to the desired depth, as limited by the stop feature 346 and the radial limitations of the wedged slot 316. The wedged shape of the slot 316 permits the cutting device 310 to be pivoted along the radius of the wedge, wherein the contact between the stop 346 and the external opening 330 acts as a fulcrum for the radius of the wedge. The resultant resection 230 therefore comprises a radial surface configured and shaped to receive the femoral component 12 of the knee prosthesis. Following formation of the popliteal resection 230, the screws 320, or other stabilizing methods, and the resection block 300 are removed from the femur 210.

Figure 23:
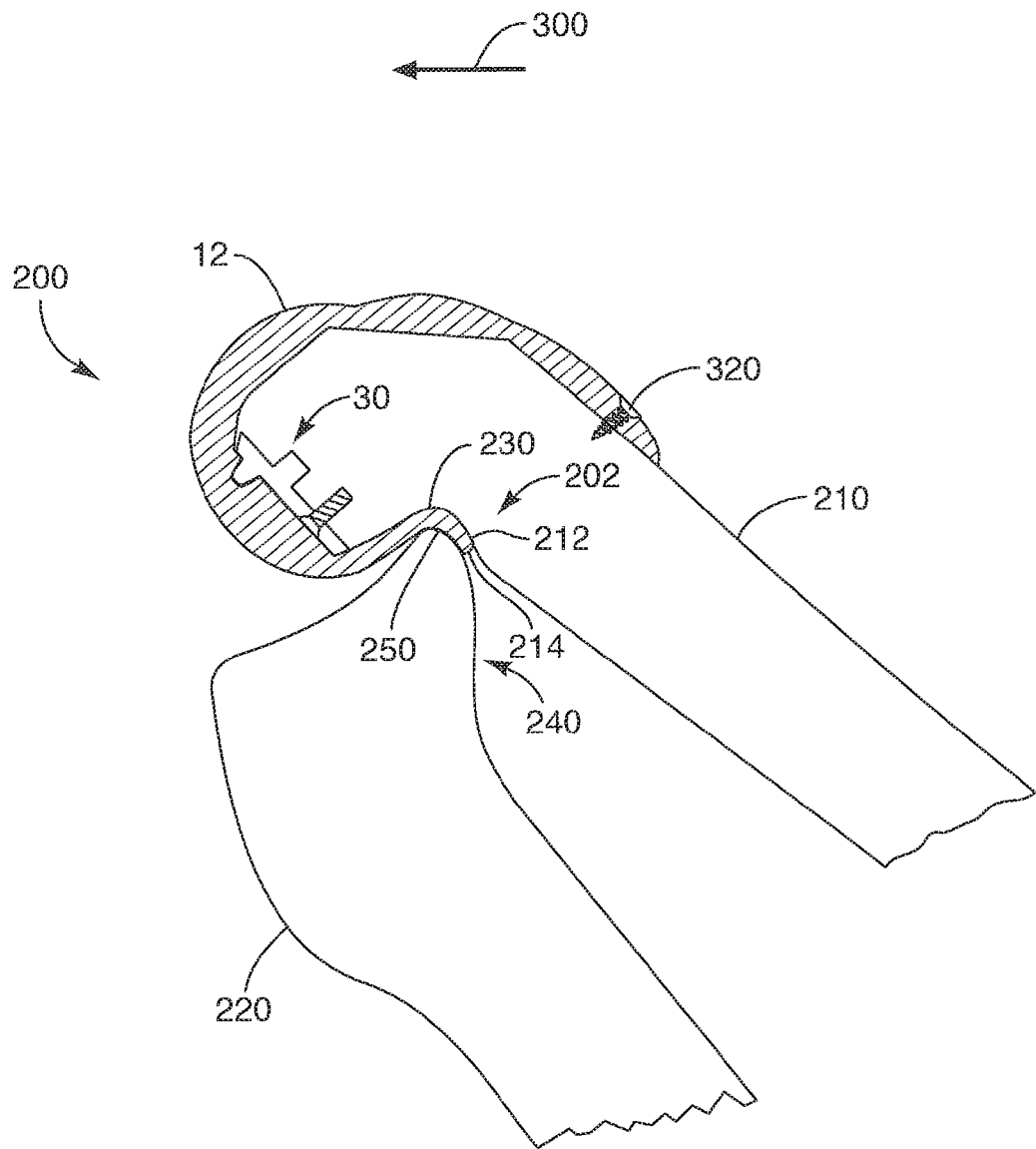
FIG. 23 illustrates a representative interaction of the posterior articular surface of the medial plateau of the tibia and an extended portion of the femoral component of the knee prosthesis during deep flexion.
Figure 23A:
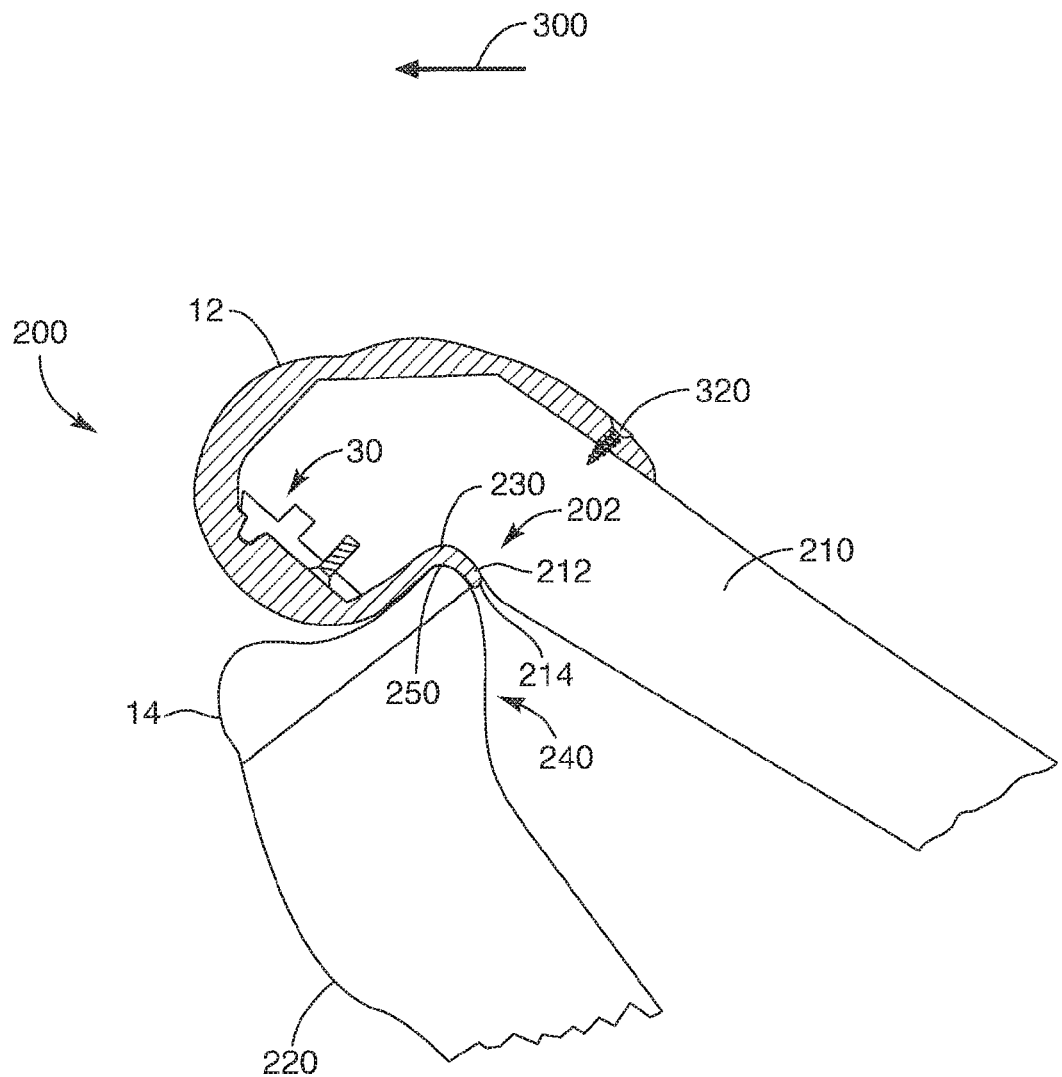
FIG. 23A illustrates a representative interaction of the posterior full flex articular surface of the medial tibial plateau of a tibial component and an extended portion of the femoral component of the knee prosthesis during deep flexion.

Referring now to FIGS. 23 and 23A, a cross-sectional side view of a knee 200 is shown following resection of the popliteal surface 230. The femoral component 12 of the knee prosthesis may be modified to correspond to the resectioned portion 230 of the popliteal surface 202. For example, in one embodiment a portion 212 of the femoral component 12 of the knee prosthesis is extended and contoured to seat within the resected portion 230 of the popliteal surface 202. As such, the posterior articular surface 250 of the medial plateau 240 of the tibia 220 compatibly and smoothly interacts with the extended portion 212 thereby further enabling the knee 200 to achieve deep flexion. Furthermore, the interaction between the posterior articulate surface 250 and extended portion 212 prevents the posterior articulate surface 250 from binding on a terminal surface 214 of the femoral component and displacing the femoral component 12 in an anterior direction during deep flexion. In some embodiments of the present invention, the extended portion 212 is used in conjunction with a tibial implant having a partial spherical or convex medial side. In another embodiment, the extended portion 212 is used in conjunction with any knee replacement that will allow knee flexion to 120° or greater. For example, in one embodiment a femoral component of a knee prosthesis system is modified to include a piece of metal up the back of the posterior portion of the component to provide an extended portion 212 compatible with the tibial component of the knee prosthesis system.

In some embodiments of the present invention including the extended portion 212, the femoral component 12 does not include an anterior flange or any provision for patella-femoral articulation anteriorly, as shown in FIGS. 15B and 16B (and 12B) above. As such, the lack of an anterior flange allows the component 12 to be impacted onto the femur in a relatively conventional manner, except that, in some embodiments, the component 12 is implanted after being rotated posteriorly relative to a conventional prosthesis. Additionally, the femoral component 12 can be used without a separate patella-femoral articular implant. In some embodiments, the component 12 is used with a modular flange attached to the proximal end of the anterior oblique condyle of the condylar implant to provide an anterior femoral articulation for the patella to prevent patellar subluxation and to be used in cases of patella alta. In another embodiment, the femoral component 12 is used with separate, unattached anterior patella-femoral implant articulations. In still other embodiments, a separate femoral flange is used for a patella that does not have an implanted component. In yet other embodiments (as shown in FIG. 15E), the femoral component 12 comprises a truncated anterior flange 213.

Where the femoral component 12 comprises a truncated anterior flange 213, the truncated anterior flange can extend any suitable distance (e.g., to any suitable distance between about 0 and about 15 mm) on either the proximal side or the distal side a proximal limit of the articular cartilage, which is a physiological marker that would be recognized by one of skill in the art). Similarly, in some embodiments in which the femoral component 12 comprises a truncated anterior flange 213, the truncated anterior flange can extend proximally any suitable amount past an anterior proximal end 71 of the anterior oblique cut 64 (and/or of the proximal limit of the articular cartilage) on a prepared femur 32 (e.g., between about 0 mm and about 15 mm, between about 1 mm and about 10 mm, as little as between about 2 mm and about 5 mm, or any suitable sub-range of the aforementioned distances).

In some embodiments, femoral component 12 further comprises a modular patella-femoral component 57 (or a modular anterior flange), as shown in FIG. 16T. Modular patella-femoral component 57 is generally configured to compatibly couple to femoral component 12 in an adjustable manner. For example, in some embodiments, modular patella-femoral component 57 comprises a post 59 which is sized and configured to slidably insert within a groove or socket 13 of femoral component 12. The slidable interaction between post 59 and socket 13 allows for infinite adjustment of modular patella-femoral component 57 with respect to femoral component 12, as shown in FIG. 16U.

The modular nature of femoral component 12 and patella-femoral component 57 provides customized fitting of the prosthesis to the patient. For example, in some embodiments, a patella-femoral component 57 is selected based upon an anatomical need or feature of the patient. In other embodiments, a femoral component 12 and a patella-femoral component 57 are selected based upon a mechanical need for this feature for the patient. Further, in some embodiments, a patella-femoral component 57 is selected to most accurately match a resectioned surface of the patient's femur. Accordingly, some embodiments of the present invention comprise a plurality of modular patella-femoral components 57 which are interchangeably coupled with femoral component 12 as may be required or desired to meet the needs of a patient.

The modular nature of femoral component 12 and patella-femoral component 57 further facilitates the fitting process of the knee prosthesis. For example, in some embodiments a structural configuration of a unitary femoral component may preclude installation or may require that additional bone be resectioned from the patient's femur to permit installation. Accordingly, some embodiments of the present invention provide a method for fitting a patient with the knee prosthesis, wherein the femoral component 12 of the knee prosthesis is initially fitted and secured to a resectioned surface of a patient's femur. The modular patella-femoral component 57 is then coupled or otherwise attached to the femoral component 12 and adjusted 61 to accommodate the specific anatomy of the patient. Once the position of modular patella-femoral component 57 is optimized, component 57 is secured to the patient's femur.

Referring now to FIG. 16V, a detailed view of an embodiment of socket 13 of femoral component 12 and post 59 of modular patella-femoral component 57 is shown. In some embodiments, socket 13 further comprises a tapered opening. Tapered opening 63 permits upward and downward adjustments 65 of modular patella-femoral component 57 relative to a fixed position of femoral component 12. In some embodiments, tapered opening 63 further permits lateral adjustments 67 of modular patella-femoral component 57 relative to a fixed position of femoral component 12. Thus, tapered opening 63 provides infinite adjustment of modular patella-femoral component 57 with respect to a fixed position of modular component 12. Further, in some embodiments, post 59 is tapered (not shown) thereby providing additional adjustment of modular patella-femoral component 57 with respect to femoral component 12, as may be desired.

In addition to the illustrated embodiments discussed above, the patella-femoral component 57 and the femoral component 12 can be modified in any suitable manner that allows the two components to be affixed to a femur 32. Indeed, in some embodiments, instead of including a post and socket coupling, the two components are coupled to each other through any other suitable manner, including, without limitation, through the use of a butt joint, a lap joint, a butt-lap joint, a rebated joint, a mortise and tenon, a dove-tail joint, a hinge, a flexible member, and any other suitable type of joint or combination of joints that allow the modular patella-femoral component 57 to be coupled to the femoral component 12.

In some embodiments, the patella-femoral component 57 and the femoral component 12 are coupled by a butt joint. While such a butt joint can have any suitable characteristic, in some embodiments, one of the components (e.g., the patella-femoral component 57 or the femoral component 12) comprises a convex surface, while the other (e.g., the femoral component 12 or the patella-femoral component 57) respectively comprises a concave surface. By way of illustration, FIG. 16W shows a representative embodiment in which the femoral component 12 comprises a convex surface 101 that couples with (i.e., abuts) a concave surface 103 of the patella-femoral component 57. In such embodiments, the rotatable interaction between the convex surface 101 and the concave surface 103 allows for virtually infinite adjustment of the modular patella-femoral component 57 with respect to the femoral component 12.

Where the patella-femoral component 57 and the femoral component 12 are coupled by a butt joint (or any other suitable joint), the surfaces between the patella-femoral component 57 and the femoral component 12 (e.g., the convex surface 101 and the concave surface 103) can have any suitable characteristic that allows the two components to be connected to each other. Indeed, while in some embodiments, the surfaces between the two components are smooth, in other embodiments, such surfaces are texturized to allow cement (or another adhesive) to bind tightly to the two components. While the surfaces between the components can be texturized in any suitable manner, in some embodiments, such surfaces are porous, roughened, knurled, comprise scaffolding, comprise ridges, comprise recesses, comprise protuberances, and/or are otherwise texturized to hold cement (i.e., any other suitable adhesive) and/or bone growth.

Referring now to FIG. 23A, a cross-sectional side view of a knee 200 is shown following resection of the popliteal surface 230, wherein the femoral component 12 is used in conjunction with a tibial component 14. In some embodiments of the present invention, the above described femoral component 12 is used in conjunction with a conventional tibial component 14 that does not have the tibial full flex articulation. For example, in one embodiment the above described femoral component 12 is used in conjunction with a tibial component 14 that has the center of the medial tibial articulation displaced posteriorly. In another embodiment, the femoral component 12 is used in conjunction with a tibial component 14 that has the center of the medial tibial articulation in a position that corresponds with currently available designs. In addition to occupying or lining the resectioned popliteal surface 230, the extended portion 212 may include additional features to modify the position of the tibia and the femur during full flexion.

For example, in one embodiment the extended portion 212 is modified to rotate the tibia relative to the femur with the knee in full flexion. In another embodiment, the extended portion 212 is modified to prevent rotation of the tibia relative to the femur with the knee in full flexion. In yet another embodiment, the extended portion 212 is modified to include a spherical surface on its upper or most proximal portion. As such, this spherical surface allows the tibia to rotate relative to the femur in full flexion. In some implementations of the present invention it may be desirable to have the spherical surface articulate with a corresponding concave surface in the femoral full flex articulation. Such a concavity would offer medial-lateral stability, provide area contact between the femoral and tibial components, and decrease polyethylene wear of the prosthesis. Referring again to FIG. 23, in some implementations of the present invention, the femoral component 12 is used in conjunction with a non-resected posterior portion of the patient's own tibial plateau to articulate with extended portion 212.

Figure 24:
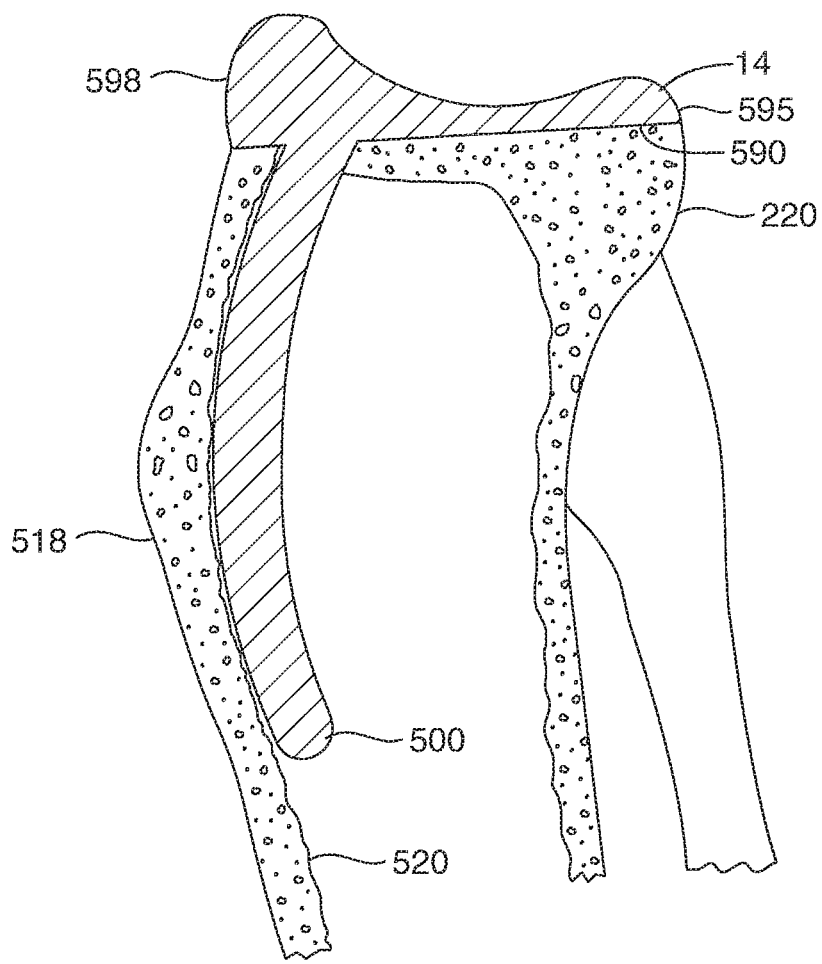
FIG. 24 illustrates a cross-section view of a tibial component and stem inserted within a tibia in accordance with a representative embodiment of the present invention.

Referring now to FIGS. 24 through 28, some embodiments of tibial component 14 are further modified to include a stem 500 generally attached to the anterior undersurface of tibial component 14. As shown in FIG. 24, anterior placement of stem 500 is calculated to compensate for and decrease the compressive load applied to the posterior tibia during flexion of the knee joint. In some embodiments, as compressive load is applied to the posterior tibia, stem 500 forms an interface with the inner surface 520 of the tibial anterior cortex 518 thereby preventing at least one of rotation, sinking, and/or subsidence of tibial component 14 relative to the tibia 220. Thus, the shape, size, angle, and placement of stem 500 are selected to achieve a desired interface between the stem 500 and inner surface 520.

Figure 25:
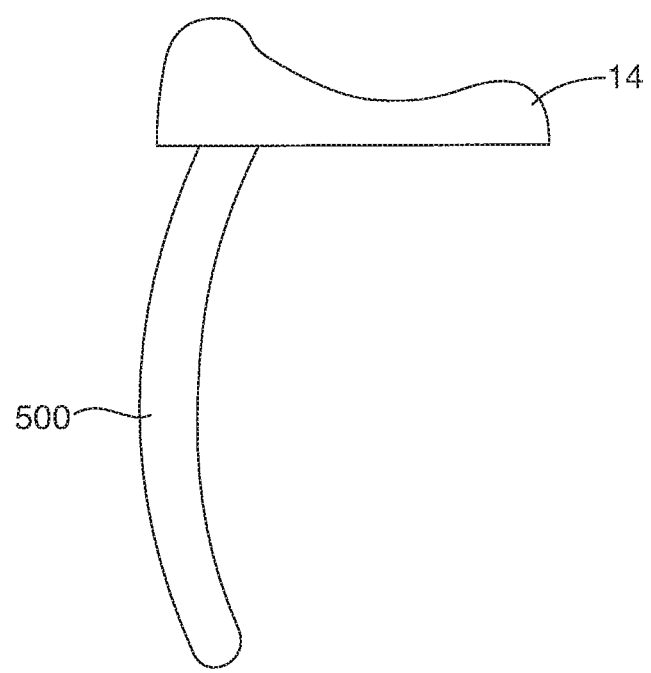
FIGS. 25-27 illustrate various embodiments of stems in accordance with representative embodiments of the present invention.
Figure 26:
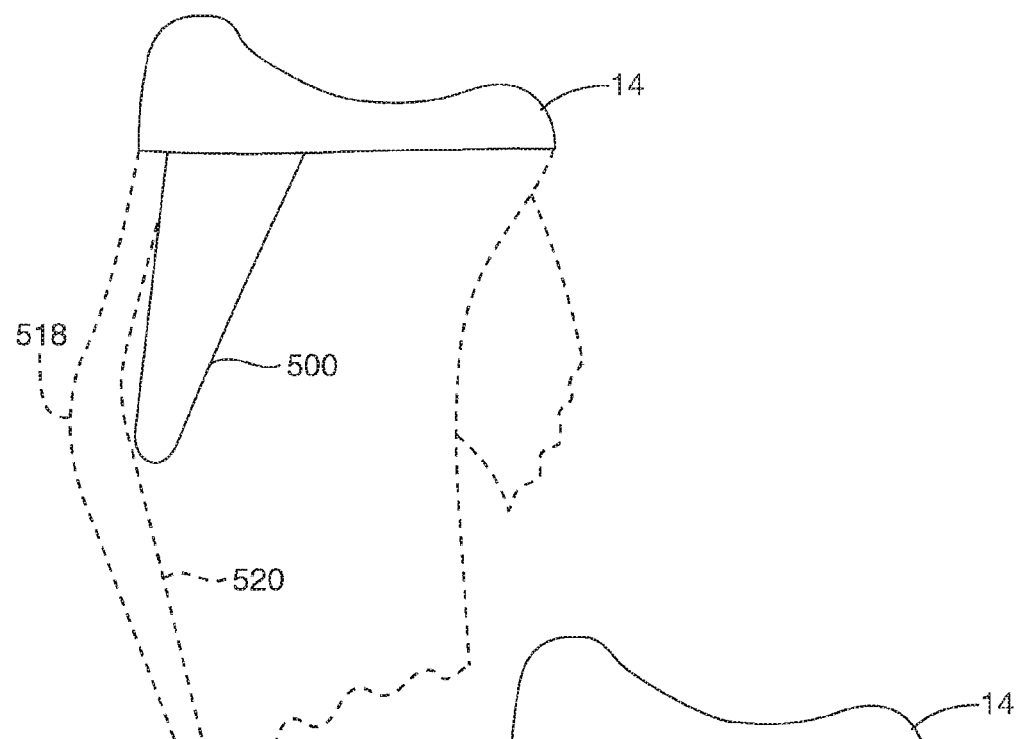
Figure 27:
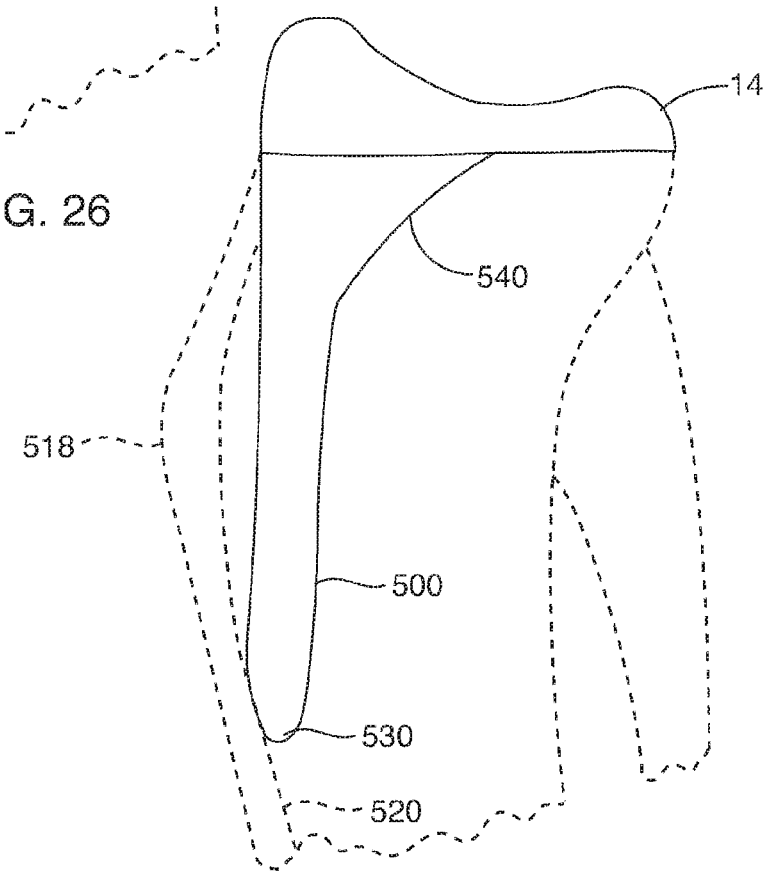
Figure 28A:
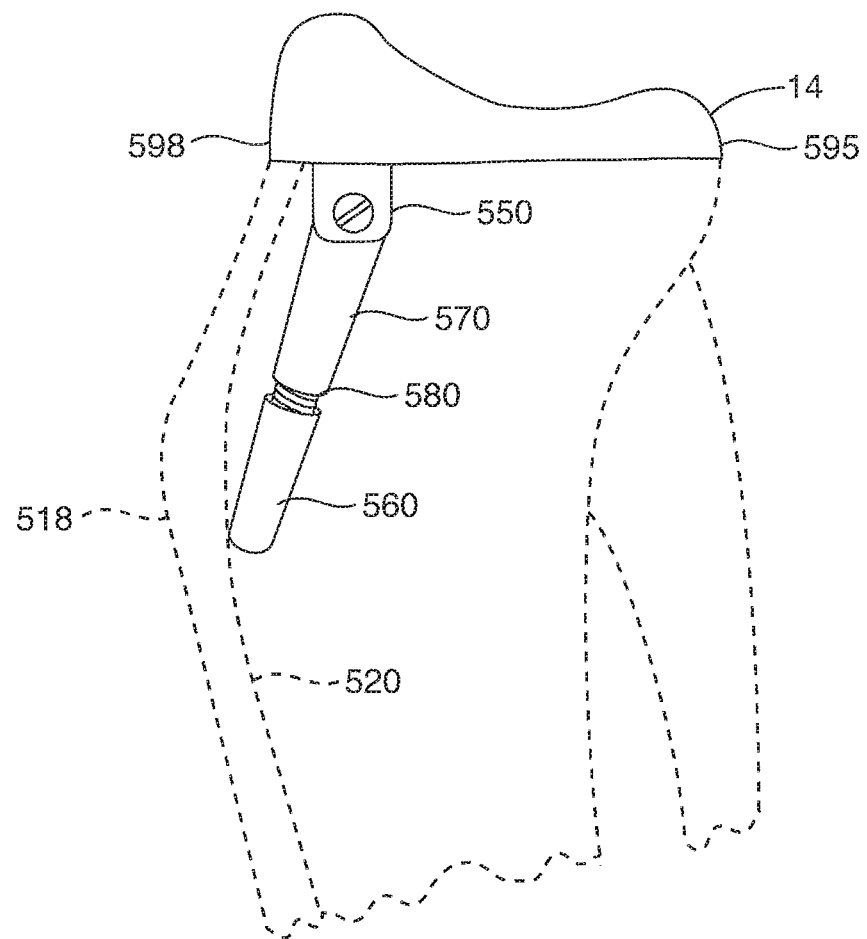
FIG. 28A illustrates an adjustable stem in accordance with a representative embodiment of the present invention.

In some embodiments, stem 500 is curved or otherwise shaped to closely approximate the contours of a portion of inner surface 520, as shown in FIGS. 24 and 25. In other embodiments, stem 500 is tapered such that portions of the stem surface contact various portions or areas of inner surface 520, as shown in FIG. 26. Still, in other embodiments, stem 500 is extended such that a tip portion 530 of stem 500 contacts inner surface 520. Stem 500 may further include tapered fins 540 to increase the stability of stem 500 while under compressive loads. In still some other embodiments, stem 500 comprises an adjustable linkage 550 whereby the angle of stem 500 is adjusted to accommodate the individual anatomy of the patient, as shown in FIG. 28A. In some embodiments, stem 500 further includes an adjustable tip 560 whereby the length of stem 500 is adjusted to accommodate the individual anatomy of the patient. For example, in some embodiments tip 560 is adjustably coupled to shaft 570 via a set of threads 580. In other embodiments, tip 560 is slidably coupled to shaft 570 wherein the position of the tip 560 relative to the shaft 570 is maintained via a set screw, a mechanical impingement, or an adhesive (not shown).

Thus, stem 500 may generally comprise any shape, size, length, or angle necessary to accommodate the needs of the patient. Additionally, stem 500 can comprise any suitable material. Indeed, in some embodiments, stem 500 is metal. In other embodiments, stem 500 is fabricated from a plastic, wherein the plastic stem may be trimmed at the time of surgery to allow an optimal fit.

Figure 28B:
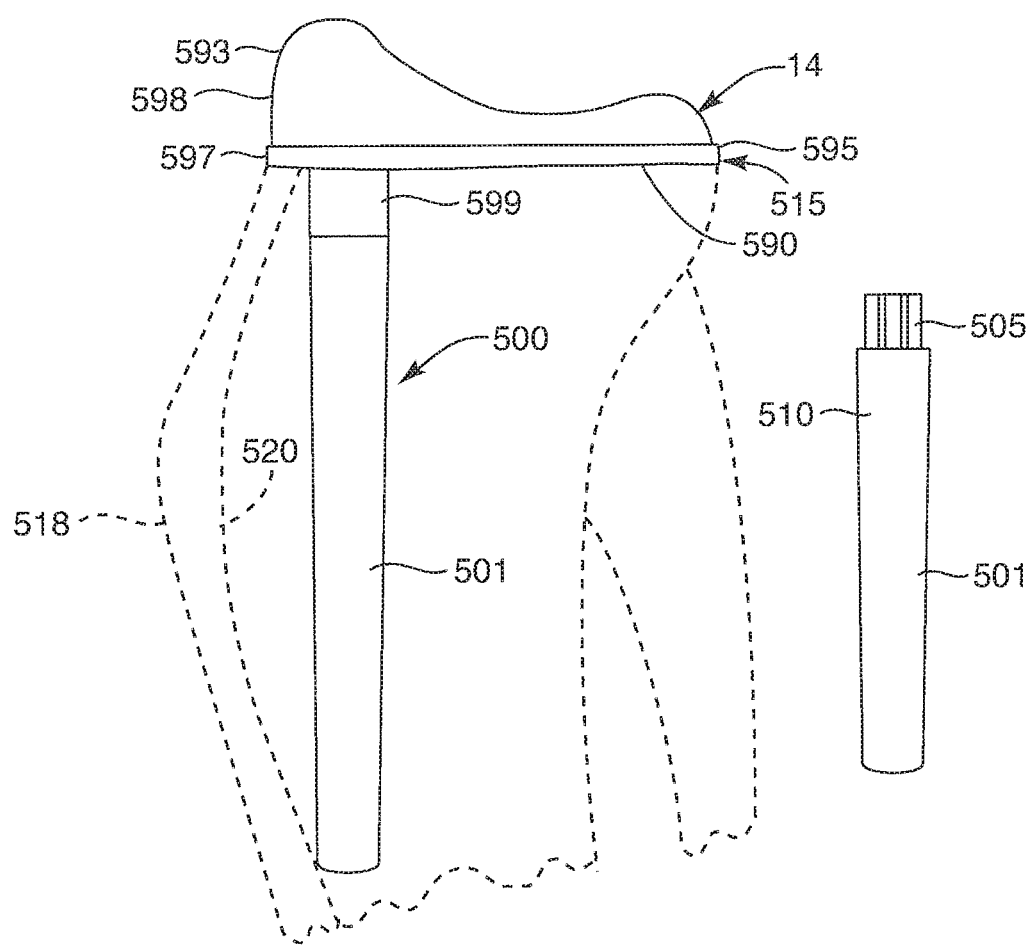
FIG. 28B illustrates a tibial component comprising a modular stem in accordance with a representative embodiment of the present invention.

In some embodiments, stem 500 comprises a modular stem that is interchangeable with one or more other stems of a varying size (e.g., length, circumference, diameter, volume, etc.) and/or shape (e.g., angle, curvature, taper, etc.). In this manner, a single tibial component 14 can be modified such that its stem 500 is able to contact the inner surface 520 of the tibial anterior cortex 518 of a variety of tibias having a different size and/or shape. For instance, in some embodiments in which the tibial component 14 is being placed on a relatively short tibia, a relatively short modular stem is attached to the tibial component such that a portion (e.g., a tip) of the stem is able to contact an inner surface of the bone's anterior cortex. In contrast, in some embodiments in which the tibial component is being attached to a relatively long tibia, a relatively long modular stem is attached to the tibial component.

Where stem 500 comprises a modular stem, the modular stem can connect to the tibial component 14 in any suitable manner, including, without limitation, through the use of one or more threaded connectors, frictional engagements, adhesives, fasteners (e.g., screws, bolts, pins, rivets, pawls, etc.), mechanical connectors, and/or other mechanisms that allow one of a variety of stems to be connected to the tibial component. By way of illustration, FIG. 28B shows a representative embodiment in which the undersurface 590 of the tibial component 14 (e.g., a tibial component comprising a polymer articulation surface 593 and metal base 597) comprises a connector 599 (e.g., a socket) that is configured to frictionally engage with a modular stem 501 (e.g., via splined member 505 that is sized and shaped to be inserted into connector 599, as seen on a replacement stem 510).

Where stem 500 comprises a modular stem (e.g., stem 501), the modular stem can be used in any suitable manner. Indeed, in some embodiments, one or more modular stems (or even trial stems, such as stems made from a disposable material, stems having a smaller diameter to reduce unnecessary damage to the medullary cavity, autoclavable stems, etc.) are coupled to and/or removed from undersurface 590 (e.g., connector 599) until the proper sized and/or shaped stem is found. At that point, the desired stem is permanently connected to the tibial component (e.g., via cement, one or more fasteners, mechanical engagements, etc.).

Where stem 500 comprises a modular stem (e.g., stem 501), the modular stems of various sizes and shapes can be sold in any suitable manner, including, without limitation, separately and/or in sets.

Additionally, where stem 500 comprises a modular stem (e.g., stem 501), the various modular stems can be configured to extend any suitable distance from the undersurface 590 of the tibial component 14. In some embodiments, the modular stems (and/or some embodiments of the non-modular stems) are configured to extend (when attached to the undersurface 590 of the tibial component 14) any suitable distance between about 1 cm and about 20 cm from undersurface 590. In other embodiments, the modular stems are configured to extend between about 3 and about 15 cm from the undersurface of the tibial component 14. In still other embodiments, the modular stems are configured to extend between about 5 and about 10 cm from the undersurface of the tibial component. In yet other embodiments, the modular stems are configured to extend to within any suitable sub-range of the aforementioned extension lengths.

Where the tibial component 14 includes stem 500 (e.g., a modular stem or a permanent stem that is configured to contact the inner surface 520 of the tibia, or the tibial anterior cortex 518), the undersurface 590 of the tibial component can contact the tibia in any suitable manner. Indeed, while the undersurface of the tibial component can be contoured in any suitable manner, in some embodiments, the undersurface of the tibial component 14 is substantially flat (e.g., as shown in FIG. 24).

Additionally, where the undersurface 590 of the tibial component 14 is substantially flat, the proximal end of the tibia can be cut at any suitable angle, and the undersurface 590 of the tibial component can have any suitable angle that allows it to attach to the tibia. In one example, the undersurface of the tibial component 14 is angled, and the proximal end of the tibia is cut such that the undersurface of the tibial component slopes (with respect to a longitudinal axis of the tibia) distally from the tibial component's posterior edge 595 towards the component's anterior edge 598 (see e.g., FIG. 24). In another example, undersurface 590 is angled, and the proximal end of the tibia is cut, such that the undersurface of the tibial component slopes (with respect to a longitudinal axis of the tibia) distally from the component's anterior edge 598 to the component's posterior edge 595. In still another example, the undersurface of the tibial component 14 is configured such that the undersurface runs substantially perpendicular to a longitudinal axis of the tibia 220.

In still other embodiments (not shown), the tibial component 14 lacks a stem 500 altogether. In such embodiments (as well as in embodiments in which the tibial component 14 comprises a modular stem 501 or a non-modular stem), the tibial component can be attached to a tibia in any suitable manner, including, without limitation through the use of cement (and/or another adhesive); one or more screws, bolts, pins, or other fasteners; any other suitable connection mechanism; and/or any suitable combination thereof. In this regard, in some embodiments in which the tibial component lacks a stem, undersurface 590 of the tibial component comprises one or more types of scaffolding, recesses, knurling, features (e.g., protuberances, holes, dovetailed grooves, etc.), and/or any other structures or surface characteristics that allows cement (and/or bone) to attach securely to the undersurface of the tibial component.

Figure 29A:
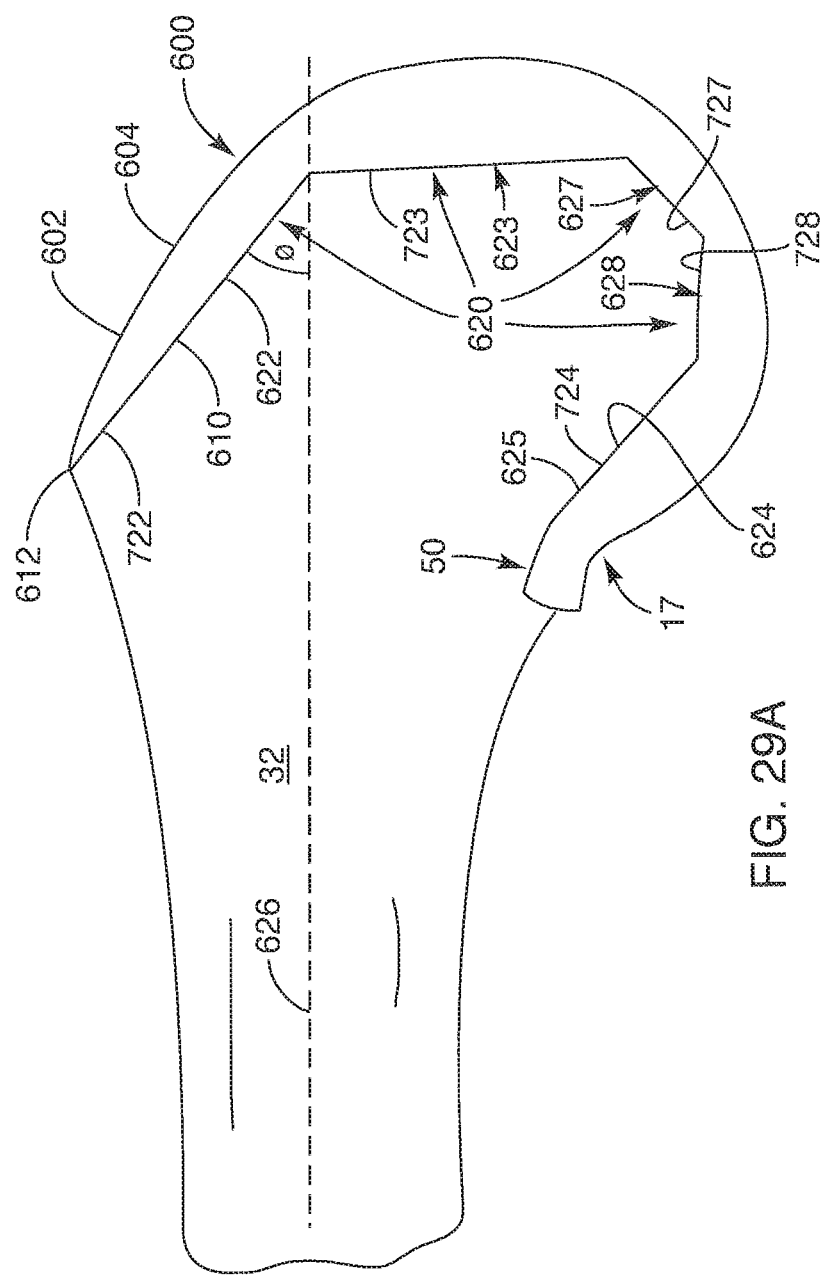
FIGS. 29A-29C each illustrate a different representative embodiment of an implanted femoral component having two opposing internal surfaces that run substantially parallel to each other.

In some embodiments, a femoral component 600 is provided having an anterior extension 602 that generally replaces a resectioned antero-proximal portion of the anterior condyles 610, as shown in FIG. 29A. In some embodiments, the antero-proximal portion of the anterior condyles 610 is prepared by resecting the anterior condyle surface to the proximal limit 612 of the articular cartilage. As such, essentially all of the anterior articular cartilage is removed from the resected femur 32. In other embodiments, however, the anterior condyle surface of the femur is resected to any distance within (or any sub-range of) about 0 mm and about 15 mm on either the distal or the proximal side of the proximal limit 612 of the articular cartilage. In one non-limiting example, the anterior condyle surface of the femur is resected to between about 1 mm and about 6 mm on either the distal or the proximal side of the proximal limit 612 on the articular cartilage. In another non-limiting embodiment, the anterior surface of the femur is resected proximally to any suitable amount less than about 15 mm of the proximal limit 612 of the articular cartilage.

In some embodiments, the anterior articular cartilage is removed while removing little or no other bone anteriorly. In other words, in some embodiments, femoral component 600 replaces essentially all anterior articular cartilage, but little or no other bone anteriorly. Accordingly, in some embodiments, the only bone removed is sub-chondral bone next to the cartilage and any bone necessary to allow a component to fit the distal end of the femur. Thus, in some embodiments, femoral component 600 is able to terminate at (or adjacent to (e.g., within about 0 and about 15 mm (or any suitable sub-range thereof) on either the distal or the proximal side of)) the proximal limit 612. Moreover, in some embodiments, a resected distal end of the femur 32 is fitted with a femoral component 600 wherein patellar force against the femur (in extension) is substantially, if not completely, eliminated due to having replaced the anterior articular cartilage with which the patella normally articulates. Accordingly, in some embodiments, the resectioned antero-proximal portion of the anterior condyles 610 is replaced with an anterior condylar extension 602 thereby providing a new surface 604 against which the patient's patella may articulate.

As shown in FIG. 29A, in some embodiments, femoral component 600 lacks an anterior flange (as discussed above) such that the femoral component substantially ends at or distally (e.g., within about 0 mm and about 15 mm, or any sub-range thereof) the proximal limit 612.

In some embodiments, the new articular surface 604 provides a substantially smooth transition between femoral component 600 and femur 32 at (or near) proximal limit 612. Further, by removing only the articular cartilage and the underlying sub-chondral and cancellous bone from femur 32, a smaller, less expensive femoral component 600 may be provided, which also results in a less invasive implantation for the patient. Moreover, by allowing more bone to be preserved anteriorly on the femur, femoral component 600 may allow for faster, less complicated preparation of the femur than may be accomplished with some competing femoral prosthesis.

In some embodiments, femoral preparation and implantation of femoral component 600 is performed using surgical instruments common to standard knee systems and procedures. In other embodiments, standard surgical instruments are used to make all of the desired cuts to the distal femur, however, in some embodiments, the standard anterior femoral cut is not made. The standard antero-distal femoral cutting guide with most systems is typically adequate to remove essentially all anterior cartilage to the proximal limit 612. Accordingly, there is no significant increase in instrument costs to implant femoral component 600 as opposed to a standard femoral component.

Further, since the antero-distal condylar cuts to the femur 32 may comprise standard cuts for fitting a standard femoral component, in some embodiments, a surgeon does not need to predetermine use of femoral component 600 or a standard femoral component until they have completed all femoral cuts excepting the antero-distal cut, as this cut lies in roughly the same plane as the anterior femoral cortex. If the surgeon desires to implant femoral component 600, the surgeon cuts the antero-proximal portion of the posterior condyles 625 using a non-standard cutting guide. The standard antero-distal cut removes essentially all anterior cartilage to the proximal limit 612. Conversely, if the surgeon desires to implant a standard femoral component, the surgeon makes the standard anterior cut necessary to accommodate implantation of a standard femoral implant.

In one non-limiting example of a resected femur 32 suitable for use with femoral component 600, FIG. 29A shows some embodiments in which femur 32 is resected to include an anterior chamfer cut 622 (or anterior oblique cut, see FIG. 12C), a distal cut 623, a posterior chamfer cut 627, a posterior condylar cut 628, and a full flexion cut 624 (e.g., a cut extending proximally and anteriorly from the posterior condylar cut 628 and/or towards a popliteal surface and/or posterior surface on the shaft of the femur).

The interior profile surfaces 620 of the femoral component 600 can be designed to match the interior profile of any conventional, standard femoral component. In some embodiments, however, the interior profile surfaces of opposing surfaces (e.g., internal surface 722, which interfaces with the anterior chamfer cut 622 and internal surface 724, which interfaces with the full flexion cut 624) of the femoral component are exactly parallel or (in some cases) substantially parallel to allow a press-fit (including, without limitation, a cementless) or cemented application of femoral component 600 to resected surfaces (e.g., 622, 623, 624,

627, and 628). In other embodiments, the interior profile surfaces of the opposing surfaces (e.g., 722 and 724) diverge from each other (or from being parallel with each other) by more than about 45°. In still other embodiments, however, the opposing surfaces (e.g., 722 and 724) diverge by less than about 45°. Indeed, in some embodiments, the opposing surfaces diverge from each other by between about 0° and about 45°. In still other embodiments, the opposing surfaces diverge from each other by between about 3° and about 25°. In even other embodiments, the opposing surfaces diverge from each other by between about 5° and about 10°. In yet other embodiments, the opposing surfaces diverge from each other by any suitable sub-range of any of the aforementioned ranges (e.g., between about 4° and about 8°). Additionally, while the opposing surfaces (e.g., 722 and 724) may diverge in any suitable direction, in some embodiments, when femoral component 600 is attached to a femur 32, the opposing surfaces (or at least a portion of opposing surfaces) diverge from each other as the surfaces run proximally.

Femoral component 600 can be attached to resected femur 32 in any suitable manner. Indeed, while, in some embodiments, the femoral component is configured to be rolled onto the femur, in other embodiments, the femoral component is slid onto the femur without rolling. In the latter embodiments, the femoral component can be slid onto the femur in any suitable manner. In one non-limiting example, where the opposing surfaces (e.g., 722 and 724) diverge as they run distally on a femur 32, the opposing surfaces are forced slightly further apart to allow the component to be slid onto and press-fitted to the femur. In this example, once the femoral component is in place, the opposing surfaces are allowed to return to the original position, which can help maintain the femoral component in place on the femur. In another example, where the opposing surfaces (e.g., 722 and 724) diverge as they run proximally on a femur 32 (e.g., giving the femur a slightly wedge-like characteristic), femoral component 600 is slid on and press-fitted to the femur.

Where the femoral component 600 is slid onto the femur 32, the femoral component can be slid on at any suitable angle relative to a longitudinal axis of the femur's shaft that allows the femoral component to replace a desired portion of the femur's articulating surfaces. In some embodiments, where the femoral component is slid onto the femur, it is slid at an angle θ (with respect to a longitudinal axis 626 of femur 32, as shown in FIG. 29A) of between about 30° and about 55°. In other embodiments, the femoral component is slid onto the femur at an angle between about 30° and about 45°. In yet other embodiments, femoral component 600 is slid on the femur any angle that falls in any suitable combination or sub-range of the aforementioned ranges of angles.

The femoral component 600 can be attached to the femur 32 in any suitable manner, including through the use of cement (i.e., any suitable adhesive); one or more screws, pins, or other mechanical fasteners; a pressure fitting (e.g., a friction fitting with or without cement); and/or any other known or novel method for attaching a prostheses to a femur. In some embodiments, however, the femoral component is simply cemented (as mentioned earlier) to the femur. In still other embodiments, one or more surfaces of the femoral component 600 that attach to the femur 32 comprise a texture (e.g., a porous texture, scaffolding, recesses, and/or other features) that allows bone to grow into the texturized surface.

The femoral component 600 can be modified in any suitable manner. Indeed, while in some embodiments, the femoral component is configured to replace all of the articulating surfaces of a femur (e.g., in a full femoral knee replacement), in other embodiments, the femoral component is configured to be used in a unicompartmental femoral knee replacement. Where the femoral component is used in a unicompartmental knee replacement, the component can be used in any suitable location (e.g., medially and/or laterally on the femur).

Figure 29B:
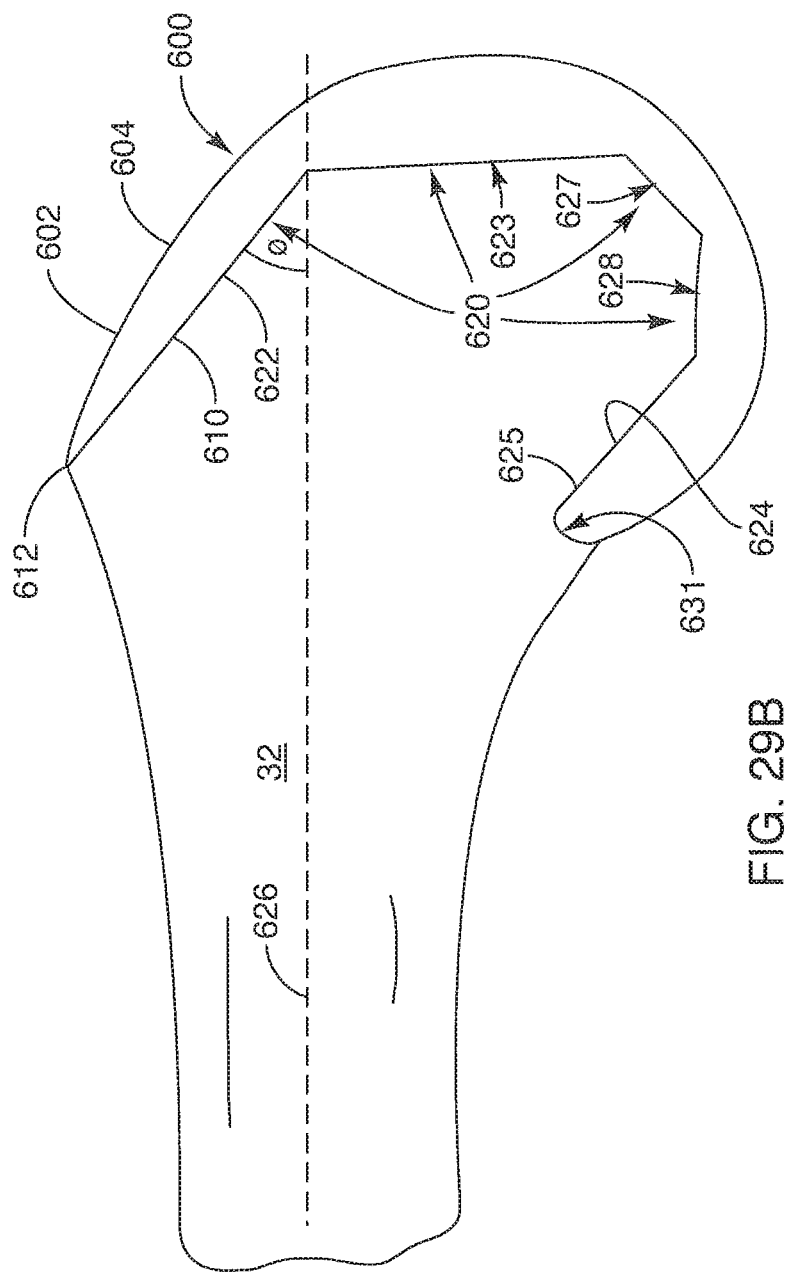
Figure 29C:
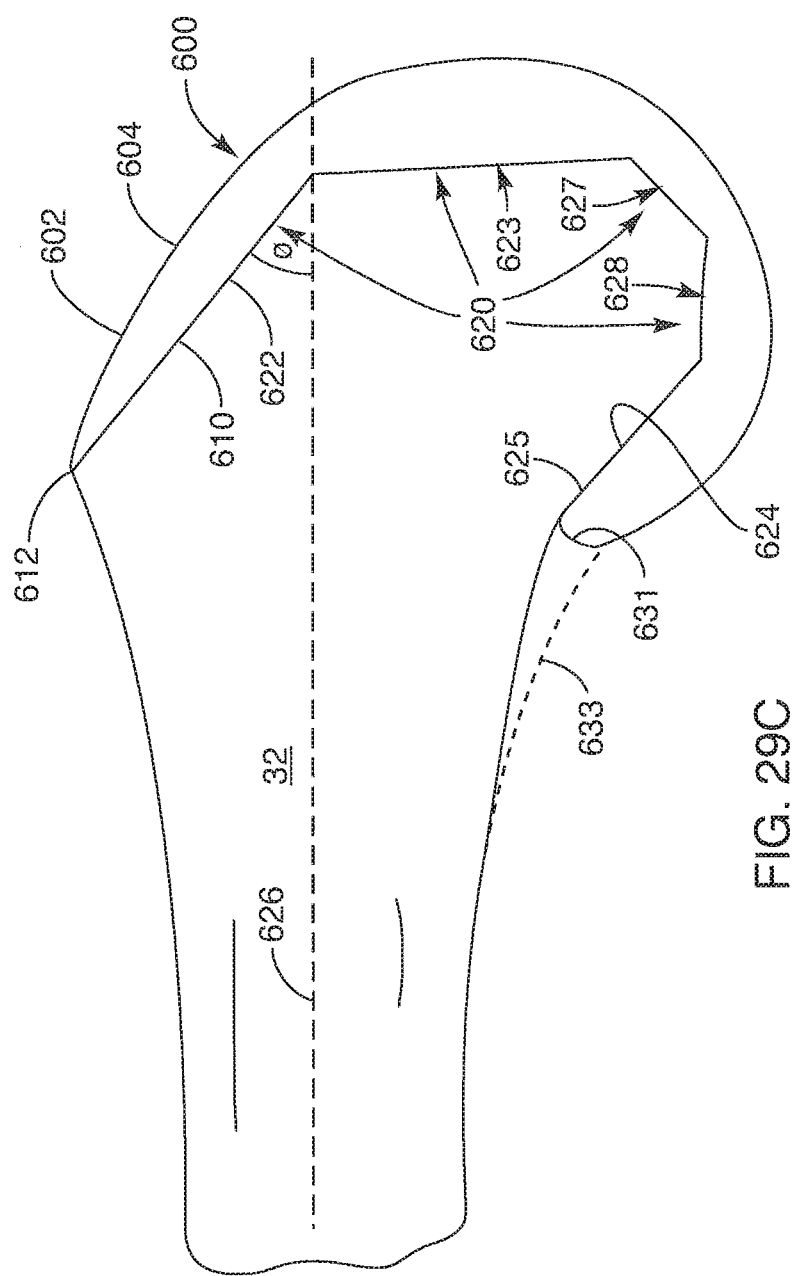

In another example of how the femoral component can be modified, in some embodiments, the femoral component comprises a full flex articulation 50 (as discussed above and as shown in FIG. 29A). In another example, however, FIGS. 29B and 29C show that, in some embodiments, femoral component 600 optionally lacks the full flex articulation. In this example, FIG. 29B shows that, in some such embodiments, a posterior portion of the femur 32 can be removed so that the bone abuts and substantially corresponds with the shape of the proximal end 631 of femoral component 600. In contrast, FIG. 29C shows that, in some embodiments, either because of the natural shape of a patient's femur 32 or because a surgeon removes a posterior portion of the femur 32 (as illustrated by the dashed line 634), the posterior portion of the femur 32 does not abut with proximal end 631 of the posterior portion of femoral component 600.

In still another example, (discussed above) the full flexion articulation 50 is added to femoral component 600 as a modular unit. In yet another example, femoral component 600 replaces a popliteal surface of femur 32. In still another example, the femoral component is configured to receive a modular anterior flange 57 (as discussed above).

Thus, as discussed herein, the embodiments of the present invention embrace knee prostheses. In particular, the present invention relates to systems and methods for providing deeper knee flexion capabilities for knee prosthesis patients, more particularly, by effectuating one or more of the following: (i) providing a greater articular surface area to the femoral component of a knee prosthesis, with either a modification of, or an attachment to the femoral component of a knee prosthesis, which when integrated with a patient's femur and an appropriate tibial component, results in full functional flexion; (ii) providing modifications to the internal geometry of the femoral component and the opposing femoral bone with methods of implanting; (iii) providing asymmetrical under surfaces on the tibial component of the knee prosthesis and uniquely-positioned articular surfaces to facilitate full functional flexion; (iv) asymmetrical femoral condylar surfaces with a lateralized patellar (trochlear) groove to more closely replicate physiologic loading of the knee and to provide better tracking of the patella; and (v) resection of essentially all of the anterior femoral articular cartilage and underlying bone, but no additional bone and replacing it with a femoral component that does not have an anterior flange as seen on contemporary prostheses.

The present invention may be embodied in other specific forms without departing from its spirit or essential characteristics. For example, one of skill in the art will appreciate that the methods and systems of the present invention may be modified for use in unicompartmental knee arthroplasty procedures and prostheses. The methods and systems of the present invention may further be used on the lateral side of the knee instead of, or in combination with the medial side. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A femoral component configured to replace a distal portion of a femur, the femoral component comprising:
   a first interior surface; and
   a second interior surface,
   wherein the first and second interior surfaces are respectively configured to contact a first resected portion and a second resected portion of the femur,
   wherein the first interior surface and the second interior surface run substantially parallel with each other,
   wherein the first interior surface is configured to interface with an anterior chamfer cut surface of the femur, and
   wherein the femoral component is configured such that when the femoral component is seated on the distal portion of the femur, the first interior surface runs at an angle between about 30 degrees and 55 degrees with respect to a longitudinal axis of a distal portion of the femur.

2. The component of claim 1, wherein a proximal, anterior end of the femoral component is configured to end within about 10 mm of a proximal end of the anterior chamfer cut surface when the femoral component is seated on the femur.

3. The component of claim 1, wherein the femoral component further comprises an incurvate articulation surface that is disposed at a proximal portion of a posterior condyle of the femoral component.

4. The component of claim 1, further comprising a modular anterior flange that is configured to couple with a proximal, anterior end of the femoral component.

5. The component of claim 1, wherein the first and second interior surfaces diverge from being parallel with each other by less than about 10°.

6. The component of claim 1, wherein a posterior proximal portion of the femoral component is configured to replace a popliteal surface of the femur.

7. A femoral component, comprising:
   a first interior surface configured to contact an anterior chamfer cut surface of a femur; and
   a second interior surface configured to contact a posterior condylar portion of the femur,
   wherein the first interior surface and the second interior surface are within about 20 degrees of being parallel with each other, and
   wherein the first interior surface is configured such that when the femoral component is seated on a distal portion of the femur, the first interior surface runs at an angle between about 30 degrees and about 55 degrees with respect to a longitudinal axis of a distal end of the femur.

8. The component of claim 7, wherein the femoral component further comprises:
   a third interior surface that is configured to interface with a distal cut surface of the femur;
   a fourth interior surface that is configured to interface with a posterior chamfer cut surface of the femur; and
   a fifth interior surface that is configured to interface with a posterior condylar cut surface of the femur.

9. The component of claim 7, wherein the first and second interior surfaces diverge from being parallel with each other by less than about 8°.

10. The component of claim 7, wherein the first interior surface runs at an angle between about 30 degrees and about 45 degrees with respect to the longitudinal axis of the distal end of the femur.

11. The component of claim 7, wherein the femoral component further comprises an incurvate articulation surface that is disposed at a proximal portion of a posterior medial condyle of the femoral component.

12. The component of claim 7, further comprising a modular anterior flange that is configured to couple with a proximal, anterior end of the femoral component.

13. The component of claim 7, wherein a proximal, anterior end of the femoral component is configured to end within about 8 mm of a proximal end of the anterior chamfer cut surface when the femoral component is seated on the femur.

14. The component of claim 7, further comprising a modular component having an articular surface that is configured to couple with the femoral component to extend an articulation surface of a posterior condylar of the femoral component, at a proximal end of the articulation surface.

15. A femoral component, comprising:
    a first interior surface configured to contact an anterior chamfer cut surface of a femur;
    a second interior surface configured to contact a femoral cut surface at a posterior condylar portion of the femur, the femoral cut surface extending proximally and anteriorly from a distal end of the femoral cut surface and towards a posterior surface of the femur,
    wherein the first interior surface and the second interior surface are within about 20 degrees of being parallel with each other, and
    wherein the first interior surface is configured such that when the femoral component is seated on a distal portion of the femur, the first interior surface runs at an angle between about 30 degrees and about 55 degrees with respect to a longitudinal axis of the distal end of the femur.

16. The component of claim 15, wherein a proximal, anterior end of the femoral component is configured to end within about 6 mm of a proximal end of the anterior chamfer cut surface when the femoral component is seated on the femur.

17. The component of claim 16, wherein the femoral component comprises:
    a third interior surface that is configured to interface with a distal cut surface of the femur;
    a fourth interior surface that is configured to interface with a posterior chamfer cut surface of the femur; and
    a fifth interior surface that is configured to interface with a posterior condylar cut surface of the femur.

18. The component of claim 16, wherein the femoral component further comprises an incurvate articulation surface that is disposed at a proximal portion of a posterior medial condyle of the femoral component.

19. The component of claim 17, wherein the first interior surface runs at an angle between about 30 degrees and about 45 degrees with respect to the longitudinal axis of the distal end of the femur.

20. The component of claim 15, wherein a posterior proximal portion of the femoral component is configured to replace a popliteal surface of the femur.

* * * * *